US012636368B2

(12) United States Patent
Thomas et al.

(10) Patent No.: US 12,636,368 B2
(45) Date of Patent: May 26, 2026

(54) IONIZABLE LIPIDS FOR NUCLEIC ACID DELIVERY

(71) Applicant: Global Life Sciences Solutions Canada ULC, Vancouver (CA)

(72) Inventors: Anitha Thomas, New Westminster (CA); Nikita Jain, Vancouver (CA); Andrew William Brown, Vancouver (CA)

(73) Assignee: GLOBAL LIFE SCIENCES SOLUTIONS CANADA ULC, Vancouver (CA)

( * ) Notice: Subject to any disclaimer, the term of this patent is extended or adjusted under 35 U.S.C. 154(b) by 1190 days.

(21) Appl. No.: 17/622,096

(22) PCT Filed: Jun. 26, 2020

(86) PCT No.: PCT/CA2020/050897
§ 371 (c)(1),
(2) Date: Dec. 22, 2021

(87) PCT Pub. No.: WO2021/000041
PCT Pub. Date: Jan. 7, 2021

(65) Prior Publication Data
US 2022/0378917 A1     Dec. 1, 2022

Related U.S. Application Data

(60) Provisional application No. 63/009,042, filed on Apr. 13, 2020, provisional application No. 62/868,900, filed on Jun. 29, 2019.

(51) Int. Cl.
| | |
|---|---|
| *A61K 47/54* | (2017.01) |
| *A61K 39/00* | (2006.01) |
| *A61K 39/39* | (2006.01) |
| *A61K 47/69* | (2017.01) |
| *C07D 307/20* | (2006.01) |
| *C07D 405/12* | (2006.01) |
| *C07D 453/02* | (2006.01) |

(52) U.S. Cl.
CPC .... *A61K 47/543* (2017.08); *A61K 39/001112* (2018.08); *A61K 39/39* (2013.01); *A61K 47/6929* (2017.08); *C07D 307/20* (2013.01); *C07D 405/12* (2013.01); *C07D 453/02* (2013.01); *A61K 2039/5156* (2013.01); *A61K 2039/5158* (2013.01)

(58) Field of Classification Search
CPC ............................ A61K 47/543; C07D 307/20
See application file for complete search history.

(56) References Cited

U.S. PATENT DOCUMENTS

| | | | |
|---|---|---|---|
| 5,576,161 A | 11/1996 | Nishimura et al. |
| 5,753,613 A | 5/1998 | Ansell et al. |
| 6,734,171 B1 | 5/2004 | Saeravolac et al. |
| 8,158,601 B2 | 4/2012 | Chen et al. |
| 9,758,795 B2 | 9/2017 | Cullis et al. |
| 9,943,846 B2 | 4/2018 | Cullis et al. |
| 9,999,673 B2 | 6/2018 | Rajeev et al. |
| 10,076,730 B2 | 9/2018 | Wild et al. |
| 2004/0262223 A1 | 12/2004 | Strook et al. |
| 2011/0117125 A1 | 5/2011 | Hope et al. |
| 2014/0200257 A1 | 7/2014 | Rajeev et al. |
| 2016/0022580 A1 | 1/2016 | Ramsay et al. |

FOREIGN PATENT DOCUMENTS

| | | | |
|---|---|---|---|
| CA | 3 044 134 A1 | 7/2009 |
| CA | 2 743 135 A1 | 5/2010 |
| CN | 102281899 A | 12/2011 |
| CN | 104321304 A | 1/2015 |
| EP | 3 202 760 A1 | 8/2017 |
| JP | H8-54716 A | 2/1996 |
| JP | 2009-52102 A | 3/2009 |
| JP | 2011-509258 A | 3/2011 |
| JP | 2014-505145 A | 2/2014 |
| WO | WO 2009/086558 A1 | 7/2009 |

(Continued)

OTHER PUBLICATIONS

Chinese National Intellectual Property Administration, Office Action issued in counterpart Chinese Patent Application No. 202080047923. 6, mailed on Jan. 17, 2024.

(Continued)

*Primary Examiner* — David K O'Dell

(74) *Attorney, Agent, or Firm* — Lathrop GPM LLP; Malaika O.D. Tyson; Jason Kuchar

(57) ABSTRACT

The present document describes compounds, or pharmaceutically acceptable salt thereof, of a core formula (I) Wherein R1 includes an amino group. These compounds are particularly useful in the formulation and in vivo and ex vivo delivery of nucleic acid and protein therapeutics for preparing and implementing T cell transfection, gene editing, cancer therapies, cancer prophylactics, and in the preparation of vaccines.

(I)

23 Claims, 12 Drawing Sheets

(56) References Cited

FOREIGN PATENT DOCUMENTS

| | | | | |
|----|----------------------|--------|-----------|
| WO | WO 2010/054405 A1 | 5/2010 | |
| WO | WO 2012/099755 A1 | 7/2012 | |
| WO | WO 2012/108397 A1 | 8/2012 | |
| WO | WO 2013/126803 A1 | 8/2013 | |
| WO | WO-2016028851 A1 * | 2/2016 | .......... C07D 307/20 |
| WO | WO 2017/117647 A1 | 7/2017 | |
| WO | WO 2018/006166 | 1/2018 | |
| WO | WO-2018062413 A1 * | 4/2018 | ............. A61K 9/127 |

OTHER PUBLICATIONS

Canadian Intellectual Property Office; International Search Report in counterpart International Application No. PCT/CA2020/050897, mailed on Aug. 25, 2020.

Leung, Alex K.K. et al., "Chapter Four—Lipid Nanoparticles for Short Interfering RNA Delivery", *Advances in Genetics*, vol. 88, 2014, pp. 71-110.

Zhi, Defu et al., "Historic perspective. A review on cationic lipids with different links for gene delivery", *Advances in Colloids and Interface Science*, 2018, vol. 253, pp. 117-140.

European Patent Office, Extended European Search Report issued in counterpart European Patent Application No. 20835492.8, mailed on Jul. 22, 2022.

Jubeli et al., "Next generation macrocyclic and acyclic cationic lipids for gene transfer: Synthesis and in vitro evaluation", *Bioorganic & Medicinal Chemistry*, vol. 23, No. 19, pp. 6364-6378 (2015).

Japanese Patent Office, Office Action issued in counterpart Japanese Patent Application No. 2021-577003, mailed on Aug. 8, 2023.

Niyomtham et al., "Synthesis and in vitro transfection efficiency of spermine-based cationic lipids with different central core structures and lipophilic tails", *Bioorganic & Medicinal Chemistry Letters*, 25(3): 496-503 (2015)—Abstract only.

* cited by examiner

CD19 CAR%

IONIZABLE LIPIDS FOR NUCLEIC ACID DELIVERY

CROSS-REFERENCE TO RELATED APPLICATIONS

This patent application is the U.S. National Stage of International Patent Application No. PCT/CA2020/050897, filed Jun. 26, 2020, which claims priority to U.S. provisional patent applications 62/868,900 filed on Jun. 29, 2019, and 63/009,042 filed on Apr. 13, 2020, which are each incorporated by reference.

FIELD

The subject matter disclosed generally relates to ionizable lipids, specifically those ionizable lipids capable of transfecting living cells with genetic material.

BACKGROUND

Related Prior Art

The number of nucleic acid treatment strategies for disease, even those diseases that do not have an initial genetic cause, is growing. Each nucleic acid therapeutic has a different form, chemistry, and charge, and typically requires a different delivery modality.

Lipofection has been studied as a means of altering the genetics of cells through lipid mediated gene delivery since at least 1987. Over years, refinements have been made to such lipids to adapt them to more situations. Cationic lipids like DODAC, DOTMA, DDAB, and DOTAP were used in the 1990s, but proved too toxic to contemplate for clinical applications.

A clinically relevant approach has been the development of ionizable lipids for human use. Examples of ionizable lipids include, 1,2-dilinoleyloxy-3-dimethylaminopropane (DLin-DMA), dilinoleylmethyl-4-dimethylaminobutyrate (DLin-MC3-DMA, (see e.g., U.S. Pat. No. 8,158,601), and 2-dilinoleyl-4-dimethylaminoethyl-[1,3]-dioxolane (DLin-KC2-DMA). DLin-MC3-DMA or "MC3" is employed in Onpattro™ patisiran, an approved drug, but has shelf-life issues.

The need for more options for clinically relevant transfection lipids continues to exist.

SUMMARY

According to embodiments of the invention, there is provided a compound, or a pharmaceutically acceptable salt thereof, of formula (I)

(I)

Wherein p is 0 or 1;

$E_1$ is selected from $\_O\_\delta_1$, $\_OC(O)O\_\delta_1$, $\_OC(O)\_\delta_1$, $\_OC(O)N(Q)\_\delta_1$, $\_OC(O)S\_\delta_1$, $\_C(O)N(Q)\_$ $\delta_1$, $\_C(O)O\_\delta_1$, $\_N(Q)C(O)\_\delta_1$, $\_N(Q)C(O)O\_\delta_1$, $\_N(Q)C(O)S\_\delta_1$, and $\_N(Q)C(O)N(Q)\_\delta_1$; Q is H or $C_1$-$C_5$ alkyl; $\delta_1$ designates the bond linked to the $R_1$ group;

$R_1$ is selected from:

wherein:

$R_3$ and $R_4$ are each independently selected from a group consisting of $C_1$-$C_6$ alkyl, $C_2$-$C_6$ alkenyl, and $C_2$-$C_6$ alkynyl; alternatively $R_3$ and $R_4$ may join to form 4-6 membered ring containing oxygen (O) or up to 2 nitrogen (N), optionally substituted with 1-2 substituents, each independently selected from a $C_1$-$C_6$ alkyl, cyclopropyl, OH, and a $C_1$-$C_3$ alkoxy group;

$R_5$ is selected from $C_1$-$C_6$ alkyl, $C_2$-$C_6$ alkenyl, $C_2$-$C_6$ alkynyl, $C_3$-$C_6$ cycloalkyl, and a 2-hydroxyethyl group;

$R_6$ is selected from H, and $C_1$-$C_6$ alkyl group;

a is 1, 2, 3, 4 or 5;

b and c are independently 0, 1, or 2;

c' is 1, 2, 3, 4, or 5;

d is 1, or 2;

e is 0, 1, or 2;

$E_2$ is selected from $\_OC(O)\text{-}\delta_2$, $\_OC(O)O\text{-}\delta_2$, $\_OC(O)N(Q)\text{-}\delta_2$, $\_O\text{-}\delta_2$, $\_OCH_2CH_2O\text{-}\delta_2$, and $\_OC(O)(CH_2)_6C(O)O\text{-}\delta_2$; Q is H or $C_1$-$C_5$ alkyl; $\delta_2$ designates the bond linked to the $R_2$ group;

$R_2$ is selected from or has the formula $\_(CH_2)_g\_[L_3\text{-}(CH_2)]_h\_R_9$, wherein:

$L_1$ and $L_2$ are each, independently, a direct bond, $\_O\text{-}\delta_3$, $\_CH_2OC(O)\text{-}\delta_3$, and $\_CH_2O\text{-}\delta_3$; $\delta_3$ designates the bond linked to the $R_7$ and $R_8$ group;

$R_7$ and $R_8$ are each independently $C_4$-$C_{10}$ alkyl, $C_4$-$C_{10}$ alkenyl or $C_4$-$C_{10}$ alkynyl;

f is 0, 1, 2, 3, 4, or 5;

$L_3$ is selected from $R_9$ is selected from H and $C_4$-$C_8$ alkyl group;
g is an integer in the range of 1-18;
h is 0, 1, 2, or 3;

According to other embodiments of the invention, there is provided a compound, or a pharmaceutically acceptable salt thereof, of formula (II)

(II)

Wherein $E_1$ is selected from _OC(O)O_$\delta_1$, _OC(O)_$\delta_1$, _OC(O)N(Q)_$\delta_1$, and _OC(O)S_$\delta_1$; Q is H or $C_1$-$C_5$ alkyl; and $\delta_1$ designates the bond linked to the $R_1$ group;

$R_1$ is selected from:

wherein:
R₃ and R₄ are each independently selected from a $C_1$-$C_6$ alkyl group; alternatively $R_3$ and $R_4$ may join to form 5-6 membered ring containing up to 2 nitrogen (N), optionally substituted with 1-2 substituents selected from a $C_1$-$C_6$ alkyl group;
$R_5$ is selected from a $C_1$-$C_6$ alkyl, and $C_3$-$C_6$ cycloalkyl group;
$R_6$ is selected from an H, and $C_1$-$C_6$ alkyl group;
a is 1, 2, 3, or 4;
b and c are independently 0, 1, or 2;
c' is 2, 3, or 4;
d is 2;
e is 0, or 1;

$E_2$ is selected from —O-$\delta_2$, —OC(O)-$\delta_2$, —OCH$_2$CH$_2$O-$\delta_2$, and —OC(O)(CH$_2$)$_6$C(O)O-$\delta_2$; where $\delta_2$ designates the bond linked to the $R_2$ group;

$R_2$ is selected from or has the formula _(CH$_2$)$_g$_[L$_3$-(CH$_2$)]$_h$_R$_9$, wherein:
$L_1$ and $L_2$ are each, independently, a direct bond, —O-$\delta_3$, —CH$_2$OC(O)-$\delta_3$, and —CH$_2$O-$\delta_3$; $\delta_3$ designates the bond linked to the $R_7$ and $R_8$ group;
$R_7$ and $R_8$ are each independently $C_4$-$C_{10}$ alkyl, $C_4$-$C_{10}$ alkenyl or $C_4$-$C_{10}$ alkynyl;
f is 0, 1, 2, 3, 4, or 5;
$L_3$ is selected from $R_9$ is selected from H and a $C_4$-$C_8$ alkyl group;
g is an integer in the range of 1-18;
h is 0, 1, or 2;

According to other embodiments of the invention, there is provided a compound, or a pharmaceutically acceptable salt thereof, of formula (II)

(II)

Wherein $E_1$ is selected from _OC(O)O_$\delta_1$, _OC(O)_$\delta_1$, _OC(O)N(Q)_$\delta_1$, and _OC(O)S_$\delta_1$; Q is H or $C_1$-$C_5$ alkyl; and $\delta_1$ designates the bond linked to the $R_1$ group;

$R_1$ is selected from:

-continued wherein:

$R_3$ and $R_4$ are each independently selected from a $C_1$-$C_6$ alkyl group; alternatively $R_3$ and $R_4$ may join to form 5-6 membered ring containing up to 2 nitrogen (N), optionally substituted with 1-2 substituents selected from a $C_1$-$C_6$ alkyl group;

$R_5$ is selected from $C_1$-$C_6$ alkyl, and cyclopropyl group;

$R_6$ is selected from H, and $C_1$-$C_6$ alkyl group;

a is 1, 2, 3, or 4;

b is 0, or 1;

c is 0, 1, or 2;

c' is 2, 3, or 4;

d is 2;

e is 1;

$E_2$ is selected from —O-$\delta_2$, —OC(O)-$\delta_2$, —OCH$_2$CH$_2$O-$\delta_2$, and —OC(O)(CH$_2$)$_6$C(O)O-$\delta_2$; where $\delta_2$ designates the bond linked to the $R_2$ group;

$R_2$ is selected from or has the formula _(CH$_2$)$_g$_[L$_3$-(CH$_2$)]$_h$_R$_9$, wherein:

$L_1$ and $L_2$ are each a direct bond;

$R_7$ and $R_8$ are each independently selected from $C_4$-$C_{10}$ alkyl group;

f is 0, or 1;

$L_3$ is selected from $R_9$ is selected from H and a $C_4$-$C_8$ alkyl group;

g is an integer in the range of 1-18;

h is 0, 1, or 2.

According to other embodiments of the invention, there is provided a compound, or a pharmaceutically acceptable salt thereof, of formula (III)

(III)

$R_1$ is selected from:

wherein:

$R_3$ and $R_4$ are each independently selected from a $C_1$-$C_6$ alkyl group; alternatively $R_3$ and $R_4$ may join to form 5-6 membered ring containing up to 2 nitrogen (N), optionally substituted with 1-2 substituents selected from a $C_1$-$C_6$ alkyl group;

$R_5$ is selected from $C_1$-$C_6$ alkyl, and cyclopropyl group;

$R_6$ is selected from H, and $C_1$-$C_6$ alkyl group;

a is 1, 2, 3, or 4;

b is 0, or 1;

cis 0, 1, or 2;

c' is 2, 3, or 4;

d is 2;

e is 1;

$E_2$ is selected from —O-$\delta_2$, —OC(O)-$\delta_2$, —OCH$_2$CH$_2$O-$\delta_2$, and —OC(O)(CH$_2$)$_6$C(O)O-$\delta_2$; where $\delta_2$ designates the bond linked to the $R_2$ group;

$R_2$ is selected from or has the formula _(CH$_2$)$_g$_[L$_3$-(CH$_2$)]$_h$_R$_9$, wherein:

$L_1$ and $L_2$ are each a direct bond;

$R_7$ and $R_8$ are each independently selected from $C_4$-$C_{10}$ alkyl group;

f is 0, or 1;

$L_3$ is selected from $R_9$ is selected from H and a $C_4$-$C_8$ alkyl group;

g is an integer in the range of 1-18;

h is 0, 1, or 2.

According to embodiments of the invention, $R_1$ is one of:

7
-continued

8
-continued

In further embodiments, each R₂ is independently:

9
-continued

10
-continued

In still other embodiments of the invention, $E_1$ is selected from:

-continued wherein $\delta_1$ designates the bond linked to the $R_1$ group.

In still other embodiments of the invention, $E_2$ is selected from:

wherein $\delta_2$ designates the bond linked to the $R_2$ group or a pharmaceutically acceptable salt thereof.

According to embodiments of the invention there is provided a compound selected from the group consisting of the compounds listed in Table 1.

| Ref. | Chemical Structure | Exp. pKa |
|---|---|---|
| PNI 76 | | 6.42 |
| PNI 119 | | 7.48 |

-continued

| Ref. | Chemical Structure | Exp. pKa |
|------|-------------------|----------|
| PNI 120 | | 7.71 |
| PNI 121 | | 6.83 |
| PNI 122 | | 7.45 |
| PNI 127 | | 6.46 |

-continued

| Ref. | Chemical Structure | Exp. pKa |
|---|---|---|
| PNI 321 | | 5.62 |
| PNI 325 | | 6.45 |
| PNI 328 | | 6.09 |
| PNI 329 | | 5.88 |

-continued

| Ref. | Chemical Structure | Exp. pKa |
|---|---|---|
| PNI 336 | | 4.57 |
| PNI 342 | | 6.11 |
| PNI 344 | | 6.93 |
| PNI 532 | | 5.97 |

-continued

| Ref. | Chemical Structure | Exp. pKa |
|------|--------------------|----------|
| PNI 534 | | 6.42 |
| PNI 535 | | 4.99 |
| PNI 539 | | 6.60 |
| PNI 538 | | 6.79 |

-continued

| Ref. | Chemical Structure | Exp. pKa |
|------|-------------------|----------|
| PNI 540 | | 5.60 |
| PNI 541 | | 6.46 |
| PNI 573 | | 7.79 |
| PNI 574 | | 6.66 |
| PNI 575 | | 5.51 |
| PNI 576 | | 4.24 |

-continued

| Ref. | Chemical Structure | Exp. pKa |
|---|---|---|
| PNI 577 | | 6.45 |
| PNI 578 | | 5.87 |
| PNI 579 | | 5.32 |
| PNI 580 | | 5.69 |
| PNI 581 | | — |

-continued

| Ref. | Chemical Structure | Exp. pKa |
|---|---|---|
| PNI 582 | | — |
| PNI 583 | | — |
| PNI 369 | | — | or a pharmaceutically acceptable salt thereof.

According to embodiments of the invention, there are also provided the compounds listed in Table 2.

TABLE 2

Representative Compounds

| ID | | Theor. pKa$_1$ |
|---|---|---|
| PNI 326 | | 9.09 |
| PNI 624 | | 8.37 |

TABLE 2-continued

| | Representative Compounds | |
|---|---|---|
| ID | | Theor. pKa$_1$ |
| PNI 625 | | 9.44 |
| PNI 626 | | 9.39 |
| PNI 627 | | 9.44 |
| PNI 628 | | 8.60 |
| PNI 629 | | 9.12 |
| PNI 630 | | 8.26 |
| PNI 631 | | 8.22 |
| PNI 632 | | 8.38 |

TABLE 2-continued

| | Representative Compounds | |
|---|---|---|
| ID | | Theor. pKa$_1$ |
| PNI 633 | | 9.38 |
| PNI 634 | | 9.09 |
| PNI 635 | | 9.12 |
| PNI 636 | | 8.21 |
| PNI 637 | | 8.25 |
| PNI 638 | | 9.39 |

TABLE 2-continued

Representative Compounds

| ID | | Theor. pKa$_1$ |
|---|---|---|
| PNI 639 | | 9.09 |
| PNI 640 | | 9.12 |
| PNI 641 | | 8.22 |
| PNI 642 | | 8.26 |
| PNI 343 | | 9.38 |
| PNI 643 | | 8.21 |

TABLE 2-continued

| | Representative Compounds | |
|---|---|---|
| ID | | Theor. pKa$_1$ |
| PNI 644 | | 8.25 |
| PNI 645 | | 9.12 |
| PNI 646 | | 9.39 |
| PNI 647 | | 8.22 |
| PNI 648 | | 8.26 |
| PNI 649 | | 9.09 |

TABLE 2-continued

Representative Compounds

| ID | | Theor. pKa$_1$ |
|---|---|---|
| PNI 650 | | 9.12 |
| PNI 348 | | 9.12 |
| PNI 349 | | 9.09 |
| PNI 350 | | 9.09 |

TABLE 2-continued

| | Representative Compounds | |
|---|---|---|
| | | Theor. |
| ID | | pKa$_1$ |
| PNI 351 | | 9.15 |
| PNI 352 | | 8.25 |
| PNI 353 | | 8.21 |

TABLE 2-continued

Representative Compounds

| ID | | Theor. pKa$_1$ |
|---|---|---|
| PNI 651 | | 9.39 |
| PNI 652 | | 9.12 |
| PNI 653 | | 9.09 |
| PNI 654 | | 8.26 |

TABLE 2-continued

Representative Compounds

| ID | | Theor. pKa$_1$ |
|---|---|---|
| PNI 655 | | 8.22 |
| PNI 656 | | 9.12 |
| PNI 657 | | 8.21 |

TABLE 2-continued

| | |
|---|---|
| Representative Compounds | |

| ID | Theor. pKa$_1$ |
|---|---|
| PNI 658 | 8.25 |
| PNI 659 | 9.39 |

TABLE 2-continued

| | Representative Compounds | |
|---|---|---|
| ID | | Theor. pKa$_1$ |
| PNI 660 | | 9.09 |
| PNI 661 | | 9.12 |

TABLE 2-continued

| | Representative Compounds | |
|---|---|---|
| ID | | Theor. pKa$_1$ |
| PNI 662 | | 8.22 |
| PNI 663 | | 8.26 |
| PNI 364 | | 8.60 |

TABLE 2-continued

Representative Compounds

| ID | | Theor. pKa$_1$ |
|---|---|---|
| PNI 365 | | 9.39 |
| PNI 368 | | 9.12 |
| PNI 372 | | 8.26 |
| PNI 373 | | 8.22 |
| PNI 665 | | 9.38 |

TABLE 2-continued

Representative Compounds

| ID | | Theor. pKa$_1$ |
|---|---|---|
| PNI 666 | | 9.09 |
| PNI 667 | | 9.12 |
| PNI 668 | | 8.21 |
| PNI 669 | | 8.25 |
| PNI 670 | | 9.38 |

TABLE 2-continued

Representative Compounds

| ID | | Theor. pKa$_1$ |
|---|---|---|
| PNI 671 | | 9.09 |
| PNI 672 | | 9.12 |
| PNI 673 | | 8.21 |
| PNI 674 | | 8.25 |

TABLE 2-continued

Representative Compounds

| ID | | Theor. pKa$_1$ |
|---|---|---|
| PNI 675 | | 9.39 |
| PNI 676 | | 9.09 |
| PNI 677 | | 9.12 |
| PNI 678 | | 8.22 |

TABLE 2-continued

Representative Compounds

| ID | | Theor. pKa$_1$ |
|---|---|---|
| PNI 679 | | 8.26 |
| PNI 340 | | 8.59 |
| PNI 341 | | 9.38 |
| PNI 680 | | 9.09 |
| PNI 681 | | 9.12 |

TABLE 2-continued

Representative Compounds

| ID | | Theor. pKa$_1$ |
|---|---|---|
| PNI 682 | | 8.21 |
| PNI 683 | | 8.25 |
| PNI 684 | | 9.39 |
| PNI 685 | | 9.09 |
| PNI 686 | | 9.12 |
| PNI 687 | | 8.22 |

TABLE 2-continued

| | Representative Compounds | |
|---|---|---|
| ID | | Theor. pKa$_1$ |
| PNI 688 | | 8.26 |
| PNI 383 | | 9.38 |
| PNI 385 | | 9.12 |

TABLE 2-continued

| | Representative Compounds | |
|---|---|---|
| | | Theor.<br>pKa$_1$ |
| ID | | |
| PNI<br>386 | | 9.09 |
| PNI<br>389 | | 8.25 |

TABLE 2-continued

Representative Compounds

| ID | | Theor. pKa$_1$ |
|---|---|---|
| PNI 390 | | 8.21 |
| PNI 689 | | 9.12 |

TABLE 2-continued

Representative Compounds

| ID | | Theor. pKa$_1$ |
|---|---|---|
| PNI 690 | | 9.09 |
| PNI 399 | | 9.38 |

TABLE 2-continued

Representative Compounds

| ID | | Theor. pKa$_1$ |
|---|---|---|
| PNI 401 | | 9.12 |
| PNI 402 | | 9.09 |

TABLE 2-continued

| | Representative Compounds | |
|---|---|---|
| ID | | Theor. pKa$_1$ |
| PNI 405 | | 8.25 |
| PNI 406 | | 8.21 |

TABLE 2-continued

| | Representative Compounds | |
|---|---|---|
| ID | | Theor. pKa$_1$ |
| PNI 691 | | 9.39 |
| PNI 692 | | 9.12 |

TABLE 2-continued

| | Representative Compounds | |
|---|---|---|
| ID | | Theor. pKa$_1$ |
| PNI 693 | | 9.09 |
| PNI 694 | | 8.26 |

TABLE 2-continued

Representative Compounds

| ID | | Theor. pKa$_1$ |
|---|---|---|
| PNI 695 | | 8.22 |
| PNI 696 | | 9.38 |
| | m = 0-5 | |
| PNI 697 | | 9.12 |
| | m = 0-5 | |

TABLE 2-continued

| | Representative Compounds | |
|---|---|---|
| | | Theor. |
| ID | | pKa$_1$ |
| PNI 698 |  m = 0-5 | 9.09 |
| PNI 699 |  m = 0-5 | 8.25 |
| PNI 700 |  m = 0-5 | 8.21 |

TABLE 2-continued

| | Representative Compounds | |
|---|---|---|
| ID | | Theor. pKa$_1$ |
| PNI 701 | m' = 0-4 | 9.39 |
| PNI 702 | m' = 0-4 | 9.12 |
| PNI 703 | m' = 0-4 | 9.09 |

TABLE 2-continued

Representative Compounds

| ID | | Theor. pKa$_1$ |
|---|---|---|
| PNI 704 | | 8.26 | m' = 0-4

| PNI 705 | | 8.22 | m' = 0-4

| PNI 337 | | 8.97 |

| PNI 322 | | 8.82 |

TABLE 2-continued

| | Representative Compounds | |
|---|---|---|
| ID | | Theor. pKa$_1$ |
| PNI 323 | | 8.89 |
| PNI 324 | | 8.62 |
| PNI 331 | | 9.35 |
| PNI 327 | | 9.15 |

TABLE 2-continued

| Representative Compounds | |
| --- | --- |

| ID | | Theor. pKa$_1$ |
| --- | --- | --- |
| PNI 335 | | — |
| PNI 706 | | 8.75 |
| PNI 707 | | 8.93 |
| PNI 708 | | 9.00 |
| PNI 346 | | 8.89 |

TABLE 2-continued

Representative Compounds

| ID | | Theor. pKa$_1$ |
|---|---|---|
| PNI 347 | | 8.62 |
| PNI 355 | | 9.35 |
| PNI 361 | | 8.97 |

TABLE 2-continued

Representative Compounds

| ID | | Theor. pKa$_1$ |
|---|---|---|
| PNI 366 | | 8.89 |
| PNI 367 | | 8.62 |
| PNI 379 | | 8.97 |

TABLE 2-continued

Representative Compounds

| ID | | Theor. pKa$_1$ |
|---|---|---|
| PNI 398 | | 8.59 |
| PNI 400 | | 8.89 |
| PNI 408 | | 9.35 |

TABLE 2-continued

| Representative Compounds | | |
|---|---|---|
| ID | | Theor. pKa$_1$ |
| PNI 709 | | 8.60 |
| | m' = 0-4 | |
| PNI 710 | | 8.89 |
| | m' = 0-4 | |
| PNI 453 | | 9.82 |

TABLE 2-continued

Representative Compounds

| ID | | Theor. pKa₁ |
|---|---|---|
| PNI 456 | | 9.11 |
| PNI 457 | | 9.08 |
| PNI 460 | | 8.23 |

TABLE 2-continued

| | |
|---|---|
| Representative Compounds | |

| ID | | Theor. pKa$_1$ |
|---|---|---|
| PNI 461 | | 8.19 |
| PNI 430 | | 9.38 |
| PNI 433 | | 9.11 |
| PNI 434 | | 9.08 |

TABLE 2-continued

Representative Compounds

| ID | | Theor. pKa$_1$ |
| --- | --- | --- |
| PNI 437 | | 8.23 |
| PNI 438 | | 8.19 |

$_1$Predicted through ChemDraw.

The ionizable lipids of the present invention have asymmetric centers, and occur as racemates, racemic mixtures, individual enantiomers, enantiomeric mixtures, individual diastereomers and as diastereomeric mixtures, with all possible isomers like tautomers and mixtures thereof.

In embodiments of the invention, the experimental pKa of formulated lipid nanoparticles comprising lipids in Table 1 is calculated using the 2-(p-toluidinyl)naphthalene-6-sulfonic acid (TNS) assay. The procedure for the TNS assay is described in Example 25.

There is provided according to embodiments of the invention a lipid mix composition comprising any of the compounds above combined with a structural lipid, a sterol, and a stabilizing agent as well as at least one therapeutic agent.

In embodiments, the structural lipid includes one or more structural lipids selected from the group consisting of DSPC, DSPE, DPPC, DMPC, DOPC, POPC, DOPE and SM. In some embodiments, the structural lipid is DSPC. In other embodiments, the structural lipid is DOPE.

In embodiments, the stabilizing agent includes one or more surfactants and polymer conjugated lipids.

In embodiments, the compound is present at about 10 Mol %-90 Mol %, the structural lipid is present at about 0-50 Mol %, the sterol is present at about 0-45 Mol %, and the stabilizing agent is present at 0-10 Mol %; and the total mol % of components together at 100 mol %.

In further embodiments, the compound is present at about 40 Mol %-60 Mol %, and the structural lipid is present at about 11-40 Mol %; and the total mol % of components together at 100 mol %.

In embodiments, the molar ratio of the compound to the rest of the components is 30 Mol % to 70 Mol %.

In embodiments, the compound is present at 40 Mol %, DSPC is present at 20 Mol %, cholesterol is present at 37.5 Mol %, and polyoxyethylene (10) stearyl ether is present at 2.5 Mol %. In other embodiments, the compound is present at 40 to 47.5 Mol %, DSPC is present at 12.5 Mol %, cholesterol is present at 38.5 to 46 Mol %, and PEG-DMG 2000 is present at 1.5 Mol %. In still other embodiments, the compound is present at 40 to 47.5 Mol %, DOPE is present at 12.5 Mol %, cholesterol is present at 38.5 to 46 Mol %, and PEG-DMG 2000 is present at 1.5 Mol %.

In embodiments, the lipid mix composition further includes a targeting moiety. In embodiments, the sterol is cholesterol. In embodiments, the therapeutic agent includes one or more nucleic acid. In embodiments, the therapeutic agent includes a polypeptide.

In embodiments, the stabilizing agent is selected from the group consisting of PEG-DMG 2000, polyoxyethylene (10) stearyl ether, polyoxyethylene (40) stearate, Polysorbate 80, Polyoxyethylene (4) lauryl ether, Polyoxyethylene (20) stearyl ether, Polyoxyethylene (23) lauryl ether, and D-α-Tocopherol polyethylene glycol 1000 succinate.

There is provided according to an embodiment of the invention a lipid mix composition in the form of a lipid particle.

There is also provided the use of compounds of the invention to prepare a therapeutic agent for administering a therapeutic agent to an ex vivo cell. In further embodiments, the therapeutic agent is a pharmaceutical formulation for use in cancer therapy. In some embodiments, the therapeutic agent is a pharmaceutical formulation for use in T cell modification. In yet other embodiments, the therapeutic agent is a vaccine.

In some embodiments, the therapeutic agent includes a nucleic acid therapeutic. Among these embodiments, the nucleic acid therapeutic is an mRNA, siRNA, miRNA, guide RNA, synthetic guide RNA, an artificial chromosome, circular or linearized DNA, DNA minicircles, or msDNA. In some of these embodiments, the mRNA is a self-replicating RNA molecule.

There is provided, according to embodiments of the invention, the use of the lipid mix compositions for the preparation of a vaccine. In embodiments, the vaccine is directed to the prevention of viral disease. In embodiments, the vaccine is directed against coronavirus infection.

According to embodiments of the invention, there is provided the use of the lipid mix composition described above for use in a therapeutic or cancer vaccine. According to embodiments of the invention, there is provided the use of the lipid mix composition described above for use in protein modulation in vivo or ex vivo.

In embodiments, the mRNA is a self-replicating RNA molecule.

There is provided according to embodiments of the invention the use of the lipid mix compositions described above in the preparation of a pharmaceutical for modulating Human T cells; CAR-T, TCR, gene-editing, or allogenic T cells.

There are further provided embodiments for use of the lipid mix compositions of the invention in the preparation of a pharmaceutical for modulating T cells wherein the T cells are isolated from patients, or for T cells that have been engineered specifically to T cells or allogenic T cells.

In embodiments, the lipid mix composition further includes a polypeptide. In embodiments, the lipid mix composition further includes both a polypeptide and a nucleic acid.

In embodiments, the lipid mix composition further includes a ribonucleoprotein.

There is provided, according to the invention, a compound wherein one of the hydrogens is substituted with a halogen. In embodiments, the halogen is Iodine or fluorine.

There is provided, according to embodiments of the invention, a compound as set out above, or a pharmaceutically acceptable salt thereof, wherein the experimental pKa of nanoparticles is in the range 5.6-7.1.

There is provided, according to embodiments of the invention, a pharmaceutical composition comprising a compound as set out above, and at least one pharmaceutically acceptable carrier or excipient.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

Figure 1:
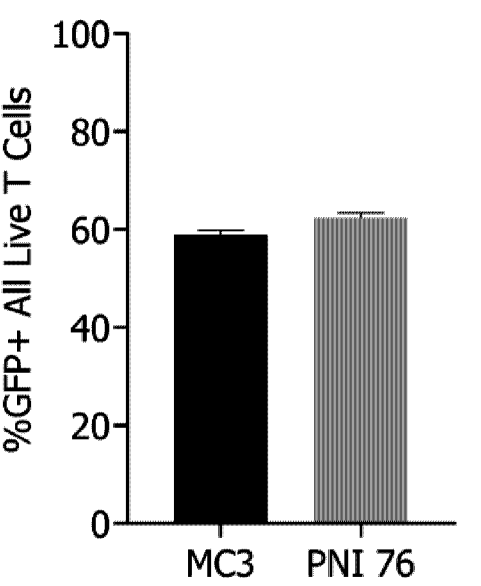
FIG. 1 is a bar graph illustrating relative GFP expression levels in live pan T cells mediated by mRNA Lipid Nanoparticles (LNP) comprising DLin-MC3-DMA, PNI 76 or PNI 121, in a CT10 composition at an N/P ratio of 10, and analyzed for gene expression by flow cytometry 48 hours after treatment.
Figure 1:
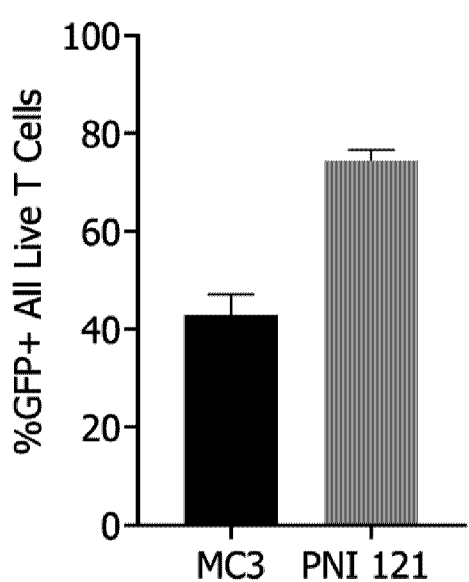

In this disclosure, the word "comprising" is used in a non-limiting sense to mean that items following the word are included, but items not specifically mentioned are not excluded. It will be understood that in embodiments which comprise or may comprise a specified feature or variable or parameter, alternative embodiments may consist, or consist essentially of such features, or variables or parameters. A reference to an element by the indefinite article "a" does not exclude the possibility that more than one of the elements is present, unless the context clearly requires that there be one and only one of the elements.

In this disclosure the recitation of numerical ranges by endpoints includes all numbers subsumed within that range including all whole numbers, all integers and all fractional intermediates (e.g., 1 to 5 includes 1, 1.5, 2, 2.75, 3, 3.80, 4, and 5 etc.). In this disclosure the singular forms an "an", and "the" include plural referents unless the content clearly dictates otherwise. Thus, for example, reference to a composition containing "a compound" includes a mixture of things.

In this disclosure term "or" is generally employed in its sense including "and/or" unless the content clearly dictates otherwise.

"Lipid" refers to structurally diverse group of organic compounds that are fatty acid derivatives or sterols or could be lipid like materials as in lipidoids (example $C_{12}$-200) or polymer conjugated lipids and are characterized by being insoluble in water but soluble in many organic solvents.

"Lipid Mix Compositions". Lipid mix compositions refers to the types of components, ratios of components, and the ratio of the total components to the nucleic acid payloads. For example, a lipid mix composition of 40 Mol % ionizable lipid, 20 Mol % structural lipid, 17.5 Mol % sterol, and 2.5 Mol % Stabilizing agents would be a lipid mix composition.

As used herein, "NIP" is the ratio of moles of the amine groups of ionizable lipids to those of the phosphate groups of nucleic acid. In embodiments of the invention, N/P ratios are from 4 to 10, and most preferred ratios are from N/P 4-12. In one embodiment the N/P ratio is 10. The nucleic acid component is associated with this lipid mix composition to form a lipid nucleic acid particle, or LNP, in a premeditated ratio such as ionizable lipid amine (N) to nucleic acid phosphate ratio (P) of N/P 4, N/P 6, N/P 8, N/P 10, N/P 12 or another relevant particular N/P ratio.

"Lipid Particles". The invention provides lipid particles manufactured from the lipid mix compositions described above. The lipid particle represents the physical organization of the lipid mix composition with the therapeutic agent and among the components. A lipid nanoparticle is a lipid particle. Lipid particles are generally spherical assemblies of lipids, nucleic acid, cholesterol and stabilizing agents. Positive and negative charges, ratios, as well as hydrophilicity and hydrophobicity dictate the physical structure of the lipid particles in terms of size and orientation of components. The structural organization of these lipid particles may lead to an aqueous interior with a minimum bilayer as in liposomes or it may have a solid interior as in solid nucleic acid lipid nanoparticle. There may be phospholipid monolayers or bilayers in single or multiple forms. Lipid particles are between 1 and 1000 µm in size.

"Viability" when referring to cells in vitro, means the ability to continue to grow, divide, and continue to grow and divide, as is normal for the cell type or tissue culture strain. Cell viability is affected by harsh conditions or treatments. Cell viability is critical in ex vivo therapy or parenteral administration.

"Ionizable lipid." The compounds of the invention comprise ionizable lipids. As used herein, the term "ionizable lipid" refers to a lipid that is cationic or becomes ionizable (protonated) as the pH is lowered below the pKa of the ionizable group of the lipid, but is more neutral at higher pH values. At pH values below the pKa, the lipid is then able to associate with negatively charged nucleic acids (e.g., oligonucleotides). As used herein, the term "ionizable lipid" includes lipids that assume a positive charge on pH decrease, and any of a number of lipid species that carry a net positive charge at a selective pH, such as physiological pH.

The ionizable lipid or compound is present in lipid compositions according to other embodiments of the invention, preferably in a ratio of about 30 to about 70 Mol %, in some embodiments, about 30 Mol %, in other embodiments, about 40 Mol %, in other embodiments, about 50 Mol %, in still other embodiments, about 60 Mol % ("Mol %" means the percentage of the total moles that is of a particular component). The term "about" in this paragraph signifies a plus or minus range of 5 Mol %. DODMA, or 1,2-dioleyloxy-3-dimethylaminopropane, is an ionizable lipid, as is DLin-MC3-DMA or (6Z,9Z,28Z,31Z)-Heptatriaconta-6,9, 28,31-tetraen-19-yl 4-(dimethylamino)butanoate.

Lipid particles may be generated from the lipid formulations including the ionizable lipids of the invention.

Structural lipids, also known as "helper lipids" or "neutral lipids" are incorporated into lipid formulations and lipid particles of the invention in some embodiments. The lipid formulations and lipid particles of the invention include one or more structural lipids at about 10 to 40 Mol % of the composition. Suitable structural lipids support the formation of particles during manufacture. Structural lipids refer to any one of a number of lipid species that exist in either in an anionic, uncharged or neutral zwitterionic form at physiological pH. Representative structural lipids include diacylphosphatidylcholines, diacylphosphatidylethanolamines, diacylphosphatidylglycerols, ceramides, sphingomyelins, dihydrosphingomyelins, cephalins, and cerebrosides.

Exemplary structural lipids include zwitterionic lipids, for example, distearoylphosphatidylcholine (DSPC), dioleoylphosphatidylcholine (DOPC), dipalmitoylphosphatidylcholine (DPPC), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearoyl-2-oleoyl-phosphatidyethanol amine (SOPE), and 1,2-dielaidoyl-sn-glycero-3-phophoethanolamine (trans DOPE). In one preferred embodiment, the structural lipid is distearoylphosphatidylcholine (DSPC).

In another embodiment, the structural lipid is any lipid that is negatively charged at physiological pH. These lipids include phosphatidylglycerols such as dioleoylphosphatidylglycerol (DOPG), dipalmitoylphosphatidylglycerol (DPPG), palmitoyloleyolphosphatidylglycerol (POPG), cardiolipin, phosphatidylinositol, diacylphosphatidylserine, diacylphosphatidic acid, and other anionic modifying groups joined to neutral lipids. Other suitable structural lipids include glycolipids (e.g., monosialoganglioside GM1).

Stabilizing agents or Stabilizing agents are included in lipid formulations embodiments to ensure integrity of the mixtures. Stabilizing agents are a class of molecules which disrupt or help form the hydrophobic-hydrophilic interactions among molecules. Suitable Stabilizing agents include, but are not limited to, polysorbate 80 (also known as Tween 80, IUPAC name 2-[2-[3,4-bis(2-hydroxyethoxy)oxolan-2-yl]-2-(2-hydroxyethoxy)ethoxy]ethyl octadec-9-enoate), Myrj52 (Polyoxyethylene (40) stearate), and Brij™ S10 (Polyoxyethylene (10) stearyl ether). Polyethylene glycol conjugated lipids may also be used. The Stabilizing agents may be used alone or in combinations with each other.

In some embodiments, the stabilizing agents comprises about 0.1 to 3 Mol % of the overall lipid mixture. In some embodiments, the Stabilizing agents comprises about 0.5 to 2.5 Mol % of the overall lipid mixture. In some embodiments, the Stabilizing agents is present at greater than 2.5 Mol %. In some embodiments the Stabilizing agents is present at 5 Mol %. In some embodiments the Stabilizing agents is present at 10 Mol %. In some embodiments, the Stabilizing agents is about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, and so forth. In other embodiments, the Stabilizing agents is 2.6-10 Mol % of the lipid mixture. In other embodiments, the Stabilizing agents is present at greater than 10 Mol % of the lipid mixture.

Steroids are included in the preferred lipid mix compositions for certain applications, and lipid particles made therefrom include sterols, such as cholesterol and phytosterol. In the lipid mixes of the invention, cholesterol is present at about 30 to 50 Mol % of the final lipid mix in some embodiments. Alternately cholesterol is present at about 35 to 41 Mol % of the final lipid mix. In other embodiments, sterol is absent.

Nucleic Acids. The lipid mix compositions and lipid particles of the present invention are useful for the systemic or local delivery of nucleic acids. As used herein, the term "nucleic acid therapeutic" (NAT) is meant to include any oligonucleotide or polynucleotide whose delivery into a cell causes a desirable effect. The definition includes diagnostic agents and research reagents which follow the same physical principals afforded by the invention. Fragments containing up to 50 nucleotides are generally termed oligonucleotides, and longer fragments are called polynucleotides. In particular embodiments, oligonucleotides of the present invention are 20-50 nucleotides in length. In embodiments of the invention, oligonucleotides are 996 to 4500 nucleotides in length, as in the case of messenger RNA.

The term "nucleic acid" also refers to ribonucleotides, deoxynucleotides, modified ribonucleotides, modified deoxyribonucleotides, modified phosphate-sugar-backbone oligonucleotides, other nucleotides, nucleotide analogs, and combinations thereof, and can be single stranded, double stranded, or contain portions of both double stranded and single stranded sequence, as appropriate. mRNA can be modified or unmodified, base modified, and may include different type of capping structures, such as Cap1.

As used herein, the terms "polynucleotide" and "oligonucleotide" are used interchangeably and mean single-stranded and double-stranded polymers of nucleotide monomers, including 2'-deoxyribonucleotides (DNA) and ribonucleotides (RNA) linked by internucleotide phosphodiester bond linkages, e.g., 3'-5' and 2'-5', inverted linkages, e.g., 3'-3' and 5'-5', branched structures, or internucleotide analogs. Polynucleotides have associated counter ions, such as H+, NH4+, trialkylammonium, Mg2+, Na+, and the like. A polynucleotide may be composed entirely of deoxyribonucleotides, entirely of ribonucleotides, or chimeric mixtures thereof. Polynucleotides may be comprised of internucleotide, nucleobase and/or sugar analogs.

The term "polypeptides" herein encompasses "oligopeptides" and "proteins" and tertiary and quaternary structures thereof, that are therapeutic agents in some embodiments. An oligopeptide generally consists of from two to twenty amino acids. A polypeptide is a single linear chain of many amino acids of any length held together by amide bonds. A protein consists of one or more and may include structural proteins, energy catalysts, albumin, hemoglobin, immunoglobulins, and enzymes.

A "ribonucleoprotein" is a complex of Cas9 protein and guide RNA in some embodiments. In some embodiments, a ribonucleoprotein is the therapeutic agent referred to in aspects of the invention.

Currently, nucleic acid therapeutics include deoxyribonucleic acid, complementary deoxyribonucleic acid, complete genes, ribonucleic acid, oligonucleotides and ribozymes for gene therapies targeting a variety of diseases, such as cancer, infectious diseases, genetic disorders and neurodegenerative diseases. As described herein, the nucleic acid therapeutic (NAT) is incorporated into lipid particle during its formation with compounds of the invention. More than one nucleic acid therapeutic may be incorporated in this way. They may be derived from natural sources, or more commonly, synthesized or grown in culture. Examples of nucleic acid therapeutics include but are not limited to antisense oligonucleotides, ribozymes, microRNA, mRNA, ribozyme, tRNA, tracrRNA, sgRNA, snRNA, siRNA, shRNA, ncRNA, miRNA, mRNA, pre-condensed DNA, pDNA or an aptamer. Nucleic acid Reagents are used to silence genes (with for example siRNA), express genes (with for example mRNA), edit genomes (with for example CRISPR/Cas9), and reprogram cells for return to the originating organism (for example ex vivo cell therapy to reprogram immune cells for cancer therapy; autologous transfer or allogenic transfer).

The nucleic acid that is present in a lipid particle according to this invention includes any form of nucleic acid that is known. The nucleic acids used herein can be single-stranded DNA or RNA, or double-stranded DNA or RNA, or DNA-RNA hybrids. Examples of double-stranded DNA include structural genes, genes including control and termination regions, and self-replicating systems such as viral or plasmid DNA. Examples of double-stranded RNA include siRNA and other RNA interference reagents. Single-stranded nucleic acids include antisense oligonucleotides, guide RNA, including CRISPR-Cas9 gRNA, ribozymes, microRNA, mRNA, and triplex-forming oligonucleotides. More than one nucleic acid may be incorporated into the lipid particle, for example mRNA and guide RNA together, or different types of each, or in combination with protein.

Plasmid DNA is a preferred nucleic acid to be formulated in embodiments of the invention. A plasmid is a DNA molecule that is separate from chromosomal DNA in a cell, and can replicate independently. Plasmids range from less than 1000 nucleotides to tens of thousands of nucleotides in size. The most common form is small circular, double-stranded DNA. Plasmids can be synthesized and delivered to mammalian cells for therapeutic purposes. Synthetic plasmids are used as vectors in molecular cloning, serving to drive the replication of recombinant DNA sequences within host organisms. Plasmids may be introduced into cells via transformation using physical methods such as electroporation, or chemical means as in the present invention, via lipid particle-enhanced transfection. These lipid mix compositions of the invention have several advantages over physical techniques, including i) high biocompatibility and low toxicity in cell and tissue systems ii) relative ease of manufacture iii) lipophilic matrices are less susceptible to the erosion phenomena observed in polymeric systems iv) an increased circulatory half-life in vivo due to their invisibility from the immune system.

In some cases, a nucleic acid encodes a genetically engineered receptor that specifically binds to a ligand, such as a recombinant receptor, and a molecule involved in a metabolic pathway, or functional portion thereof. Alternately, the molecule involved in a metabolic pathway is a recombinant molecule, including an exogenous entity. A genetically engineered receptor and the molecule involved in a metabolic pathway may be encoded by one nucleic acid or two or more different nucleic acids. In some examples, a first nucleic acid might encode a genetically engineered receptor that specifically binds to a ligand and a second nucleic acid might encode the molecule involved in a metabolic pathway.

"Therapeutic agents" as used herein include nucleic acid therapeutics as herein described, polypeptides as herein described, and polysaccharides, salts, small molecules, inorganic ions and radionuclides.

The lipid particles according to some embodiments of the invention can be characterized by electron microscopy. The particles of the invention having a substantially solid core have an electron dense core as seen by electron microscopy. One such structure is disclosed in U.S. Pat. No. 9,758,795 by Cullis et al. Electron dense is defined such that area-averaged electron density of the interior 50% of the projected area of a solid core particle (as seen in a 2-D cryo EM image) is not less than x % (x=20%, 40%, 60%) of the maximum electron density at the periphery of the particle. Electron density is calculated as the absolute value of the difference in image intensity of the region of interest from the background intensity in a region containing no nanoparticle.

The lipid particles of the invention can be assessed for size using devices that size particles in solution, such as the Malvern™ Zetasizer™. The particles have a mean particle diameter of from about 15 to about 300 nm. Another term for lipid particle is "LNP", which stands for "lipid nanoparticles". In some embodiments, the mean particle diameter is greater than 300 nm. In some embodiments, the lipid particle has a diameter of about 300 nm or less, 250 nm or less, 200 nm or less, 150 nm or less, 100 nm or less, or 50 nm or less. In one embodiment, the lipid particle has a diameter of from about 50 to about 150 nm. Smaller particles generally exhibit increased circulatory lifetime in vivo compared to larger particles. Smaller particles have an increased ability to reach tumor sites than larger nanoparticles. In one embodiment, the lipid particle has a diameter from about 15 to about 50 nm.

Mixing. The lipid particles according to embodiments of the invention can be prepared by standard T-tube mixing techniques, turbulent mixing, trituration mixing, agitation promoting orders self-assembly, or passive mixing of all the elements with self-assembly of elements into nanoparticles. A variety of methods have been developed to formulate lipid nanoparticles (LNP) containing genetic drugs. Suitable methods are disclosed in U.S. Pat. No. 5,753,613 by Ansell, Mui and Hope and U.S. Pat. No. 6,734,171 by Saravolac et al., by way of example. These methods include mixing preformed lipid particles with nucleic acid therapeutic (NAT) in the presence of ethanol or mixing lipid dissolved in ethanol with an aqueous media containing NAT and result in lipid particles with NAT encapsulation efficiencies of 65-99%. Both of these methods rely on the presence of ionizable lipid to achieve encapsulation of NAT and a stabilizing agent to inhibit aggregation and the formation of large structures. The properties of the lipid particle systems produced, including size and NAT encapsulation efficiency, are sensitive to a variety of lipid mix composition parameters such as ionic strength, lipid and ethanol concentration, pH, NAT concentration and mixing rates.1

Microfluidic two-phase droplet techniques have been applied to produce monodisperse polymeric microparticles for drug delivery or to produce large vesicles for the encapsulation of cells, proteins, or other biomolecules. The use of hydrodynamic flow focusing, a common microfluidic technique to provide rapid mixing of reagents, to create monodisperse liposomes of controlled size has been demonstrated.

In general, parameters such as the relative lipid and NAT concentrations at the time of mixing, as well as the mixing rates are difficult to control using current formulation procedures, resulting in variability in the characteristics of NAT produced, both within and between preparations. Automatic micro-mixing instruments such as the NanoAssemblr® instruments (Precision NanoSystems Inc, Vancouver, Canada) enable the rapid and controlled manufacture of nanomedicines (liposomes, lipid nanoparticles, and polymeric nanoparticles). NanoAssemblr® instruments accomplish controlled molecular self-assembly of nanoparticles via microfluidic mixing cartridges that allow millisecond mixing of nanoparticle components at the nanoliter, microlitre, or larger scale with customization or parallelization. Rapid mixing on a small scale allows reproducible control over particle synthesis and quality that is not possible in larger instruments.

Preferred methods incorporate instruments such as the microfluidic mixing devices like the NanoAssemblr® Spark™, Ignite™, Benchtop™ and NanoAssemblr® Blaze™ in order to achieve nearly 100% of the nucleic acid used in the formation process is encapsulated in the particles in one step. In one embodiment, the lipid particles are prepared by a process by which from about 90 to about 100% of the nucleic acid used in the formation process is encapsulated in the particles.

U.S. Pat. Nos. 9,758,795 and 9,943,846, by Cullis et al. describe methods of using small volume mixing technology and novel formulations derived thereby. U.S. Application Pub. No. 20160022580 by Ramsay et al. describes more advanced methods of using small volume mixing technology and products to formulate different materials. U.S. Pat. No. 9,943,846 by Walsh, et al. discloses microfluidic mixers with different paths and wells to elements to be mixed. PCT Publication WO2017117647 by Wild, Leaver and Taylor discloses microfluidic mixers with disposable sterile paths. U.S. Pat. No. 10,076,730 by Wild, Leaver and Taylor discloses bifurcating toroidal micromixing geometries and their application to micromixing. PCT Publication No. WO2018006166 by Chang, Klaassen, Leaver et al. discloses a programmable automated micromixer and mixing chips therefor. US Design Nos. D771834, D771833, D772427, and D803416 by Wild and Leaver, and D800335, D800336 and D812242 by Chang et al., disclose mixing cartridges having microchannels and mixing geometries for mixer instruments sold by Precision NanoSystems Inc.

In embodiments of the invention, devices for biological microfluidic mixing are used to prepare the lipid particles according to embodiments of the invention. The devices include a first and second stream of reagents, which feed into the microfluidic mixer, and lipid particles are collected from the outlet, or emerge into a sterile environment.

The first stream includes a therapeutic agent in a first solvent. Suitable first solvents include solvents in which the therapeutic agents are soluble and that are miscible with the second solvent. Suitable first solvents include aqueous buffers. Representative first solvents include citrate and acetate buffers or other low pH buffers.

The second stream includes lipid mix materials in a second solvent. Suitable second solvents include solvents in which the ionizable lipids according to embodiments of the invention are soluble, and that are miscible with the first solvent. Suitable second solvents include 1,4-dioxane, tetrahydrofuran, acetone, acetonitrile, dimethyl sulfoxide, dimethylformamide, acids, and alcohols. Representative second solvents include aqueous ethanol 90%, or anhydrous ethanol.

In one embodiment of the invention, a suitable device includes one or more microchannels (i.e., a channel having its greatest dimension less than 1 millimeter). In one example, the microchannel has a diameter from about 20 to about 300 μm. In examples, at least one region of the microchannel has a principal flow direction and one or more surfaces having at least one groove or protrusion defined therein, the groove or protrusion having an orientation that forms an angle with the principal direction (e.g., a staggered herringbone mixer), as described in U.S. Pat. No. 9,943,846, or a bifurcating toroidal flow as described in U.S. Pat. No. 10,076,730. To achieve maximal mixing rates, it is advantageous to avoid undue fluidic resistance prior to the mixing region. Thus, one example of a device has non-microfluidic channels having dimensions greater than 1000 μm, to deliver the fluids to a single mixing channel.

Less automated micromixing methods and instruments such as those disclosed in Zhang, S-h et al.,$_2$ and Stroock A et al., U.S. Published Patent Application US20040262223, and Jeffs, L B et al.$_3$, are also useful in creating lipid particle compositions of the invention.

The ionizable lipids of the present invention may be used to deliver a therapeutic agent to a cell, in vitro or in vivo. In particular embodiments, the therapeutic agent is a nucleic acid, which is delivered to a cell using nucleic acid-lipid particles of the present invention. The nucleic acid can be an siRNA, miRNA, an LNA, a plasmid, replicon, an mRNA, a guide RNA, a transposon, or a single gene. In other embodiments, the therapeutic agent to be delivered to a cell or cells is a gene editing technology. Gene editing technologies are a group of technologies that change an organism's DNA, and enable addition, removal, or alteration of genetic material at particular locations in the genome. There are several methods for genome editing including CRISPR-Cas9, (clustered regularly interspaced short palindromic repeats and CRISPR-associated protein 9), TALEN and ZFN$_4$.

In other embodiments, the therapeutic agent is an oligopeptide, polypeptide, or protein which is delivered to a cell using peptide-lipid particles of the present invention. In other embodiments, the therapeutic agent is a mixture of nucleic acid and protein components, such as Cas9. The methods and lipid mix compositions may be readily adapted for the delivery of any suitable therapeutic agent for the treatment of any disease or disorder that would benefit from such treatment.

In certain embodiments, the present invention provides methods for introducing a nucleic acid into a cell (i.e. transfection). Transfection is a technique commonly used in molecular biology for the introduction of nucleic acid therapeutics (or NATs) from the extracellular to the intracellular space for the purpose of transcription, translation and expression of the delivered gene(s). Transfection efficiency is commonly defined as either the i) percentage of cells in the total treated population showing positive expression of the delivered gene, as measured by live or fixed cell imaging (for detection of fluorescent protein), and flow cytometry or ii) the intensity or amount of protein expressed by treated cell(s) as analyzed by live or fixed cell imaging or flow cytometry or iii) using protein quantification techniques such as ELISA, or western blot. These methods may be carried out by contacting the particles or lipid mix compositions of the present invention with the cells for a period of time sufficient for intracellular delivery to occur.

Typical applications include using well known procedures to provide intracellular delivery of siRNA to knock down or silence specific cellular targets in vitro and in vivo. Alternatively, applications include delivery of DNA or mRNA sequences that code for therapeutically useful polypeptides. In this manner, therapy is provided for genetic diseases by supplying deficient or absent gene products. Methods of the present invention may be practiced in vitro, ex vivo, or in vivo. For example, the lipid mix compositions of the present invention can also be used for delivery of nucleic acids to cells in vivo, using methods which are known to those of skill in the art. In another example, the lipid mix compositions of the invention can be used for delivery of nucleic acids to a sample of patient cells that are ex vivo, then are returned to the patient.

The delivery of nucleic acid therapeutics by a lipid particle of the invention is described below.

For in vivo administration, the pharmaceutical compositions are preferably administered parenterally (e.g., intraarticularly, intravenously, intraperitoneally, subcutaneously, intrathecally, intradermally, intratracheally, intraosseous, intramuscularly or intratumorally). In particular embodiments, the pharmaceutical compositions are administered intravenously, intrathecally, or intraperitoneally by a bolus injection. Other routes of administration include topical (skin, eyes, mucus membranes), oral, pulmonary, intranasal, sublingual, rectal, and vaginal.

For ex vivo applications, the pharmaceutical compositions are preferably administered to biological samples that have been removed from the organism, then the cells are washed and restored to the organism. The organism may be a mammal, and in particular may be human. This process is used for cell reprogramming, genetic restoration, immunotherapy, for example.

In one embodiment, the present invention provides a method of modulating the expression of a target polynucleotide or polypeptide. These methods generally comprise contacting a cell with a lipid particle of the present invention that is associated with a nucleic acid capable of modulating the expression of a target polynucleotide or polypeptide. As used herein, the term "modulating" refers to altering the expression of a target polynucleotide or polypeptide. Modulating can mean increasing or enhancing, or it can mean decreasing or reducing.

In related embodiments, the present invention provides a method of treating a disease or disorder characterized by overexpression of a polypeptide in a subject, comprising providing to the subject a pharmaceutical composition of the present invention, wherein the therapeutic agent is selected from an siRNA, a microRNA, an antisense oligonucleotide, and a plasmid capable of expressing an siRNA, a microRNA, or an antisense oligonucleotide, and wherein the siRNA, microRNA, or antisense RNA comprises a polynucleotide that specifically binds to a polynucleotide that encodes the polypeptide, or a complement thereof.

In related embodiments, the present invention provides a method of treating a disease or disorder characterized by under-expression of a polypeptide in a subject, comprising providing to the subject a pharmaceutical composition of the present invention, wherein the therapeutic agent is selected from an mRNA, a self-amplifying RNA (SAM), a self-replicating DNA, or a plasmid, comprises a nucleic acid therapeutic that specifically encodes or expresses the under-expressed polypeptide, or a complement thereof.

In embodiments, the pharmaceutical compositions described herein may be prepared by any method known or hereafter developed in the art of pharmacology. In general, such preparatory methods include the step of associating the active ingredient with an excipient and/or one or more other accessory ingredients.

Methods of Delivery of Biological Active Agents for Treatment of Disease

In one embodiment, the compounds, compositions, and methods and uses of the invention are for delivering a biologically active agent to liver cells (e.g. hepatocytes). In one embodiment, the compounds, compositions, and methods and uses of the invention are for delivering a biologically active agent to a tumor or to tumor cells (e.g. a primary tumor or metastatic cancer cells). In another embodiment, the compounds, compositions, and methods and uses are for delivering a biologically active agent to the skin adipose, muscle and lymph nodes (subcutaneous dosing).

For delivery of a biologically active agent to the liver or liver cells, in one embodiment a composition of the invention is contacted with the liver or liver cells of the via parenteral administration (e.g. intravenous, intramuscular, subcutaneous administration) or local administration (e.g. direct injection, portal vein injection, catheterization, stenting), to facilitate delivery. For delivery of a biologically active agent to the kidney or kidney cells, in one embodiment a composition of the invention is contacted with the kidney or kidney cells of the patient via parenteral administration (e.g. intravenous, intramuscular, subcutaneous administration) or local administration (e.g. direct injection, catheterization, stenting), to facilitate delivery. For delivery of a biologically active agent to a tumor or tumor cells, in one embodiment, a composition of the invention is contacted with the tumor or tumor cells of the patient via parenteral administration (e.g. intravenous, intramuscular, subcutaneous administration) or local administration (e.g. direct injection, catheterization, stenting), to facilitate delivery.

For delivery of a biologically active agent to the CNS or CNS cells), in one embodiment a composition of the invention is contacted with the CNS or CNS cells (e.g. brain cells and/or spinal cord cells) of the patient via parenteral administration (e.g. intravenous, intramuscular, subcutaneous administration) or local administration (e.g. direct injection, catheterization, stenting, osmotic pump administration (e.g. intrathecal or ventricular)), to facilitate delivery. For delivery of a biologically active agent to the Peripheral Nervous System (PNS) or PNS cells, in one embodiment a composition of the invention is contacted with the PNS or PNS cells of the patient via parenteral administration (e.g. intravenous, intramuscular, subcutaneous administration) or local administration (e.g. direct injection), to facilitate delivery. For delivery of a biologically active agent to a lung or lung cells, in one embodiment a composition of the invention is contacted with the lung or lung cells of the patient via parenteral administration (e.g. intravenous, intramuscular, subcutaneous administration) or local administration (e.g. pulmonary administration directly to lung tissues and cells), to facilitate delivery.

For delivery of a biologically active agent to the vasculature or vascular cells, in one embodiment a composition of the invention is contacted with the vasculature or vascular cells of the patient via parenteral administration (e.g. intravenous, intramuscular, subcutaneous administration) or local administration (e.g. clamping, catheterization, stenting), to facilitate delivery.

For delivery of a biologically active agent to the skin or skin cells (e.g. dermis cells and/or follicular cells), in one embodiment a composition of the invention is contacted with the skin or skin cells (e.g. dermis cells and/or follicular cells) of the patient via parenteral administration (e.g. intravenous, intramuscular, subcutaneous administration) or local administration (e.g. direct dermal application, iontophoresis), to facilitate delivery. For delivery of a biologically active agent to an eye or ocular cells (e.g. macula, fovea, cornea, retina), in one embodiment a composition of the invention is contacted with the eye or ocular cells (e.g. macula, fovea, cornea, retina) of the patient via parenteral administration (e.g. intravenous, intramuscular, subcutaneous administration) or local administration (e.g. direct injection, intraocular injection, periocular injection, subretinal, iontophoresis, use of eyedrops, implants), to facilitate delivery. For delivery of a biologically active agent to an ear or cells of the ear (e.g. cells of the inner ear, middle ear and/or outer ear), in one embodiment composition of the invention is contacted with the ear or cells of the ear (e.g. cells of the inner ear, middle ear and/or outer ear) of the patient as is generally known in the art, such as via parenteral administration (e.g. intravenous, intramuscular, subcutaneous administration) or local administration (e.g. direct injection), to facilitate delivery. For delivery of a biologically active agent (e.g. RNA encoding an immunogen) to cells of the immune system (e.g. antigen-presenting cells, including professional antigen presenting cells), in one embodiment composition of the invention is delivered intramuscularly, after which immune cells can infiltrate the delivery site and process delivered RNA and/or process encoded antigen produced by non-immune cells, such as muscle cells. Such immune cells can include macrophages (e.g. bone marrow derived macrophages), dendritic cells (e.g. bone marrow derived plasmacytoid dendritic cells and/or bone marrow derived myeloid dendritic cells), monocytes (e.g. human peripheral blood monocytes), etc. (for example, see WO2012/006372 by Geall, Andy et al.).

Immunization. For immunization purposes, a composition of the invention will generally be prepared as an injectable, a pulmonary or nasal aerosol, or in a delivery device (e.g. syringe, nebulizer, sprayer, inhaler, dermal patch, etc.). This delivery device can be used to administer a pharmaceutical composition to a subject, e.g. to a human, for immunization.

According to the invention, for immunization purposes, in some embodiments, the invention encompasses delivering an RNA that encodes an immunogen. This immunogen elicits an immune response which recognizes the immunogen, to provide immunity against a pathogen, or against an allergen, or against a tumor antigen. Immunizing against disease and/or infection caused by a pathogen is preferred.

The RNA is delivered with a lipid composition of the invention (e.g. formulated as a liposome or LNP). In some embodiments, the invention utilizes LNPs within which immunogen-encoding RNA is encapsulated. Encapsulation within LNPs can protect RNA from RNase digestion. The encapsulation efficiency does not have to be 100%. Presence of external RNA molecules (e.g. on the exterior surface of a liposome or LNP) or "naked" RNA molecules (RNA molecules not associated with a liposome or LNP) is acceptable. Preferably, for a composition comprising lipids and RNA molecules, at least half of the RNA molecules (e.g., at least 50%, at least 55%, at least 60%, at least 65%, at least 70%, at least 75%, at least 80%, at least 85%, at least 90%, or at least 95% of the RNA molecules) are encapsulated in LNPs or complexed LNPs.

Some lipid nanoparticles may comprise a lipid core (e.g., the composition may comprise a mixture of LNPs and nanoparticles with a lipid core). In such cases, the RNA molecules may be encapsulated by LNPs that have an aqueous core, and complexed with the LNPs that have a lipid core by noncovalent interactions (e.g., ionic interactions between negatively charged RNA and cationic lipid). Encapsulation and complexation with LNPs (whether with a lipid or aqueous core) can protect RNA from RNase digestion. The encapsulation/complexation efficiency does not have to be 100%. Presence of "naked" RNA molecules (RNA molecules not associated with a liposome) is acceptable. Preferably, for a composition comprising a population of LNPs and a population of RNA molecules, at least half of the population of RNA molecules (e.g., at least e.g., at least 50%, at least 55%, at least 60%, at least 65%, at least 70%, at least 75%, at least 80%, at least 85%, at least 90%, or at least 95% of the RNA molecules) are either encapsulated in LNPs, or complexed with LNPs.

For delivery of immunogen-coding RNA, the preferred range of LNP diameters is in the range of 60-180 nm, and in more particular embodiments, in the range of 80-160 nm. An LNP can be part of a composition comprising a population of LNPS, and the LNPS within the population can have a range of diameters. For a composition comprising a population of LNPS with different diameters, it is preferred that (I) at least 80% by number of the LNPS have diameters in the range of 60-180 nm, e.g., in the range of 80-160 nm, (ii) the average diameter (by intensity, e.g. Z-average) of the population is ideally in the range of 60-180 nm, e.g., in the range of 80-160 nm; and/or the diameters within the plurality have a polydispersity index<0.2. To obtain LNPS with the desired diameter(s), mixing can be performed using a process in which two feed streams of aqueous RNA solution are combined in a single mixing zone with one stream of an ethanolic lipid solution, all at the same flow rate e.g. in a microfluidic channel. See other description relating to Nano-Assemblr® microfluidic mixers sold by Precision NanoSystems Inc., Vancouver, Canada.

Useful mixtures of lipids, for forming lipid compositions (e.g., LNPS) for immunization uses, comprise: a lipid of formula (I); cholesterol; and a stabilizing agent, such as PEG-DMG. This mixture may also include a neutral zwitterionic lipid, such as DSPC (1,2-diastearoyl-sn-glycero-3-phosphocholine) or DSPE. In certain embodiments, the lipid compositions provided by the invention (such as LNPS) have adjuvant activity, i.e., in the absence of an immunogen, such as protein antigen or a nucleic acid (DNA or RNA), such as a nucleic acid encoding such an antigen.

RNA Molecules. After in vivo administration of an immunization composition, the delivered RNA is released and is translated inside a cell to provide the immunogen in situ. In certain embodiments, the RNA is plus ("+") stranded, so it can be translated by cells without needing any intervening replication steps such as reverse transcription. In certain embodiments, the RNA is a self-replicating RNA. A self-replicating RNA molecule (replicon) can, when delivered to a vertebrate cell even without any proteins, lead to the production of multiple daughter RNAs by transcription from itself (via an antisense copy which it generates from itself). A self-replicating RNA molecule is thus in certain embodiments: a (+) strand molecule that can be directly translated after delivery to a cell, and this translation provides an RNA-dependent RNA polymerase which then produces both antisense and sense transcripts from the delivered RNA. Thus the delivered RNA leads to the production of multiple daughter RNAs. These daughter RNAs, as well as collinear subgenomic transcripts, may be translated themselves to provide in situ expression of an encoded immunogen, or may be transcribed to provide further transcripts with the same sense as the delivered RNA which are translated to provide in situ expression of the immunogen. The overall result of this sequence of transcriptions is an amplification in the number of the introduced replicon RNAs and so the encoded immunogen becomes a major polypeptide product of the host cells.

One suitable system for achieving self-replication is to use an alphavirus-based RNA replicon. These (+) stranded replicons are translated after delivery to a cell to yield a replicase (or replicase-transcriptase). The replicase is translated as a polyprotein which auto cleaves to provide a replication complex which creates genomic (−) strand copies of the (+) strand delivered RNA. These (−) strand transcripts can themselves be transcribed to give further copies of the (+) stranded parent RNA, and also to give a subgenomic transcript which encodes the immunogen. Translation of the subgenomic transcript thus leads to in situ expression of the immunogen by the infected cell. Suitable alphavirus replicons can use a replicase from a sindbis virus, a semliki forest virus, an eastern equine encephalitis virus, a Venezuelan equine encephalitis virus, etc.

Mutant or wild-type virus sequences such as the attenuated TC83 mutant of VEEV can be used in replicons. A preferred self-replicating RNA molecule thus encodes (I) an RNA-dependent RNA polymerase which can transcribe RNA from the self-replicating RNA molecule and (ii) an immunogen. The polymerase can be an alphavirus replicase e.g. comprising one or more of alphavirus proteins nsPI, nsP2, nsP3 and nsP4. Whereas natural alphavirus genomes encode structural virion proteins in addition to the nonstructural replicase polyprotein in particular embodiments, a self-replicating RNA molecule of the invention does not encode alphavirus structural proteins. Thus a particular self-replicating RNA can lead to the production of genomic RNA copies of itself in a cell, but not to the production of RNA-containing virions. The alphavirus structural proteins which are necessary for perpetuation in wild-type viruses are absent from self-replicating RNAs of the invention and their place is taken by gene(s) encoding the immunogen of interest, such that the subgenomic transcript encodes the immunogen rather than the structural alphavirus virion proteins. Thus, a self-replicating RNA molecule useful with the invention may have two open reading frames: one encodes a replicase e.g., the first, (5') open reading frame; the other open reading frame encodes an immunogen, e.g., the second, (3') open reading frame. In some embodiments, the RNA may have additional (e.g. downstream) open reading frames e.g. to encode further immunogens or to encode accessory polypeptides. A self-replicating RNA molecule can have a 5' sequence which is compatible with the encoded replicase. Self-replicating RNA molecules can have various lengths, but they are typically about 5000-25000 nucleotides long e.g. 8000-15000 nucleotides, or 9000-12000 nucleotides. Thus, the RNA is longer than seen in conventional mRNA delivery. In some embodiments, the self-replicating RNA is greater than about 2000 nucleotides, such as greater than about: 9000, 12000, 15000, 18000, 21000, 24000, or more nucleotides long.

An RNA molecule may have a 5' cap (e.g. a 7-methylguanosine). This cap can enhance in vivo translation of the RNA. The 5' nucleotide of an RNA molecule useful with the invention may have a 5' triphosphate group. In a capped RNA, this may be linked to a 7-methylguanosine via a 5'-to-5' bridge. A 5' triphosphate can enhance RIG-I binding and thus promote adjuvant effects. An RNA molecule may have a 3' poly A tail. It may also include a poly A polymerase recognition sequence (e.g. AAUAAA) near its 3' end. An RNA molecule useful with the invention for immunization purposes will typically be single-stranded. Single-stranded RNAs can generally initiate an adjuvant effect by binding to TLR7, TLR8, RNA helicases and/or PKR. RNA delivered in double-stranded form (dsRNA) can bind to TLR3, and this receptor can also be triggered by dsRNA which is formed either during replication of a single-stranded RNA or within the secondary structure of a single-stranded RNA.

RNA molecules for immunization purposes can conveniently be prepared by in vitro transcription (IVT). IVT can use a (cDNA) template created and propagated in plasmid form in bacteria, or created synthetically (for example by gene synthesis and/or polymerase chain-reaction (PCR) engineering methods). As discussed in WO2011/005799 by Hekele, Armin et al., the self-replicating RNA can include (in addition to any 5' cap structure) one or more nucleotides having a modified nucleobase. For instance, a self-replicating RNA can include one or more modified pyrimidine nucleobases, such as pseudouridine and/or 5 methylcytosine residues. In some embodiments, however, the RNA includes no modified nucleobases, and may include no modified nucleotides i.e. all of the nucleotides in the RNA are standard A, C, G and U ribonucleotides (except for any 5' cap structure, which may include a 7' methylguanosine). In other embodiments, the RNA may include a 5' cap comprising a 7' methylguanosine, and the first I, 2 or 3 5' ribonucleotides may be methylated at the 2' position of the ribose. An RNA used with the invention for immunization purposes ideally includes only phosphodiester linkages between nucleosides, but in some embodiments, it contains phosphoramidate, phosphorothioate, and/or methylphosphonate linkages. The invention includes embodiments in which multiple species of RNAs are formulated with a lipid composition provided by the invention, such as two, three, four or more species of RNA, including different classes of RNA (such as mRNA, siRNA, self-replicating RNAs, and combinations thereof).

Immunogen RNA molecules used with the invention for immunization purposes, in some embodiments, encode a polypeptide immunogen. In these embodiments, after administration, the RNA is translated in vivo and the immunogen can elicit an immune response in the recipient. The immunogen may elicit an immune response against a pathogen (e.g. a bacterium, a virus, a fungus or a parasite) but, in some embodiments, it elicits an immune response against an allergen or a tumor antigen. The immune response may comprise an antibody response (usually including IgG) and/or a cell mediated immune response. The polypeptide immunogen will typically elicit an immune response which recognizes the corresponding pathogen (or allergen or tumor) polypeptide, but in some embodiments the polypeptide may act as a mimotope to elicit an immune response which recognizes a saccharide. The immunogen will typically be a surface polypeptide e.g. an adhesin, a hemagglutinin, an envelope glycoprotein, a spike glycoprotein, etc. The RNA molecule can encode a single polypeptide immunogen or multiple polypeptides. Multiple immunogens can be presented as a single polypeptide immunogen (fusion polypeptide) or as separate polypeptides. If immunogens are expressed as separate polypeptides from a replicon, then one or more of these may be provided with an upstream IRES or an additional viral promoter element. Alternatively, multiple immunogens may be expressed from a polyprotein that encodes individual immunogens fused to a short autocatalytic protease (e.g. foot-and-mouth disease virus 2A protein), or as inteins. In certain embodiments, polypeptide immunogens (e.g., I, 2, 3, 4, 5, 6, 7, 8, 9, 10, or more immunogens) may be used, either alone or together with a RNA molecule, such as a self-replicating RNA, encoding one or more immunogens (either the same or different as the polypeptide immunogens).

In some embodiments the immunogen elicits an immune response against Coronavirus, whose immunogens include, but are not limited to, those derived from a SARS CoV-1, SARS-CoV-29 (Roujian Lu, Xiang Zhao, Juan Li, et al. "Genomic Characterisation and Epidemiology of 2019 Novel Coronavirus: Implications for Virus Origins and Receptor Binding" Lancet 2020 Feb. 22; 395(10224):565-574. doi: 10.1016/S0140-6736(20)30251-8. Epub 2020 Jan. 30); *Neisseria meningitidis* for which useful immunogens include, but are not limited to, membrane proteins such as adhesins, autotransporters, toxins, iron acquisition proteins, and factor H binding protein. A combination of three useful polypeptides is disclosed in Giuliani et al. 11(2006) Proc Natl Head Sci USA 103(29):10834-9; *Streptococcus pneumoniae*, for which useful polypeptide immunogens are disclosed in WO2009/016515 by Veja, Masignani et al. including the RrgB pilus subunit, the beta-N-acetylhexosaminidase precursor (spr0057), spr0096, general stress protein GSP-781 (spr2021, SP2216), serine/threonine kinase StkP (SP1732), and pneumococcal surface adhesin PsaA;

Hepatitis viruses, whose immunogens can include hepatitis B virus surface antigen (HBsAg), hepatitis C virus, delta hepatitis virus, hepatitis E virus, or hepatitis G virus antigens; Rhabdovirus: immunogens include, but are not limited to, those derived from a Rhabdovirus, such as a Lyssavirus (e.g. a Rabies virus) and Vesiculovirus (VSV); Caliciviridae, whose immunogens include, but are not limited to, those derived from Calciviridae, such as Norwalk virus (Norovirus), and Norwalk-like Viruses, such as Hawaii Virus and Snow Mountain Virus; avian infectious bronchitis (IBV), Mouse hepatitis virus (MHV), and Porcine transmissible gastroenteritis virus (TGEV); Retrovirus, whose immunogens include those derived from an Oncovirus, a Lentivirus (e.g. HIV-I or HIV-2) or a Spumavirus; Reovirus: immunogens include, but are not limited to, those derived from an Orthoreovirus, a Rotavirus, an Orbivirus, or a Coltivirus; Parvovirus, whose immunogens include those derived from Parvovirus B19; Herpesvirus, whose immunogens include those derived from a human herpesvirus, such as Herpes Simplex Viruses (HSV) (e.g. HSV types I and 2), Varicella-zoster virus (VZV), EpsteinBarr virus (EBV), Cytomegalovirus (CMV), Human Herpesvirus 6 (HHV6), Human Herpesvirus 7 (HHV7), and Human Herpesvirus 8 (HHV8); Papovaviruses, whose immunogens include those derived from Papillomaviruses and Adenovirus.

In some embodiments, the immunogen elicits an immune response against a virus which infects fish.

Fungal immunogens may be derived from Dermatophytres and other opportunistic organisms.

In some embodiments, the immunogen elicits an immune response against a parasite from the *Plasmodium* genus, such as *P. falciparum, P. vivax, P. malariae* or *P. ovale*. Thus the invention may be used for immunizing against malaria. In some embodiments the immunogen elicits an immune response against a parasite from the Caligidae family, particularly those from the *Lepeophtheirus* and *Caligus* genera e.g. sea lice such as *Lepeophtheirus salmonis* or *Caligus rogercresseyi*.

In some embodiments, the immunogen is an mRNA specific to neoantigens in cancer cells or solid tumours.(7) Peng, M., Mo, Y., Wang, Y. et al. Neoantigen vaccine: an emerging tumor immunotherapy. Mol Cancer 18, 128 (2019).

In some embodiments the immunogen is a tumor antigen selected from: (a) cancer-testis antigens such as NY-ESO-I, SSX2, SCPI as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors; (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUMI (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLRFUT; (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT I (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), mammaglobin, alpha-fetoprotein (associated with, e.g., hepatoma), KSA (associated with, e.g., colorectal cancer), gastrin (associated with, e.g., pancreatic and gastric cancer), telomerase catalytic protein, MUC-I (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer); (d) shared antigens, for example, melanoma-melanocyte antigens such as MART-1/Melan A, gp100, MCIR, melanocyte-stimulating hormone receptor, tyrosinase, tyrosinase related protein-I/TRPI and tyrosinase related protein-2/TRP2 (associated with, e.g., melanoma); (e) prostate associated antigens such as PAP, PSA, PSMA, PSH-PI, PSM-PI, PSM-P2, associated with e.g., prostate cancer; (f) immunoglobulin idiotypes (associated with myeloma and B cell lymphomas, for example). In certain embodiments, tumor immunogens include, but are not limited to, p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23HI, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29&BCAA), CA 195, CA 242, CA-50, CAM43, CD68&KPI, CO-029, FGF-5, Ga733 (EpCAM), HTgp-175, M344, MA-50, MG7-Ag, MOV18, NB/70K, NY-CO-I, RCASI, SDCCAG16, TA-90 (Mac-2 binding protein/cyclophilin C-associated protein), TAAL6, TAG72, TLP, TPS, and the like.

Pharmaceutical Compositions for Vaccines. A pharmaceutical composition of the invention, particularly one useful for immunization, may include one or more small molecule immunopotentiators. Pharmaceutical compositions of the invention may include one or more preservatives, such as thiomersal or 2 phenoxyethanol. Mercury-free and preservative-free vaccines can be prepared.

Compositions comprise an immunologically effective amount of the lipid compositions described herein (e.g., LNPS), as well as any other components, as needed. Immunologically effective amount refers to the amount administered to an individual, either in a single dose or as part of a series, is effective for treatment (e.g., prophylactic immune response against a pathogen). This amount varies depending upon the health and physical condition of the individual to be treated, age, the taxonomic group of individual to be treated (e.g. non-human primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The compositions of the invention will generally be expressed in terms of the amount of RNA per dose. A preferred dose has ~100 pg RNA (e.g. from 10-100 pg, such as about 10 pg, 25 pg, 50 pg, 75 pg or 100 pg), but expression can be seen at much lower levels e.g. ~1 pg/dose, ~100 ng/dose, ~10 ng/dose, ~1 ng/dose, etc. The invention also provides a delivery device (e.g. syringe, nebulizer, sprayer, inhaler, dermal patch, etc.) containing a pharmaceutical composition of the invention. This device can be used to administer the composition to a vertebrate subject The LNP-formulated RNA and pharmaceutical compositions described herein are for in vivo use for inducing an immune response against an immunogen of interest. The invention provides a method for inducing an immune response in a vertebrate comprising administering an effective amount of the LNP formulated RNA, or pharmaceutical composition, as described herein. The immune response is preferably protective and preferably involves antibodies and/or cell-mediated immunity. The compositions may be used for both priming and boosting purposes. Alternatively, a prime-boost immunization schedule can be a mix of RNA and the corresponding polypeptide immunogen (e.g., RNA prime, protein boost).

The invention also provides an Lipid Particle (LNP) or pharmaceutical composition for use in inducing an immune response in a vertebrate. The invention also provides the use of a LNP or pharmaceutical composition in the manufacture of a medicament for inducing an immune response in a vertebrate. By inducing an immune response in the vertebrate by these uses and methods, the vertebrate can be protected against various diseases and/or infections e.g. against bacterial and/or viral diseases as discussed above. Vaccines according to the invention may either be prophylactic (i.e. to prevent infection) or therapeutic (i.e. to treat infection), but will typically be prophylactic. The vertebrate is preferably a mammal, such as a human or a large veterinary mammal (e.g. horses, cattle, deer, goats, pigs).

Compositions of the invention will generally be administered directly to a patient. Direct delivery may be accomplished by parenteral injection (e.g. subcutaneously, intraperitoneally, intravenously, intramuscularly, intradermally, or to the interstitial space of a tissue. Alternative delivery routes include rectal, oral (e.g. tablet, spray), buccal, sublingual, vaginal, topical, transdermal or transcutaneous, intranasal, ocular, aural, pulmonary or other mucosal administration. Intradermal and intramuscular administration are two preferred routes. Injection may be via a needle (e.g. a hypodermic needle), but needle-free injection may alternatively be used. A typical intramuscular dose is 0.5 ml. The invention may be used to induce systemic and/or mucosal immunity, preferably to elicit an enhanced systemic and/or mucosal immunity. Dosage can be by a single dose schedule or a multiple dose schedule. Multiple doses may be used in a primary immunization schedule and/or in a booster immunization schedule.

In a multiple dose schedule the various doses may be given by the same or different routes e.g. a parenteral prime and mucosal boost, a mucosal prime and parenteral boost, etc. Multiple doses will typically be administered at least one week apart (e.g. about two weeks, about three weeks, about four weeks, about six weeks, about eight weeks, about ten weeks, about 12 weeks, about 16 weeks, etc.). In one embodiment, multiple doses may be administered approximately six weeks, ten weeks and 14 weeks after birth, e.g. at an age of six weeks, ten weeks and 14 weeks, as often used in the World Health Organization's Expanded Program on Immunization ("EPI"). In an alternative embodiment, two primary doses are administered about two months apart, e.g. about seven, eight or nine weeks apart, followed by one or more booster doses about six months to one year after the second primary dose, e.g. about six, eight, ten or 12 months after the second primary dose. In a further embodiment, three primary doses are administered about two months apart, e.g. about seven, eight or nine weeks apart, followed by one or more booster doses about six months to one year after the third primary dose.

Gene Editing

Gene editing is a group of technologies that can be used to change an organism's DNA by adding, removing, or modifying the genetic sequence at particular locations in the genome. Several approaches to genome editing have been developed, including CRISPR ("clustered regularly interspaced short palindromic repeats") and CRISPR-associated protein 9 ("Cas9"). CRISPR-Cas9 was adapted from a genome editing system in bacteria which capture snippets of DNA from invading viruses and creates DNA segments known as CRISPR arrays. The CRISPR arrays allow the bacteria to "remember" the viruses, so if the viruses attack again, the bacteria produce RNA segments from the CRISPR arrays to target the viruses' DNA. The bacteria then use Cas9 or a similar enzyme to cut the DNA apart, which disables the virus.

The CRISPR-Cas9 system adapted for gene editing works similarly. A small piece of RNA with a short "guide" sequence that attaches (binds) to a specific target sequence of DNA in a genome is generated. The RNA also binds to the Cas9 enzyme. As in bacteria, the modified RNA is used to recognize the DNA sequence, and the Cas9 enzyme cuts the DNA at the targeted location. Although Cas9 is the enzyme that is used most often, other enzymes (for example Cpf1) can also be used. Once the DNA is cut, researchers use the cell's own DNA repair machinery to add or delete pieces of genetic material, or to make changes to the DNA by replacing an existing segment with a customized DNA sequence.

In embodiments of the invention, the new ionizable lipids find use as part of the delivery of, for example, a CRISPER-Cas system chimeric RNA polynucleotide sequence for modifying an organism by manipulation of a target sequence in a genomic locus of interest. Other nucleic acid components might include a guide sequence capable of hybridizing to a target sequence in a eukaryotic cell, a tracr mate sequence and tracr sequence such as that described in WO14204726 A1 by CHZHAN, Fen et al.

CRISPR~Cas9 systems are used in embodiments to target genes in live cells through delivery of the CRISPR-Cas9 system to the appropriate location (i.e. to cells within the organs or tissues of interest). Preferred tissues are within the following organs: kidney; digestive system including the stomach, pancreas, duodenum, ileum and/or colon; lung; brain, in particular neurones, and/or cns in general; eye, including retinal tissue; ear, including the inner ear; skin; muscle; bone; and/or liver in general.

Genes subject to editing using ionizable lipids and compositions according to embodiments of the invention will be those associated with disease.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient may generally be equal to the dosage of the active ingredient which would be administered to a subject and/or a convenient fraction of such a dosage including, but not limited to, one-half or one-third of such a dosage.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1 percent and 99 percent (w/w) of the active ingredient.

Pharmaceutical formulations may additionally comprise a pharmaceutically acceptable excipient, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired.

Various excipients for formulating pharmaceutical compositions and techniques for preparing the composition are known in the art (see Remington: The Science and Practice of Pharmacy, 21st Edition, A. R. Gennaro, Lippincott, Williams and Wilkins, Baltimore, MD, 2006). The use of a conventional excipient medium is contemplated herein, except insofar as any conventional excipient medium may be incompatible with a substance or its derivatives, such as by producing any undesirable biological effect or otherwise interacting in a deleterious manner with any other component(s) of the pharmaceutical composition.

In some embodiments, the particle size of the lipid particles may be increased and/or decreased. The change in particle size may be able to help counter biological reactions such as, but not limited to, inflammation, or may increase the biological effect of the NAT delivered to mammals by changing biodistribution. Size may also be used to determine target tissue, with larger particles being cleared quickly and smaller one reaching different organ systems.

Pharmaceutically acceptable excipients used in the manufacture of pharmaceutical compositions include, but are not limited to, diluents, viscosity reducing agents, antioxidants, solubility enhancers, bulking agents, fillers, surface active agents and/or emulsifiers, preservatives, buffering agents, lubricating agents, and/or oils. Excipients may be available in multiple grades that can be natural, synthetic, or semi-synthetic in origin; animal derived, plant derived, biotechnology derived (recombinant), and/or mineral derived; and solid, semi solid, liquid, or gas. Such excipients may optionally be included in the pharmaceutical formulations of the invention.

In some embodiments, exemplary mRNA, plasmid or other NAT encodes the protein or enzyme selected from human growth hormone, erythropoietin, ATP-binding cassette (ABC) transporter, alpha-1-antitrypsin, acid alpha glucosidase, arylsulfatase A, carboxypeptidase N, a-galactosidase A, alpha-L-iduronidase, iduronate-2-sulfatase, iduronate sulfatase, N-acetylglucosamine-1-phosphate transferase, N-acetylglucosaminidase, alpha-glucosaminide acetyltransferase, N-acetylglucosamine 6-sulfatase, N-acetylgalactosamine-4-sulfatase, beta-glucosidase, galactose-6-sulfate sulfatase, beta-galactosidase, beta-glucuronidase, BMPER-2, glucocerebrosidase, heparan sulfamidase, heparin-N-sulfatase, lysosomal acid lipase, hyaluronidase, galactocerebrosidase, ornithine transcarbamylase (OTC), carbamoyl-phosphate synthetase 1 (CPS 1), argininosuccinate synthetase (ASS 1), argininosuccinate lyase (ASL), arginase 1 (ARGI), cystic fibrosis transmembrane conductance regulator (CFTR), survival motor neuron (SMN), Factor VIII, Factor IX, transcription activator-like effector nucleases like TALENS, zinc-finger nucleases (ZFNs), (CRISPR)-associated protein 9 (Cas9), and self-replicating RNA, and low density lipoprotein receptors (LDLR).

Other plasmid or nucleic acids can be applied to cell-based system using this invention in the context of a research or screening platform. These include the introduction of genetic material for the purpose of inducing specific physiological or functional changes in cells, such as in the process of reprogramming for the generation of induced pluripotent stem cells. In this case, specific genes (known as Yamanaka factors) are introduced to patient-derived somatic cells, which trigger a reversal of the cell to a stem cell-like state. These enable the cells to divide indefinitely and become pluripotent (able to differentiate to many other downstream cell types) which can be used for both research and clinical applications. These and similar genetic manipulation steps can be enhanced by the lipid particles of the invention to improve the efficiency of processes commonly used when working with induced stem cells.

The following is a description of representative lipid particles prepared with nucleic acid, how they are made, evidence of their advantages, and methods for using them to deliver therapeutic benefits.

Lipid mix composition of lipid particles were generated by rapidly mixing lipid-ethanol solution with an aqueous buffer inside a microfluidic mixer designed to induce chaotic advection and provide a controlled mixing environment at intermediate Reynolds number (24<Re<1000). The microfluidic channels have herringbone features or are configured in a manner as shown in PCT Publication WO2017117647 by Wild, Leaver and Taylor.

Particle sizes and "polydispersity index" (PDI) of the lipid particle were measured by dynamic light scattering (DLS). PDI indicates the width of the particle distribution. This is a parameter calculated from a cumulative analysis of the (DLS)-measured intensity autocorrelation function assuming a single particle size mode and a single exponential fit to the autocorrelation function. From a biophysical point of view, a PDI below 0.1 indicates that the sample is monodisperse. The particles produced by mechanical micromixers such as the NanoAssemblr® Spark™ and NanoAssemblr® Benchtop (Precision NanoSystems Inc.) are substantially homogeneous in size assuming all other variables are neutral. A lower PDI indicates a more homogenous population of lipid particles. The Spark™ instrument is used in a screening setting to identify the lead compositions. Once the composition is selected, the lipid particle can be fine-tuned using the NanoAssemblr® Benchtop. Once the process parameters Flow Rate Ratio and Total Flow Rate is identified for the specific nanoparticle composition, the nanoparticle technology can be scaled up using the same process parameter values.

In preferred embodiments, the nucleic acid is a plasmid composed of double stranded deoxyribonucleic acid. A plasmid is a genetic structure that resides in a cell's cytoplasm (as opposed to the nucleic where the traditional cellular genetics reside) cell that can replicate independently of the chromosomes, typically a small circular DNA strand. Plasmids can also be used to create novel cellular or animal models for medical research. Plasmids are an important tool in molecular biology and as an emerging therapeutic due to their i) ease of manipulation and isolation ii) ability to self-replicate for scaled-up manufacturing iii) long term stability iv) functionality in a range of organisms and applications. An engineered plasmid will have, in addition to a replication origin (or not, depending on the intended use), restriction enzyme recognition sites to allow breaking the circle to introduce new genetic material, and a selective marker such as an antibiotic resistance gene. A plasmid may be from about 1000 bp to about 20 kilobase pairs (bp).

As used herein, the term "about" is defined as meaning 10% plus or minus the recited number. It is used to signify that the desired target concentration might be, for example, 40 Mol %, but that through mixing inconsistencies, the actual percentage might differ by +1-5 Mol %.

As used herein, the term "substantially" is defined as being 5% plus or minus the recited number. It is used to signify that the desired target concentration might be, for example, 40 Mol %, but that through mixing inconsistencies, the actual percentage might differ by +/−5 Mol %.

As used herein, the term "nucleic acid" is defined as a substance intended to have a direct effect in the diagnosis, cure, mitigation, treatment or prevention of disease, or to have direct effect in restoring, correcting or modifying physiological functions, or to act as a research reagent. In preferred embodiments, the nucleic acid is an oligonucleotide. In preferred embodiments, the therapeutic agent is a nucleic acid therapeutic, such as an RNA polynucleotide. In preferred embodiments, the therapeutic agent is double stranded circular DNA (plasmid), linearized plasmid DNA, minicircles or msDNA (multicopy single stranded DNA).

In this disclosure, the word "comprising" is used in a non-limiting sense to mean that items following the word are included, but items not specifically mentioned are not excluded. It will be understood that in embodiments which comprise or may comprise a specified feature or variable or parameter, alternative embodiments may consist, or consist essentially of such features, or variables or parameters. A reference to an element by the indefinite article "a" does not exclude the possibility that more than one of the elements is present, unless the context clearly requires that there be one and only one of the elements.

In this disclosure, "transfection" means the transfer of nucleic acid into cells for the purpose of inducing the expression of a specific gene(s) of interest in both laboratory and clinical settings. It typically includes an ionizable lipid to associate with nucleic acid, and structural lipids. LIPO-FECTIN™ and LIPOFECTAMINE™ are established commercial transfecting reagents sold by ThermoFisher Scientific. These research reagents contain permanently cationic lipid/s and are not suitable for use in or ex vivo.

In this disclosure the recitation of numerical ranges by endpoints includes all numbers subsumed within that range including all whole numbers, all integers and all fractional intermediates (e.g., 1 to 5 includes 1, 1.5, 2, 2.75, 3, 3.80, 4, and 5 etc.). In this disclosure the singular forms an "an", and "the" include plural referents unless the content clearly dictates otherwise. Thus, for example, reference to a composition containing "a compound" includes a mixture of two or more compounds. In this disclosure term "or" is generally employed in its sense including "and/or" unless the content clearly dictates otherwise.

"Stabilizing agent" or "Stabilizer" is a term used to identify the agent that is added to the ionizable lipid, the structural lipid, and the sterol that form the lipid composition according to the invention. Stabilizing agents are non-ionic as herein described. Examples of non-ionic Stabilizing agents include: Polysorbates (Tweens), Brij™ S20 (polyoxyethylene (20) stearyl ether), Brij™35 (Polyoxyethylene lauryl ether, Polyethyleneglycol lauryl ether), Brij™S10 (Polyethylene glycol octadecyl ether, Polyoxyethylene (10) stearyl ether), Myrj™52 (polyoxyethylene (40) stearate). Stabilizing agents combinations are also used in some embodiments, including polysorbate and maltoside, Alkyl polyglycosides (TBD), PEG-conjugated lipids or other polymer conjugated lipids.

"Alkyl" means a straight chain or branched, noncyclic or cyclic, saturated aliphatic hydrocarbon containing from 1 to 24 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

"Alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

The term "acyl" refers to hydrogen, alkyl, partially saturated or fully saturated cycloalkyl, partially saturated or fully saturated heterocycle, aryl, and heteroaryl substituted carbonyl groups. For example, acyl includes groups such as $(C_1-C_{20})$alkanoyl (e.g., formyl, acetyl, propionyl, butyryl, valeryl, caproyl, t-butylacetyl, etc.), $(C_3-C_{20})$cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl,1H-pyrroyl-2-carbonyl, 1H-pyrroyl-3-carbonyl, benzo[b]thiophenyl-2-carbonyl, etc.).

The term "aryl" refers to an aromatic monocyclic, bicyclic, or tricyclic hydrocarbon ring system, wherein any ring atom can be substituted. Examples of aryl moieties include, but are not limited to, phenyl, naphthyl, anthracenyl, and pyrenyl.

"Heterocycle" means a 3- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles include heteroaryls as defined below. Heterocycles include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein any ring atom can be substituted. The heteroaryl groups herein described may also contain fused rings that share a common carbon-carbon bond. The term "alkylheterocyle" refers to a heteroaryl wherein at least one of the ring atoms is substituted with alkyl, alkenyl or alkynyl The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, oxo, thioxy, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted. Exemplary substituents include amino, alkylamino, dialkylamino, and cyclic amino compounds.

"Halogen" means fluoro-, chloro-, bromo- and iodo-substituents.

The terms "alkylamine" and "dialkylamine" refer to —NH(alkyl) and —N(alkyl)$_2$ radicals respectively. The term "hydroxyalkyl" means -alkyl-OH radical. The term "alkyl-heterocycle" refers to an alkyl where at least one methylene has been replaced by a heterocycle.

In some embodiments, the methods of the invention may require the use of protecting groups. Protecting group methodology is well known to those skilled in the art (see, for example, Protective Groups in Organic Synthesis, Green, T. W. et. al., Wiley-Interscience, New York City, 1999). Briefly, protecting groups within the context of this invention are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

Additionally, the invention may be described as in formula (I), (II), or (III); A compound, or a pharmaceutically acceptable salt thereof, as shown in formula (I), (II), or (III), wherein the experimental pKa of nanoparticles is in the range 5.8-7.1.

The compounds of the present invention may be prepared by known organic synthesis techniques, including the methods described in more detail in the Examples. Scope of the invention may include various salts, hydrates, and solvates of the compound. Compounds of the invention can also include various pharmaceutically acceptable isotopes. Compounds of the invention include various pharmaceutically acceptable substitutions, such as fluorinated or iodinated derivatives.

Compounds of this invention can be synthesized using various possible synthetic routes, which can be readily selected by one of skill in the art of organic synthesis.

The phrase 'pharmaceutically acceptable' is employed to describe compounds, materials, compositions, nanoparticle suspensions in solutions or any other form such as lyophilized, powder form, aerosol, or other dosage forms within the scope of sound medical judgement suitable for use in contact with human and animal tissues or cells with a reasonable benefit/risk ratio. Benefit/risk ratio may come from protecting the therapeutic entities such as small molecules, nucleic acids, peptides, or proteins from degradation in biological milieu in vivo or ex vivo.

Compounds may also be evaluated in one or more preclinical models known for those schooled in the art to show the therapeutic validation of a pharmaceutically viable cargo such as NAT, peptides and proteins. These include, but are not limited to rodent models and non-human primates.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims.

Accordingly, the drawings and the description are to be regarded as illustrative in nature, and not as restrictive and the full scope of the subject matter is set forth in the claims.

EXAMPLES

General Considerations:

All solvents and reagents were commercial products and used as such unless noted otherwise. Temperatures are given in degrees Celsius. The structure of final starting materials, intermediates and final products is confirmed by standard analytical methods, e.g., MS or NMR. Unless otherwise stated, $_1$H NMR spectra were recorded in CDCl$_3$ solutions, at 298 K using AVANCE NEO NanoBay Bruker 400 MHz NMR spectrometer. Chemical shifts are reported in parts per million (ppm) relative to TMS (0.00) and coupling constants, J, are in Hertz (Hz) for $_1$H. The following abbreviations are used to denote signal patterns: s=singlet, d=doublet, t=triplet, q=quartet, p=pentet, m=multiplet, dd=doublet of doublets, br s=broad singlet, dt=doublet of triplets. Unless otherwise stated, column purification was carried out using Isolera™ Prime using an appropriate eluent of isocratic or gradient composition.

All final compounds were determined to be greater than 85% pure via analysis by reverse phase UHPLC-MS (Retention times RT in minutes) using Shimadzu Nexera UHPLC instrument with DAD and ELSD and Acquity Peptide BEH C18 2.1 mm×50 mm, 1.7 μm column and a gradient with 10 mM ammonium bicarbonate in water (A) and Acetonitrile: Methanol 80:20 ratio (B). The gradient study ran at linearly 80 to 100% B over 12 minutes at 0.8 mL/min. Injection volume was 2 μL and the column temperature was ambient. Detection was based on multimode with electrospray and atmospheric pressure chemical ionization (ESI and APCI) in positive and negative mode using Shimadzu 2020 Single Quad mass spectrometer (Science Park, Singapore) and evaporative light scattering detector (ELSD) except PNI 76, 119, 120, 121, 122 and 127. Low resolution MS data of PNI 76, 119, 120, 121, 122 and 127 were recorded using a Bruker micrOTOF™ Time-of-Flight mass spectrometer with a positive electrospray ionization source on an Agilent™ 1200 H PLC. Sodium formate was used as a reference. Samples were introduced by flow injection via HPLC with acetonitrile/water (0.1% formic acid) as mobile phase.

ABBREVIATIONS

ACD-A=Anticoagulant Citrate Dextrose Solution
AcOH=acetic acid
aq.=aqueous
cat.=catalytic
DCM=dichloromethane
DIPEA=N,N-Diisopropylethylamine
DMAP=4-dimethylaminopyridine
DMF=N,N-dimethylformamide
EDCl=1-ethyl-3-(3-dimethylaminopropyl)carbodiimide
EPO=erythropoietin
ESI=electrospray ionization
EtOAc=ethyl acetate
Et$_2$O=diethyl ether
g=gram
h=hour
Hz=hertz
K=Kelvin,
MC3=DLin-MC3-DMA
MeOH=methanol
mg=milligram MHz=megahertz
min=minute (s)
mL=milliliter (s)
mmol=millimole (s)
MS=mass spectroscopy
NMR=nuclear magnetic resonance
Pet.=petroleum
ppm=parts per million
Satd.=saturated
TFA=trifluoroacetic acid
THF=tetrahydrofuran
TLC=thin layer chromatography
TMS=Tetramethylsilane
TNS=6-(p-Toluidino)-2-naphthalenesulfonic acid sodium
    salt
UHPLC=Ultra High performance liquid chromatography
° C.=Degree Celsius

Example 1. Synthesis of 1,4-anhydroxylitol (1)

Scheme 1. Synthesis of compound 1

$$\text{(±)-Xylitol} \xrightarrow{\text{10\% aq. H}_2\text{SO}_4}$$

(±)-Xylitol

-continued (±)-1

Into a 250 mL single necked round bottomed flask fitted with a reflux condenser, (±)-Xylitol (20.0 g, 131.4 mmol) was added and dissolved in 10% aq. $H_2SO_4$ (10 mL) and a is fitted to it. The reaction mixture was heated at 135° C. for 6 h. After completion of the reaction as indicated by TLC, the reaction mixture was quenched with aqueous saturated $NaHCO_3$ solution and lyophilized to afford crude (±)-1,4-anhdyroxylitol (1, 14.5 g, 23.86 mmol, 82.0% yield) as a thick colorless oil, which was used for the next step without further purification. $_1$H (400 MHz, MeOD) δ 4.16-4.03 (m, 4H), 3.82 (dd, 1H, J=12.0, 4.0), 3.74 (dd, 1H, J=12.0, 4.0), 3.66 (d, 1H, J=8.0).

Example 2

Synthesis of PNI 121, 122, 127, 321, 325, 328, 329, 336, 538, 539 and 540

Scheme 2. General route for synthesis of PNI 121, 122, 127, 321, 325, 328, 329, 336, 538, 539 and 540

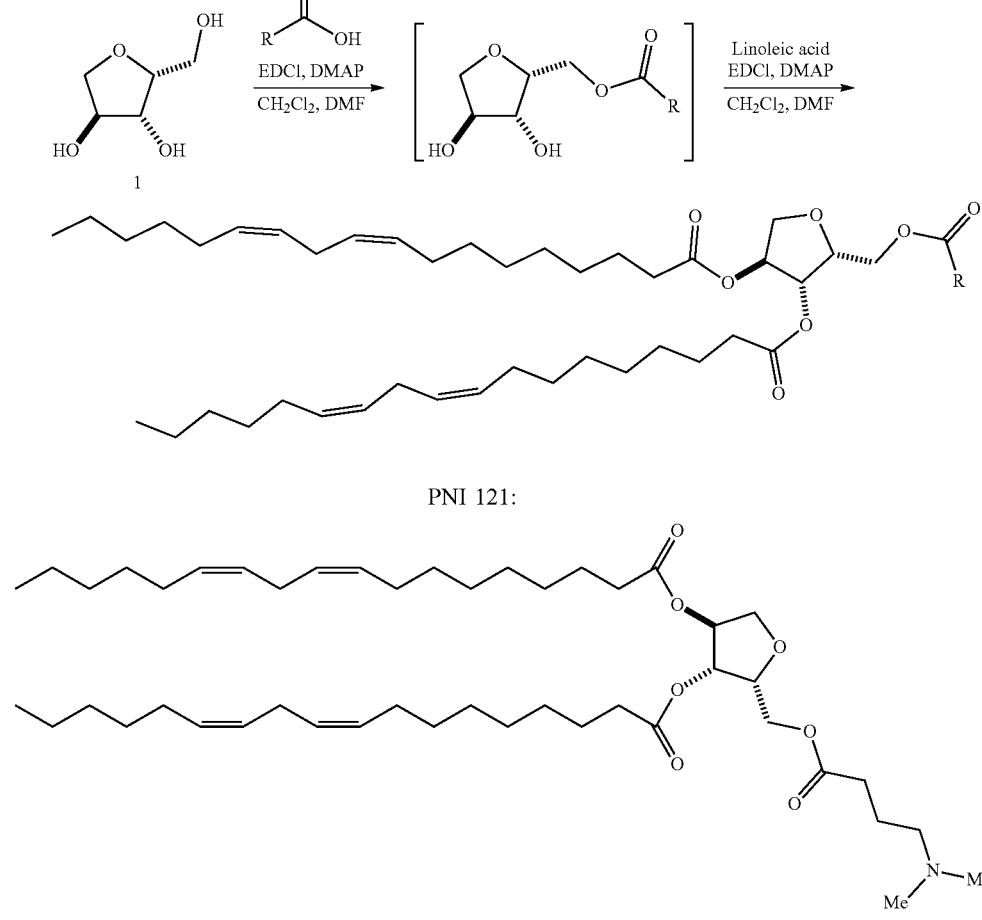

$$1 \xrightarrow[\text{CH}_2\text{Cl}_2, \text{DMF}]{\substack{\text{R}-\text{C(O)OH}\\ \text{EDCl, DMAP}}} \left[ \quad \right] \xrightarrow[\text{CH}_2\text{Cl}_2, \text{DMF}]{\substack{\text{Linoleic acid}\\ \text{EDCl, DMAP}}}$$

PNI 121:

To a solution of (±)-1 (1.25 g, 9.3 mmol) in dry DMF (15 mL), DMAP (cat.) was added followed by addition of a solution of 4-(dimethylamino)butanoic acid hydrochloride (1.56 g, 9.3 mmol) in dry DMF (10 mL) under $N_2$ atmosphere. DCM (25 mL) was added to the reaction mixture. Finally, solid EDCl hydrochloride (3.56 g, 18.6 mmol) was added to the reaction mixture and was stirred at room temperature for 4 h. TLC analysis of the reaction mixture shows complete consumption of (±)-1. Further, DMAP (cat.) was added to the reaction mixture followed by addition of linoleic acid (7.2 mL, 23.3 mmol) and EDCl hydrochloride (7.13 g, 37.2 mmol). Next, dry DMF (20 mL) and dry $CH_2Cl_2$ (10 mL) was added and the reaction mixture was stirred overnight at room temperature. The reaction mixture was concentrated over rotary evaporator, diluted with EtOAc (50 mL) and washed with water (3×20 mL). Organic layer was washed with brine, dried over anhyd. $Na_2SO_4$ and evaporated to dryness over rotary evaporator to provide crude mixture which was purified by silica gel column chromatography using 5% MeOH/$CH_2Cl_2$ as the eluent. PNI 121 was obtained as colorless oil (590 mg, 0.76 mmol) in 8% yield. $_1H$ (500 MHz, CDCl$_3$) δ 5.42-5.31 (m, 9H), 5.13-5.11 (m, 1H), 4.33-4.23 (m, 3H), 4.20-4.16 (m, 1H), 3.76 (dd, 1H, J=15.0 Hz, 5.0 Hz), 2.78 (apparent t, 4H, J=5.0 Hz), 2.40-2.32 (m, 8H), 2.26 (s, 6H), 2.06 (q, 8H, J=15.0 Hz, 5.0 Hz), 1.85-1.79 (m, 2H), 1.65-1.60 (m, 4H), 1.39-1.26 (m, 28H), 0.90 (apparent t, 6H, J=7.5 Hz). Molecular weight for $C_{47}H_{82}NO_7$ [M+H]$_+$ Calculated 772.6091. Found 772.6126. PNI 122:

To a solution of (±)-1 (1.25 g, 9.3 mmol) in dry DMF (15 mL), DMAP (cat.) was added followed by addition of a solution of 5-(dimethylamino)pentanoic acid hydrochloride (1.68 g, 9.3 mmol) in dry DMF (10 mL) under $N_2$ atmosphere. DCM (25 mL) was added to the reaction mixture. Finally, solid EDCl hydrochloride (3.56 g, 18.6 mmol) was added and reaction was stirred at room temperature for 4 h. TLC analysis of the reaction mixture shows complete consumption of (±)-1. Further, DMAP (cat.) was added to the reaction mixture followed by addition of linoleic acid (7.2 mL, 23.25 mmol) and EDCl hydrochloride (7.13 g, 37.2 mmol). Next, dry DMF (20 mL) and dry DCM (10 mL) was added and the reaction mixture was stirred overnight at room temperature. The reaction mixture was concentrated over rotary evaporator, diluted with ethyl acetate (50 mL) and washed with water (3×20 mL). Organic layer was washed with brine, dried over anhyd. $Na_2SO_4$ and evaporated to dryness over rotary evaporator to provide crude mixture which was purified by silica gel column chromatography using 5% MeOH/DCM as the eluent. PNI 122 was obtained as colorless oil (912 mg, 1.16 mmol) in 12% yield. $_1H$ (500 MHz, CDCl$_3$) δ 5.42-5.31 (m, 9H), 5.13-5.11 (m, 1H), 4.35-4.23 (m, 3H), 4.17 (dd, 1H, J=10.0 Hz, 5.0 Hz), 3.76 (dd, 1H, J=10.0 Hz, 5.0 Hz), 2.78 (apparent t, 4H, J=5.0 Hz), 2.39-2.30 (m, 8H), 2.25 (s, 6H), 2.06 (q, 8H, J=15.0 Hz, 5.0 Hz), 1.69-1.60 (m, 6H), 1.52 (p, 2H, J=7.5 Hz), 1.39-1.26 (m, 28H), 0.90 (apparent t, 6H, J=7.5 Hz). Molecular weight for $C_{48}H_{84}NO_7$ [M+H]$_+$ Calculated 786.6248. Found 786.6365.

PNI 127:

To a solution of (±)-1 (200 mg, 1.49 mmol) in dry DMF (2 mL), DMAP (cat.) was added followed by addition of a solution of 1,4-dimethylpiperidine-4-carboxylic acid hydrochloride (289 mg, 1.49 mmol) in dry DMF (3 mL) under $N_2$ atmosphere at room temperature. DCM (5 mL) was added to the reaction mixture. Finally, solid EDCl hydrochloride (571 mg, 2.98 mmol) was added and reaction was stirred overnight. TLC analysis of the reaction mixture shows complete consumption of (±)-1. DMAP (cat.) was added to the reaction mixture followed by addition of linoleic acid (1.2 mL, 3.73 mmol) and EDCl hydrochloride (1.14 g, 5.96 mmol). Next, dry DMF (5 mL) and dry DCM (5 mL) was added and the reaction mixture was stirred overnight at room temperature. The reaction mixture was concentrated over rotary evaporator, diluted with EtOAc (20 mL) and washed with water (3×10 mL). Organic layer was washed with brine, dried over anhyd. $Na_2SO_4$ and evaporated to dryness over rotary evaporator to provide crude mixture which was purified by silica gel column chromatography using 5% MeOH/DCM as the eluent. PNI 127 was obtained as colorless oil (225 mg, 0.28 mmol) in 19% yield. $_1$H (500 MHz, CDCl$_3$) δ 5.42-5.31 (m, 9H), 5.14-5.12 (m, 1H), 4.34-4.27 (m, 2H), 4.24 (apparent d, 2H, J=5.0 Hz), 3.76 (dd, 1H, J=15.0 Hz, 5.0 Hz), 2.78 (apparent t, 4H, J=5.0 Hz), 2.69 (brs, 2H), 2.36-2.26 (m, 8H), 2.20-2.12 (m, 3H), 2.06 (q, 8H, J=15.0 Hz, 5.0 Hz), 1.66-1.60 (m, 6H), 1.38-1.29 (m, 28H), 1.22 (s, 3H), 0.90 (apparent t, 6H, J=7.5 Hz). Molecular weight for $C_{49}H_{84}NO_7$ [M+H]$_+$ Calculated 798.6248. Found 798.6157.

PNI 321:

g, 0.373 mmol) and a solution of 3-(Dimethylamino)propionic acid hydrochloride (0.573 g, 3.73 mmol) in dry DMF (2.5 mL).

To this stirred solution, dry DCM (10 mL) was added, followed by the addition of EDCl hydrochloride (1.429 g, 7.46 mmol) and DIPEA (1.628 ml, 9.32 mmol). The reaction mixture was stirred at room temperature for 4 h and found that 1 disappeared completely as indicated by TLC. DMAP (0.091 g, 0.746 mmol) was added to the reaction mixture followed by the addition of linoleic acid (2.61 g, 9.32 mmol) in dry DMF (7.5 mL). Then EDCl hydrochloride (2.86 g, 14.91 mmol) and DIPEA (3.26 ml, 18.64 mmol) were added followed by the addition of dry DCM (10 mL). The reaction mixture was stirred at room temperature for 16 h. Upon completion of the reaction as indicated by TLC, the solvent was evaporated under reduced pressure. The residue was dissolved in EtOAc (60 mL) and washed with water (2×50 mL). The aq. layer was extracted with EtOAc (2×30 mL) and the combined organic layers were washed with brine (2×50 mL). The organic layer was separated, dried over anhydrous $Na_2SO_4$, filtered and concentrated. The crude product was purified by silica gel (100-200 mesh) column chromatography (Isolera™) using 80% EtOAc in Pet. Ether to give PNI 321 (0.265 g, 0.327 mmol, 8.78% yield) as light-yellow oil. $_1$H (400 MHz, CDCl$_3$) δ 5.42-5.30 (m, 9H), 5.15-5.11 (m, 1H), 4.34-4.16 (m, 4H), 3.76 (dd, 1H, J=8.0, 4.0), 2.78 (app t, 4H, J=6.0), 2.63 (app t, 2H, J=6.0), 2.52 (app t, 2H, J=6.0), 2.36-2.31 (m, 4H), 2.25 (s, 6H), 2.06 (q, 8H, J=8.0), 1.64-1.61 (m, 4H), 1.38-1.26 (m, 28H), 0.91-

To a stirred solution of (±)-1,4-anhydroxylitol (1, 0.50 g, 3.73 mmol) in dry DMF (10 mL) was added DMAP (0.046

0.88 (m, 6H). RT=3.61 min. 93.7% purity. ESI-MS: m/z=759 [M+H]$_+$ for $C_{46}H_{80}NO_7$.

PNI 325:

To a well-stirred solution of (±)-1,4-anhdyroxylitol (1, 700 mg, 5.22 mmol) and DMAP (63.8 mg, 0.522 mmol) in dry DMF (5 mL) at 25° C., was added a solution of 1-methylpiperidine-4-carboxylic acid (747 mg, 5.22 mmol) in dry DMF (2.5 mL) under nitrogen atmosphere. Then, dry DCM (10 mL) and EDCl hydrochloride (2 g, 10.44 mmol) were added. The reaction mixture was stirred at room temperature for 16 h under nitrogen atmosphere and TLC analysis showed the complete consumption of 1. DMAP (63.8 mg, 0.522 mmol) and a solution of linoleic acid (3659 mg, 13.05 mmol) in DMF (5 mL) were added to the reaction mixture. Then EDCl hydrochloride (2 g, 10.44 mmol) was added followed by the addition of dry DCM (10 mL). The reaction mixture was stirred at room temperature for 16 hours under nitrogen atmosphere. The completion of the reaction was confirmed by TLC analysis and the reaction mixture was concentrated under reduced pressure. The residue was dissolved in EtOAc (60 mL) and washed with water (2×50 mL). The aq. layer was extracted with EtOAc (2×30 mL) and the combined organic layers were washed with brine (2×50 mL). The organic layer was separated, dried over anhydrous $Na_2SO_4$, filtered and concentrated. The crude product was purified by silica gel (100-200 mesh) column chromatography (Isolera™) using 70% EtOAc in Pet. ether to afford PNI 325 (0.600 g, 0.765 mmol, 14.66% yield) as light-yellow oil. $_1$H (400 MHz, $CDCl_3$) δ 5.42-5.30 (m, 9H), 5.11 (app s, 1H), 4.33-4.15 (m, 4H), 3.76 (d, 1H, J=12.0), 2.83 (br s, 2H), 2.78 (app t, 4H, J=6.0), 2.35-2.29 (m, 5H), 2.26 (s, 3H), 2.06 (q, 8H, J=8.0), 2.01-1.89 (m, 4H), 1.81-1.75 (m, 2H), 1.68-1.59 (m, 4H), 1.40-1.26 (m, 28H), 0.90 (app t, 6H, J=6.0). RT=3.63 min. 97.4% purity. ESI-MS: m/z=785 [M+H]$_+$ for $C_{48}H_{82}NO_7$.

PNI 328:

To a well-stirred solution of (±)-1,4-anhdyroxylitol (1, 700 mg, 5.22 mmol) and DMAP (63.8 mg, 0.522 mmol) in dry DMF (5 mL) at 25° C., was added a solution of 1-methylpyrrolidine-3-carboxylic acid (674 mg, 5.22 mmol) in dry DMF (2.5 mL) under nitrogen atmosphere. Then, dry DCM (10 mL) and followed by EDCl hydrochloride (2 g, 10.44 mmol) were added. The reaction mixture was stirred at room temperature for 4 h and TLC analysis showed the complete consumption of 1. Then, DMAP (63.8 mg, 0.522 mmol) and a solution of linoleic acid (3659 mg, 13.05 mmol) in dry DMF (5 mL) were added to the above reaction mixture. Then EDCl hydrochloride (4002 mg, 20.88 mmol) and dry DCM (10 mL) were added. The reaction mixture was stirred at room temperature for 16 h under nitrogen atmosphere. After completion of the reaction as indicated by TLC, the reaction mixture was evaporated under reduced pressure. The residue was dissolved in EtOAc (60 mL) and washed with water (2×50 mL). The aq. layer was extracted with EtOAc (2×30 mL) and the combined organic layers were washed with brine (2×50 mL). The organic layer was separated, dried over anhydrous $Na_2SO_4$, filtered and concentrated. The crude product was purified by silica gel (100-200 mesh) column chromatography (Isolera™) using 70% EtOAc in Pet. Ether to provide PNI 328 (0.290 g, 0.377 mmol, 7.22% yield)) as light-yellow oil. $_1$H (400 MHz, $CDCl_3$) δ 5.41-5.30 (m, 9H), 5.12 (app s, 1H), 4.34-4.19 (m, 4H), 3.76 (d, 1H, J=12.0), 3.09-3.05 (m, 1H), 2.82-2.76 (m, 5H), 2.71-2.51 (m, 3H), 2.36-2.32 (m, 7H), 2.14-2.03 (m, 10H), 1.68-1.60 (m, 4H), 1.36-1.26 (m, 28H), 0.90 (app t, 6H, J=6.0). RT=3.62 min. 93.1% purity. ESI-MS: m/z=771 [M+H]$_+$ for $C_{47}H_{80}NO_7$.

PNI 329:

To a stirred solution of (±)-1,4-anhdyroxylitol (1, 0.7 g, 5.22 mmol) and DMAP (0.064 g, 0.522 mmol) in dry DMF (15 mL) at 25° C., was added a solution of 1,3-dimethylpyrrolidine-3-carboxylic acid (0.747 g, 5.22 mmol) in dry DMF (5 mL) under nitrogen atmosphere. Then, dry DCM (5 mL), EDCl hydrochloride (4.00 g, 20.88 mmol) and DIPEA (2.279 ml, 13.05 mmol) were added successively. The reaction mixture was stirred at room temperature for 4 h and TLC analysis showed the complete consumption of 1. To the reaction mixture, DMAP (0.064 g, 0.522 mmol) and a solution of linoleic acid (3.66 g, 13.05 mmol) in dry DMF (5 mL) were added. Then EDCl hydrochloride (4.00 g, 20.88 mmol) and DIPEA (3.37 g, 26.1 mmol) were added followed by dry DCM (5 mL). The reaction mixture was stirred at room temperature for 16 h under a nitrogen atmosphere. After completion of the reaction as indicated by TLC, the reaction mixture was evaporated under reduced pressure. The residue was dissolved in EtOAc (60 mL) and washed with water (2×50 mL). The aq. layer was extracted with EtOAc (2×30 mL) and the combined organic layers were washed with brine (2×50 mL). The organic layer was separated, dried over anhydrous $Na_2SO_4$, filtered and concentrated. The crude product was purified by silica gel (100-200 mesh) column chromatography (Isolera™) using 80% EtOAc in pet. Ether to afford PNI 329 (0.090 g, 0.115 mmol, 2.199% yield) as light-yellow oil. $_1$H (400 MHz, $CDCl_3$) δ 5.42-5.29 (m, 9H), 5.14-5.12 (m, 1H), 4.35-4.22 (m, 4H), 3.76 (dd, 1H, J=8.0, 4.0), 3.01 (app d, 1H, J=8.0), 2.78 (t, 4H, J=6.0), 2.71-2.57 (m, 2H), 2.47-2.39 (m, 2H), 2.39-2.31 (m, 7H), 2.09-1.97 (m, 9H), 1.79-1.67 (m, 4H), 1.37-1.26 (m, 31H), 0.88 (app t, 6H, J=6.0). RT=3.78 min. 91.6% purity. ESI-MS: m/z=785 [M+H]$_+$ for $C_{48}H_{82}NO_7$. PNI 336:

To a stirred solution of (±)-1,4-anhydroxylitol (1, 0.7 g, 5.22 mmol) in dry DMF (10 mL), was added DMAP (0.064 g, 0.522 mmol) at room temperature under nitrogen atmosphere. To this mixture, a solution of 2-(1-methyl-1H-imidazol-4-yl)acetic acid (0.731 g, 5.22 mmol) in DMF (5 mL) and then, dry DCM (5 mL) were added. Then, EDCl hydrochloride (2.001 g, 10.44 mmol) and DIPEA (2.329 ml, 13.05 mmol) were added. The reaction mixture was stirred at room temperature for 4 h and TLC analysis showed the complete consumption of 1. To the above mixture, DMAP (0.064 g, 0.522 mmol) and a solution of linoleic acid (3.66 g, 13.05 mmol) in DMF (5 mL) were added. Then, EDCl hydrochloride (4.00 g, 20.88 mmol) and DIPEA (3.37 g, 26.1 mmol) were added. Finally, dry DCM (5 mL) was added and the reaction mixture was stirred at room temperature for 16 hours. TLC analysis showed the completion of the starting materials. The solvent was evaporated under reduced pressure and the residue was dissolved in EtOAc (60 mL). The EtOAc layer was washed with water (2×30 mL) and the combined aqueous layers were extracted with EtOAc (2×30 mL). The combined organic layers were washed with brine (2×50 mL) and dried over anhydrous $Na_2SO_4$. The organic layer was filtered and concentrated under reduced pressure. The crude was purified by silica gel (100-200 mesh) column chromatography (Isolera™) using 70% EtOAc in Pet. ether to afford PNI 336 (0.37 g, 0.474 mmol, 9.08% yield) as a pale-yellow liquid. $_1$H (400 MHz, $CDCl_3$) δ 7.45 (s, 1H), 6.88 (s, 1H), 5.42-5.30 (m, 9H), 5.11-5.09 (m, 1H), 4.37-4.20 (m, 4H), 3.75 (dd, 1H, J=8.0, 4.0), 3.70-3.69 (m, 2H), 3.68 (s, 3H), 2.77 (t, 4H, J=6.0), 2.33 (t, 4H, J=8.0), 2.05 (q, 8H, J=8.0), 1.64-1.59 (m, 4H), 1.38-1.26 (m, 28H), 0.89 (app t, 6H, J=6.0). RT=3.44 min. 89.4% purity. ESI-MS: m/z=782 [M+H]$_+$ for $C_{47}H_{77}N_2O_7$.

PNI 538:

To a stirred solution of (±)-1,4-anhydroxylitol (1, 0.5 g, 3.73 mmol) in dry DMF (10 mL), was added DMAP (0.046 g, 0.373 mmol) at room temperature under nitrogen atmosphere. To this mixture, a solution of 2-(1-methylpyrrolidin-3-yl)acetic acid (0.587 g, 4.10 mmol) in DMF (5 mL) and then, dry DCM (10 mL) were added. EDCl hydrochloride (1.429 g, 7.46 mmol) and DIPEA (1.664 mL, 9.32 mmol) were added to the content of the reaction flask. The reaction mixture was stirred at room temperature for 4 h and TLC analysis showed the complete consumption of 1. Then, DMAP (0.455 g, 3.73 mmol) and a solution of linoleic acid (2.61 g, 9.32 mmol) in DMF (5 mL) were added. To the reaction mixture, EDCl hydrochloride (2.86 g, 14.91 mmol) and DIPEA (2.409 g, 18.64 mmol) were added. Finally, dry DCM (10 mL) was added and the reaction mixture was stirred at room temperature for 16 hours. TLC analysis showed the consumption of starting material. The solvent was evaporated under reduced pressure and the residue was dissolved in EtOAc (60 mL). The EtOAc layer was washed with water (2×30 mL) and the combined aqueous layers were extracted with EtOAc (2×30 mL). The combined organic layers were washed with brine (2×50 mL) and dried over anhydrous Na$_2$SO$_4$. The organic layer was filtered and concentrated under reduced pressure. The crude product was purified by silica gel (100-200 mesh) column chromatography (Isolera™) using 70% EtOAc in Pet. ether to afford PNI 538 (0.165 g, 0.210 mmol, 5.64% yield) as a light-yellow oil. $_1$H (400 MHz, CDCl$_3$) δ 5.43-5.30 (m, 9H), 5.12-5.11 (m, 1H), 4.32-4.14 (m, 4H), 3.75 (dd, 1H, J=12.0, 4.0), 2.83-2.73 (m, 5H), 2.65-2.50 (m, 3H), 2.46-2.44 (m, 2H), 2.37-2.82 (m, 8H), 2.18-2.03 (m, 10H), 1.55-1.42 (m, 4H), 1.40-1.24 (m, 28H), 0.90 (app t, 6H, J=6.0). RT=3.23 min. 87.0% purity. ESI-MS: m/z=785 [M+H]$_+$ for C$_{48}$H$_{82}$NO$_7$. PNI 539:

DMF (10 mL) at 25° C., was added a solution of 4-(pyrrolidin-1-yl)butanoic acid hydrochloride (0.866 g, 4.47 mmol) in dry DMF (2.5 mL) under nitrogen atmosphere. Then, EDCl hydrochloride (1.715 g, 8.95 mmol) and dry DCM (10 mL) were added. The reaction mixture was stirred at room temperature for 4 hours and TLC analysis showed the complete consumption of 1. To the reaction mixture, DMAP (0.109 g, 0.895 mmol) and a solution of linoleic acid (3.14 g, 11.18 mmol) in dry DMF (7.5 mL) were added. Then, EDCl hydrochloride (3.43 g, 17.89 mmol) and dry DCM (10 mL) were added. The reaction mixture was stirred at room temperature for 16 h under nitrogen atmosphere. After completion of the reaction as indicated by TLC, the reaction mixture was evaporated under reduced pressure. The residue was dissolved in EtOAc (70 mL) and washed with water (2×40 mL). The aq. layer was extracted with EtOAc (2×35 mL) and the combined organic layers were washed with brine (2×50 mL). The organic layer was separated, dried over anhydrous Na$_2$SO$_4$, filtered and concentrated. The crude product was purified by column chromatography (Isolera™) using silica gel (100-200 mesh) using 70% EtOAc in Pet. ether to yield PNI 539 (0.5 g, 0.608 mmol, 13.58% yield) as light-yellow oil. $_1$H (400 MHz, CDCl$_3$) δ 5.42-5.30 (m, 9H), 5.13-5.11 (m, 1H), 4.33-4.14 (m, 4H), 3.75 (dd, 1H, J=12.0, 4.0), 2.78 (t, 4H, J=6.0), 2.50-2.31 (m, 12H), 2.06 (q, 8H, J=8.0), 1.84 (p, 2H, J=8.0), 1.78-1.75 (m, 4H), 1.67-1.60 (m, 4H), 1.40-1.25 (m, 28H), 0.90 (app t, 6H, To a well-stirred solution of (±)-1,4-anhdyroxylitol (1, 0.6 g, 4.47 mmol) and DMAP (0.055 g, 0.447 mmol) in dry J=6.0). RT=3.71 min. 90.6% purity. ESI-MS: m/z=799 [M+H]$_+$ for C$_{49}$H$_{84}$NO$_7$.

PNI 540:

To a well-stirred solution of (±)-1,4-anhdyroxylitol (1, 0.6 g, 4.47 mmol) and DMAP (0.055 g, 0.447 mmol) in dry DMF (10 mL) at 25° C., was added 2-(1-methylpiperidin-2-yl)acetic acid hydrochloride (0.866 g, 4.47 mmol) in dry DMF (2.5 mL) under nitrogen atmosphere. Then, EDCl (1.715 g, 8.95 mmol) and dry DCM (10 mL) were added. The reaction mixture was stirred at room temperature for 4 h and TLC analysis showed the complete consumption of 1. To this reaction mixture, DMAP (0.109 g, 0.895 mmol) and a solution of linoleic acid (3.14 g, 11.18 mmol) in DMF (7.5 mL) were added. Then, EDCl hydrochloride (3.43 g, 17.89 mmol) and dry DCM (10 mL) were added. The reaction mixture was stirred at 25° C. for 16 h under nitrogen atmosphere. After completion of the reaction as indicated by TLC, the reaction mixture was evaporated under reduced pressure. The residue was dissolved in EtOAc (70 mL) and washed with water (2×40 mL). The aq. layer was extracted with EtOAc (2×35 mL) and the combined organic layers were washed with brine (2×50 mL). The organic layer was dried over anhydrous $Na_2SO_4$, filtered and concentrated. The crude product was purified by silica gel (100-200 mesh) column chromatography (Isolera™) using 75% EtOAc in Pet. ether to give PNI 540 (0.41 g, 0.500 mmol, 11.18% yield) as light-yellow oil. $_1H$ (400 MHz, $CDCl_3$) δ 5.42-5.30 (m, 9H), 5.13-5.11 (m, 1H), 4.33-4.17 (m, 4H), 3.75 (dd, 1H, J=12.0, 4.0), 2.86 (br s, 2H), 2.78 (t, 4H, J=6.0), 2.60 (br s, 1H), 2.46-2.27 (m, 9H), 2.06 (q, 8H, J=8.0), 1.77-1.61 (m, 10H), 1.40-1.25 (m, 28H), 0.89 (app t, 6H, J=6.0). RT=3.79 min. 97.4% purity. ESI-MS: m/z=799 $[M+H]_+$ for $C_{49}H_{84}NO_7$.

Example 3

Synthesis of PNI 342 and 541

Scheme 3. Synthesis of compound 4

Scheme 4. General route for the synthesis of PNI 342 and 541

Compound 2:

To a stirred solution of oleic acid (58 g, 205 mmol) in dry EtOH (580 mL), conc. $H_2SO_4$ (1.094 mL, 20.53 mmol) was added slowly and the reaction mixture was refluxed for 16 h. Upon completion of the reaction as indicated by TLC, the solvent was evaporated under reduced pressure. The residue was cooled to 0° C., neutralised with satd. aq. $NaHCO_3$ solution and extracted with DCM (3×250 mL). The combined organic layers were dried over anhydrous $Na_2SO_4$, filtered and concentrated to obtain ethyl oleate (2, 61.6 g, 198 mmol, 97% yield) as colorless oil. The ester was taken as such for next step without further purification. $_1H$ (400 MHz, $CDCl_3$) δ 5.39-5.31 (m, 2H), 4.13 (q, 2H, J=8.0), 2.29 (t, 2H, J=8.0), 2.02 (app q, 4H, J=8.0), 1.62 (p, 2H, J=8.0), 1.35-1.24 (m, 23H), 0.89 (t, 3H, J=6.0). RT=3.73 min. 99.5% purity. ESI-MS: m/z=311 [M+H]$_+$ for $C_{20}H_{39}O_2$.

Compound 3:

A solution diiodomethane (31.2 mL, 386 mmol) in toluene (120 mL) was stirred at –15° C. under nitrogen atmosphere. Diethylzinc (129 ml, 193 mmol, 1.5M solution in toluene) was added dropwise to the reaction mixture at –15° C. for 30 mins. Note: The internal temperature of the reaction mixture should be maintained less than 0° C. Then, a solution of 2 (30 g, 97 mmol) in toluene (30 mL) was added dropwise to above reaction mixture so that internal temperature is maintained less than 0° C. The reaction mixture was stirred at same temperature for 15 mins and gradually allowed to warm to room temperature over 30 mins. After stirring for 7 h at room temperature, TLC analysis showed the completion of reaction. The reaction mixture was cooled to 0° C. and quenched with satd. aq.

$NH_4Cl$ solution (100 mL). The organic layer was separated, and the aq. layer was extracted with toluene (2×75 mL). The combined organic layers were dried over anhydrous $Na_2SO_4$, filtered and concentrated. The crude product was purified by silica gel (100-200 mesh) column chromatography (Isolera™) using 6% EtOAc in Pet. ether to afford 3 (28.05 g, 86 mmol, 89% yield) as pale-yellow oil. $_1H$ (400 MHz, $CDCl_3$) δ 4.13 (q, 2H, J=8.0), 2.29 (t, 2H, J=8.0), 1.63 (p, 2H, J=8.0), 1.38-1.24 (m, 25H), 1.19-1.08 (m, 2H), 0.89 (t, 3H, J=6.0), 0.68-0.62 (m, 2H), 0.59-0.54 (m, 1H), –0.34 (app q, 1H, J=4.0). RT=4.01 min. 98.7% purity. ESI-MS: m/z=325 [M+H]$_+$ for $C_{21}H_{41}O_2$.

Compound 4:

LiOH (1.660 g, 69.3 mmol) was added to a stirred solution of 3 (15 g, 46.2 mmol) in EtOH (105 mL) and water (45 mL) and the reaction mixture was stirred at ambient temperature for 16 h. Upon the completion of the reaction as indicated by TLC, the reaction mixture was concentrated in vacuo to obtain the residue. The residue was diluted with water (100 mL) and washed with MTBE (2×100 mL). The aq. layer was cooled to 0° C., acidified with 6N HCl and extracted with EtOAc (3×300 mL). The combined organic layers were dried over anhyd. $Na_2SO_4$, filtered and concentrated to obtain 4 (13.05 g, 43.0 mmol, 93% yield) as white solid. $_1H$ (400 MHz, $CDCl_3$) δ 2.36 (t, 2H, J=6.0), 1.64 (p, 2H, J=8.0), 1.39-1.28 (m, 22H), 1.19-1.10 (m, 2H), 0.89 (t, 3H, J=6.0), 0.68-0.62 (m, 2H), 0.59-0.54 (m, 1H), –0.33 (app q, 1H, J=4.0). RT=2.91 min. 97.7% purity. ESI-MS: m/z=295 [M–H]$_-$ or $C_{19}H_{35}O_2$.

PNI 342:

To a stirred solution of (±)-1,4-anhydroxylitol (1, 0.8 g, 5.96 mmol) in dry DMF (10 mL), DMAP (0.073 g, 0.596 mmol) was added at room temperature under nitrogen atmosphere. To this mixture, a solution of 3-(dimethyl-amino)propanoic acid hydrochloride (0.916 g, 5.96 mmol) in dry DMF (3 mL) was added, followed by dry DCM (10 mL) and then EDCl hydrochloride (2.287 g, 11.93 mmol). The reaction mixture was stirred at room temperature for 4 h and the consumption of 1 was confirmed by TLC analysis. To the above reaction mixture, DMAP (0.146 g, 1.193 mmol) and a solution of 4 (4.42 g, 14.91 mmol) in dry DMF (10 mL) was added. Then, EDCl hydrochloride (4.57 g, 23.86 mmol), followed by dry DCM (10 mL) was added and the reaction mixture was stirred at room temperature for 16 h. TLC analysis showed the complete consumption of start-ing material and the reaction mixture was concentrated under reduced pressure. The residue was dissolved in EtOAc (60 mL) and washed with water. The aq. layer was extracted with EtOAc (2×30 mL) and the combined organic layers were washed with brine (2×50 mL). The organic layer was separated, dried over anhyd. $Na_2SO_4$, filtered and concen-trated. The crude product was purified by silica gel (100-200 mesh) column chromatography (Isolera™) using 50% EtOAc in Pet. ether. The product was re-purified (Isolera™) using 10% acetone in DCM to give PNI 342 (0.19 g, 0.240 mmol, 4.03% yield) as light-yellow oil. $_1$H (400 MHz, $CDCl_3$) δ 5.38-5.35 (m, 1H), 5.16-5.12 (m, 1H), 4.34-4.14 (m, 4H), 3.80-3.74 (m, 1H), 2.66-2.58 (m, 2H), 2.55-2.50 (m, 2H), 2.36-2.31 (m, 4H), 2.25 (s, 6H), 1.62 (p, 4H, J=8.0), 1.39-1.26 (m, 44H), 1.19-1.09 (m, 4H), 0.89 (app t, 6H, J=8.0), 0.68-0.62 (m, 4H), 0.59-0.54 (m, 2H), −0.33 (app q, 2H, J=4.0). RT=5.03 min. 94.7% purity. ESI-MS: m/z=791 [M+H]$_+$ for $C_{48}H_{88}NO_7$.

PNI 541:

To a well-stirred solution of (±)-1,4-anhdyroxylitol (1, 0.6 g, 4.47 mmol) and DMAP (0.055 g, 0.447 mmol) in dry DMF (10 mL) at 25° C., was added a solution of 1,4-dimethylpiperidine-4-carboxylic acid hydrochloride (0.866 g, 4.47 mmol) in dry DMF (2.5 mL). Then, EDCl hydro-chloride (1.715 g, 8.95 mmol) and dry DCM (10 mL) were added. The reaction mixture was stirred at room temperature for 4 h and TLC analysis showed the complete consumption of 1. To this reaction mixture, DMAP (0.109 g, 0.895 mmol) and a solution of 4 (3.32 g, 11.18 mmol) in dry DMF (7.5 mL) were added. Then, EDCl hydrochloride (3.43 g, 17.89 mmol) and dry DCM (10 mL) were added to reaction mixture. The reaction mixture was stirred at room tempera-ture for 16 hours under nitrogen atmosphere. After comple-tion of the reaction as indicated by TLC, the reaction mixture was evaporated under reduced pressure. The residue was dissolved in EtOAc (70 mL) and washed with water (2×40 mL). The aq. layer was extracted with EtOAc (2×35 mL) and the combined organic layers were washed with brine (2×50 mL). The organic layer was separated, dried over anhyd. $Na_2SO_4$, filtered and concentrated. The crude prod-uct was purified by silica gel (100-200 mesh) column chromatography (Isolera™) using 65% EtOAc in Pet. ether to afford PNI 541 (0.68 g, 0.819 mmol, 18.31% yield) as colorless oil. $_1$H (400 MHz, $CDCl_3$) δ 5.35 (d, 1H, J=4.0), 5.15-5.13 (m, 1H), 4.33-4.23 (m, 4H), 3.76 (d, 1H, J=12.0), 2.92 (br s, 2H), 2.61-2.39 (m, 4H), 2.36 (td, 4H, J=8.0, 4.0), 2.22-2.19 (m, 3H), 1.68-1.57 (m, 6H), 1.39-1.25 (m, 47H), 1.19-1.11 (m, 4H), 0.89 (app t, 6H, J=6.0), 0.71-0.62 (m, 4H), 0.59-0.54 (m, 2H), −0.33 (q, 2H, 4.0). RT=5.03 min. 96.2% purity. ESI-MS: m/z=831 [M+H]$_+$ for $C_{51}H_{92}NO_7$.

Example 4

Synthesis of PNI 535 temperature for 16 h. TLC analysis showed the completion of starting material. The reaction mixture was concentrated under reduced pressure and the residue was dissolved in Scheme 5. Synthesis of PNI 535

PNI 535

To a stirred solution of (±)-1,4-anhydroxylitol (1, 0.70 g, 5.22 mmol) in dry DMF (5 mL), was added DMAP (0.064 g, 0.522 mmol) at room temperature under nitrogen atmosphere. To this mixture, a solution of 3-(dimethylamino) propanoic acid hydrochloride (0.673 g, 5.74 mmol) in dry DMF (2.5 mL) and then dry DCM (5 mL) was added. Then, EDCl hydrochloride (2.001 g, 10.44 mmol) and DIPEA (2.329 ml, 13.05 mmol) were added. The reaction mixture was stirred at room temperature for 4 h and TLC analysis showed the consumption of 1. To the reaction flask, DMAP (0.064 g, 0.522 mmol) and a solution of 2-hexyldecanoic acid 5 (3.35 g, 13.05 mmol) in DMF (5 mL) were added. Then, EDCl hydrochloride (4.00 g, 20.88 mmol) and DIPEA (3.37 g, 26.1 mmol) were added. Finally, dry DCM (5 mL) was added and the reaction mixture was stirred at room EtOAc (60 mL). The EtOAc layer was washed with water (2×30 mL) and the combined aq. layers were extracted with EtOAc (2×30 mL). The combined organic layers were washed with brine (2×50 mL) and dried over anhydrous Na$_2$SO$_4$. The organic layer was separated, filtered, and concentrated under reduced pressure. The crude product was purified by silica gel (100-200 mesh) column chromatography (Isolera™) using 60% EtOAc in Pet. ether to provide PNI 535 (0.43 g, 0.606 mmol, 11.60% yield) as a colourless liquid. $_1$H (400 MHz, CDCl$_3$) δ 5.35-5.32 (m, 1H), 5.12-5.08 (m, 1H), 4.34-4.20 (m, 4H), 3.80-3.73 (m, 1H), 2.64-2.60 (m, 2H), 2.53-2.49 (m, 2H), 2.40-2.31 (m, 2H), 2.24 (s, 6H), 1.60-1.53 (m, 4H), 1.50-1.40 (m, 4H), 1.34-1.16 (m, 40H), 0.88 (app t, 12H, J=8.0). RT=3.08 min. 97.9% purity. ESI-MS: m/z=711 [M+H]$_+$ for C$_{42}$H$_{80}$NO$_7$.

Example 5. Synthesis of PNI 119, 120 and 344

Scheme 6. General route for synthesis of PNI 119, 120 and 344

(±)-1

PNI 119:

To a solution of (±)-1 (1.25 g, 9.3 mmol) in dry DMF (15 mL), DMAP (cat.) was added followed by addition of a solution of 4-(dimethylamino)butanoic acid hydrochloride (1.56 g, 9.3 mmol) in dry DMF (10 mL) under $N_2$ atmosphere. $CH_2Cl_2$ (25 mL) was added to the reaction mixture at room temperature. Finally, solid EDCl hydrochloride (3.56 g, 18.6 mmol) was added and the reaction was stirred at room temperature for 4 h. TLC analysis of the reaction mixture shows complete consumption of (±)-1. Further, DMAP (cat.) was added to the reaction mixture followed by addition of Myristic acid (5.32 g, 23.3 mmol) dissolved in dry DMF (20 mL) and EDCl hydrochloride (7.13 g, 37.2 mmol) as solid. Next, dry $CH_2Cl_2$ (10 mL) was added and the reaction mixture was stirred overnight at room temperature. The reaction mixture was concentrated over a rotary evaporator, diluted with EtOAc (50 mL) and washed with water (3×20 mL). Organic layer was washed with brine, dried over anhyd. $Na_2SO_4$ and evaporated to dryness over rotary evaporator to provide crude mixture which was purified by column chromatography using 5% MeOH/DCM as the eluent. PNI 119 was obtained as colorless oil (780 mg, 1.17 mmol) in 13% yield. $_1$H (500 MHz, $CDCl_3$) δ 5.36 (d, 1H, J=5.0 Hz), 5.13-5.11 (m, 1H), 4.33-4.28 (m, 2H), 4.25 (dd, 1H, J=10.0 Hz, 5.0 Hz), 4.18 (dd, 1H, J=10.0 Hz, 7.5 Hz), 3.75 (d, 1H, J=10.0 Hz), 2.39-2.32 (m, 6H), 2.28 (apparent t, 2H, J=5.0 Hz), 2.21 (s, 6H), 1.79 (p, 2H, J=7.5 Hz), 1.65-1.59 (m, 4H), 1.33-1.26 (m, 40H), 0.89 (apparent t, 6H, J=7.5 Hz). Molecular weight for $C_{39}H_{74}NO_7$ $[M+H]_+$ Calculated 668.5465. Found 668.5466.

PNI 120:

To a solution of (±)-1 (1.25 g, 9.3 mmol) in dry DMF (15 mL), DMAP (cat.) was added followed by addition of a solution of 5-(dimethylamino)pentanoic acid hydrochloride (1.68 g, 9.3 mmol) in dry DMF (10 mL) under N$_2$ atmosphere at room temperature. CH$_2$Cl$_2$ (25 mL) was added to the reaction mixture. Finally, solid EDCl hydrochloride (3.56 g, 18.6 mmol) was added to the reaction mixture and was stirred at room temperature for 4 h. TLC analysis of the reaction mixture shows complete consumption of (±)-1. Further, DMAP (cat.) was added to the reaction mixture followed by addition of Myristic acid (5.31 g, 23.3 mmol) dissolved in dry DMF (20 mL) and EDCl hydrochloride (7.13 g, 37.2 mmol) as solid. Next, dry DCM (10 mL) was added and the reaction mixture was stirred overnight at room temperature. The reaction mixture was concentrated over a rotary evaporator, diluted with EtOAc (50 mL) and washed with water (3×20 mL). Organic layer was washed with brine, dried over anhydrous Na$_2$SO$_4$ and evaporated to dryness over a rotary evaporator to provide crude mixture which was purified by silica gel column chromatography using 5% MeOH/DCM as the eluent. PNI 120 was obtained as colorless oil (1.03 g, 1.51 mmol) in 16% yield. $_1$H (500 MHz, CDCl$_3$) δ 5.35 (d, 1H, J=5.0 Hz), 5.12-5.11 (m, 1H), 4.32-4.23 (m, 3H), 4.16 (dd, 1H, J=10.0 Hz, 7.5 Hz), 3.75 (d, 1H, J=10.0 Hz), 2.38-2.28 (m, 8H), 2.23 (s, 6H), 1.68-1.59 (m, 6H), 1.51 (p, 2H, J=7.5 Hz), 1.32-1.25 (m, 40H), 0.88 (apparent t, 6H, J=7.5 Hz). Molecular weight for C$_{40}$H$_{76}$NO$_7$ [M+H]$_+$ Calculated 682.5622. Found 682.5589. PNI 344:

To a stirred solution of (±)-1,4-anhydroxylitol (1, 0.500 g, 3.73 mmol) in dry DMF (5 mL), DMAP (0.046 g, 0.373 mmol) was added at room temperature under nitrogen atmosphere. To this mixture, a solution of 3-(dimethylamino)propanoic acid hydrochloride (0.437 g, 3.73 mmol) in dry DMF (2.5 mL) and dry DCM (10 mL) was added. EDCl hydrochloride (1.429 g, 7.46 mmol)) and DIPEA (1.623 ml, 9.32 mmol) were added and the reaction mixture was stirred at room temperature for 4 h. TLC analysis showed the complete consumption of 1. Then, DMAP (0.046 g, 0.373 mmol) and a solution of myristic acid (2.128 g, 9.32 mmol) in DMF (5 mL) was added to the above reaction mixture. Further, EDCl hydrochloride (2.86 g, 14.91 mmol) and DIPEA (3.25 ml, 18.64 mmol) were added. Finally, dry DCM (10 mL) was added to the reaction mixture and stirred at room temperature for 16 h. The completion of the reaction was confirmed by TLC analysis and the reaction mixture was concentrated under reduced pressure. The residue was dissolved in EtOAc (60 mL) and washed with water (2×30 mL). The aq. layer was extracted with EtOAc (2×30 mL) and the combined organic layer washed with brine (2×50 mL). The organic layer was separated, dried over anhyd. Na$_2$SO$_4$, filtered and concentrated. The crude product was purified by silica gel (100-200 mesh) column chromatography (Isolera™) using 70% EtOAc in Pet. ether to afford PNI 344 (0.220 g, 0.336 mmol, 9.02% yield) as colourless oil. $_1$H (400 MHz, CDCl$_3$) δ 5.38-5.34 (m, 1H), 5.13-5.11 (m, 1H), 4.34-4.16 (m, 4H), 3.76 (d, 1H, J=12.0), 2.65-2.61 (m, 2H), 2.54-2.50 (m, 2H), 2.36-2.31 (m, 4H), 2.25 (s, 6H), 1.62 (p, 4H, J=8.0), 1.35-1.22 (m, 40H), 0.88 (app t, 6H, J=6.0). RT=3.57 min. 91.8% purity. ESI-MS: m/z=655 [M+H]$_+$ for C$_{38}$H$_{72}$NO$_7$.

Example 6

Synthesis of PNI 534

Scheme 7. Synthesis of PNI 534

PNI 534

To a stirred solution of (±)-1,4-anhydroxylitol (1, 1.0 g, 7.46 mmol) in dry DMF (5 mL), DMAP (0.091 g, 0.746 mmol) was added at room temperature under nitrogen atmosphere. To this mixture, a solution of 3-(dimethylamino)propanoic acid hydrochloride (0.961 g, 8.20 mmol) in DMF (2.5 mL) and then dry DCM (10 mL) was added. Then, EDCl hydrochloride (2.86 g, 14.91 mmol) and DIPEA (2.409 g, 18.64 mmol) were added. The reaction mixture was stirred at room temperature for 4 h and TLC analysis showed the consumption of 1. To the reaction mixture, DMAP (0.091 g, 0.746 mmol) and a solution of dodecanoic acid (3.73 g, 18.64 mmol) in dry DMF (5 mL) were added. Then, EDCl hydrochloride (5.72 g, 29.8 mmol) and DIPEA (4.82 g, 37.3 mmol) were added. Finally, dry DCM (10 mL) was added and the mixture was stirred at room temperature for 16 h. TLC analysis showed the complete consumption of starting materials. The reaction mixture was concentrated under reduced pressure and the residue was dissolved in EtOAc (60 mL). The EtOAc layer was washed with water (2×30 mL) and the combined aq. layers were extracted with EtOAc (2×30 mL). The combined organic layers were washed with brine (2×50 mL) and dried over anhyd. $Na_2SO_4$. The organic layer was filtered and concentrated under reduced pressure. The crude product was purified by silica gel (100-200 mesh) column chromatography (Isolera™) using 70% EtOAc in Pet. ether to give PNI 534 (0.230 g, 0.385 mmol, 5.16% yield) as colourless oil. $_1$H (400 MHz, $CDCl_3$) δ 5.38-5.34 (m, 1H), 5.16-5.11 (m, 1H), 4.34-4.15 (m, 4H), 3.80-3.74 (m, 1H), 2.64-2.59 (m, 2H), 2.53-2.49 (m, 2H), 2.36-2.31 (m, 4H), 2.24 (s, 6H), 1.62 (p, 4H, J=8.0), 1.36-1.21 (m, 32H), 0.88 (app t, 6H, J=6.0). RT=1.85 min. 85.6% purity. ESI-MS: m/z=599 [M+H]$_+$ for $C_{34}H_{64}NO_7$.

Example 7

Synthesis of PNI 532

Scheme 8. Synthesis of compound 9

Scheme 9. Synthesis of PNI 532

PNI 532

Compound 8:

To a stirred solution of 8-(tert-butoxy)-8-oxooctanoic acid (6, 11.36 g, 49.3 mmol in dry DCM (100 mL) was added DMAP (0.524 g, 4.29 mmol) at room temperature under nitrogen atmosphere. (Z)-Non-2-en-1-ol (7, 6.1 g, 42.9 mmol) was added to the above mixture and stirring was continued for 15 mins The reaction was cooled to 0° C. and DCC (9.73 g, 47.2 mmol) was added. The reaction mixture was allowed to reach room temperature and stirred for 16 h. TLC analysis showed the complete consumption of starting materials. The precipitated urea was filtered through celite pad and washed with DCM (2×50 mL). The combined filtrates were concentrated, and the residue was washed with satd. aq. NaHCO$_3$ solution (2×50 mL). The organic layer was separated, dried over anhydrous Na$_2$SO$_4$. The solvent was removed under reduced pressure and the residue was purified by silica gel (100-200 mesh) column chromatography (Isolera™) using 3% EtOAc in Pet. ether to give the (Z)-1-(tert-butyl) 8-(non-2-en-1-yl) octanedioate (8, 11.35 g, 29.8 mmol, 69.4% yield). $_1$H (400 MHz, CDCl$_3$) δ 5.68-5.61 (m, 1H), 5.56-5.49 (m, 1H), 4.63 (d, 2H, J=4.0), 2.31 (t, 2H, J=8.0), 2.20 (t, 2H, J=8.0), 2.10 (app q, 2H, J=8.0), 1.67-

1.57 (m, 4H), 1.44 (s, 9H), 1.40-1.25 (m, 12H), 0.89 (t, 3H, J=6.0). RT=1.40 min. 89.2% purity. ESI-MS: m/z=377 [M+Na]$_+$ for C$_{21}$H$_{38}$O$_4$Na.

Compound 9:

TFA (10.00 mL, 130 mmol) was added dropwise to a stirred solution of 8 (5 g, 14.10 mmol) in dry DCM (50 mL) at room temperature under nitrogen atmosphere and the stirring was continued for 16 h. TLC analysis showed the presence of 8. Once again, TFA (10.00 mL, 130 mmol) was added and the reaction mixture was refluxed for 16 h. The reaction did not go for the completion and TLC analysis showed the presence of 8. The reaction was stopped, and the mixture was evaporated under reduced pressure. The crude material was purified by column silica gel (100-200 mesh) chromatography (Isolera™) using 30% EtOAc in Pet. ether to provide (Z)-8-(non-2-en-1-yloxy)-8-oxooctanoic acid (9, 3.41 g, 11.43 mmol, 81% yield) as a brown oil and 600 mg of 8 was also recovered. $_1$H (400 MHz, CDCl$_3$) δ 5.68-5.61 (m, 1H), 5.56-5.49 (m, 1H), 4.63 (d, 2H, J=4.0), 2.37-2.30 (m, 4H), 2.10 (app q, 2H, J=8.0), 1.68-1.60 (m, 4H), 1.40-1.24 (m, 12H), 0.89 (t, 3H, J=6.0).

PNI 532:

Into a 100 mL two necked round bottomed flask containing a well-stirred solution of (±)-1,4-anhydroxylitol (1, 0.5 g, 3.73 mmol) in dry DMF (5 mL) was added DMAP (0.046 g, 0.373 mmol) and a solution of 3-(dimethylamino)propanoic acid hydrochloride (0.480 g, 4.10 mmol) in dry DMF (2.5 mL) at room temperature under nitrogen atmosphere. To this mixture was added dry DCM (10 mL), followed by EDCl (1.429 g, 7.46 mmol) and DIPEA (1.204 g, 9.32 mmol). The reaction mixture was stirred at ambient temperature for 4 h and TLC analysis showed the consumption of 1. DMAP (0.046 g, 0.373 mmol) was added to above reaction mixture. A solution of 9 (2.78 g, 9.32 mmol) in dry DMF (5 mL) was added, followed by EDCl hydrochloride (2.86 g, 14.91 mmol) and DIPEA (2.409 g, 18.64 mmol). Finally, dry DCM (10 mL) was added and the reaction mixture was stirred at room temperature for 16 h. After completion of the reaction as indicated by TLC, the solvent was evaporated under reduced pressure and the residue was dissolved in EtOAc (60 mL). The organic layer was washed with water (2×30 mL) and the aq. layer was extracted with EtOAc (2×30 mL). The combined organic layers were washed with brine (2×50 mL) and dried over anhyd. $Na_2SO_4$. The organic layer was separated, filtered and concentrated under reduced pressure to obtain the crude. The crude product was purified by silica gel (100-200 mesh) column chromatography (Isolera™) using 70% EtOAc in Pet. ether to afford PNI 532 (0.270 g, 0.340 mmol, 9.12% yield) as a light-yellow oil. $_1$H (400 MHz, CDCl$_3$) δ 5.68-5.61 (m, 2H), 5.55-5.49 (m, 2H), 5.37-5.34 (m, 1H), 5.16-5.10 (m, 1H), 4.62 (d, 4H, J=8.0), 4.33-4.10 (m, 4H), 3.79-3.73 (m, 1H), 2.65-2.60 (m, 2H), 2.53-2.50 (m, 2H), 2.36-2.28 (m, 8H), 2.25 (s, 6H), 2.10 (q, 4H, J=8.0), 1.67-1.59 (m, 8H), 1.39-1.24 (m, 24H), 0.89 (app t, 6H, J=6.0). RT=2.24 min. 97.2% purity. ESI-MS: m/z=795 [M+H]$_+$ for $C_{44}H_{76}NO_{11}$.

Example 8. Synthesis of PNI 127, 573, 574 and 575

Scheme 10. General route for synthesis of PNI 127, 573, 574 and 575

-continued

12

Compound 10:

Into a 100 mL single necked round bottomed flask, a well-stirred solution of (±)-1,4-anhdyroxylitol (1, 5.1 g, 38.0 mmol) in dry pyridine (25 mL), trityl chloride (10.07 g, 36.1 mmol) was added at room temperature under nitrogen atmosphere and the stirring was continued for 16 h. After completion of the reaction as indicated by TLC, excess solvent was concentrated under reduced pressure. The residue was dissolved in DCM (100 mL) and water (200 mL). The organic layer was separated, and the aq. layer was extracted with DCM (3×50 mL). The combined organic layers were washed with brine (3×100 mL), dried over anhyd. Na$_2$SO$_4$, filtered and concentrated. The crude product was purified by silica gel (100-200 mesh) column chromatography using 50% EtOAc in Pet. Ether to give (±)-10 (8.65 g, 22.93 mmol, 60.3% yield) as white gummy solid. $_1$H (400 MHz, CDCl$_3$) δ 7.47-7.43 (m, 6H), 7.34-7.30 (m, 6H), 7.28-7.23 (m, 3H), 4.32 (br s, 1H), 4.28-4.23 (m, 3H), 3.77 (dd, 1H, J=12.0, 4.0), 3.50 (dd, 1H, J=12.0, 4.0), 3.43 (dd, 1H, J=8.0, 4.0), 3.14 (br s, 1H). RT=2.66 min. 99.9% purity. ESI-MS: m/z=375 [M–H]_ for C$_{24}$H$_{23}$O$_4$.

Compound 11:

Into a 250 mL three necked round bottomed flask, a stirred solution of linoleic acid (6.55 g, 23.36 mmol) in dry DCM (50 mL), DMAP (2.85 g, 23.36 mmol), EDCl hydrochloride (17.91 g, 93 mmol) and DIPEA (9.38 ml, 53.7 mmol) were added at room temperature under nitrogen atmosphere. The reaction mixture was stirred for 15 mins and a solution of (±)-10 (3.52 g, 9.34 mmol) in dry DCM (20 mL) was added. After stirring for 16 h, the reaction mixture was quenched with water (150 mL) and extracted with DCM (3×50 mL). The combined organic layers were washed with brine (3×75 mL), dried over anhyd. Na$_2$SO$_4$, filtered and concentrated. The crude product was purified by silica gel (100-200 mesh) column chromatography (Isolera™) using 5% EtOAc in Pet. ether to provide (±)-11 (7.21 g, 7.84 mmol, 33.6% yield) as pale-yellow oil. $_1$H (400 MHz, CDCl$_3$) δ 7.44-7.42 (m, 6H), 7.32-7.28 (m, 6H), 7.26-7.22 (m, 3H), 5.43-5.31 (m, 9H), 5.12-5.10 (m, 1H), 4.35-4.31 (m, 1H), 4.26 (dd, 1H, J=8.0, 4.0), 3.74 (dd, 1H, J=12.0, 4.0), 3.35 (app t, 1H, J=8.0), 3.16 (dd, 1H, J=8.0, 6.0), 2.79 (t, 4H, J=6.0), 2.36 (t, 2H, J=8.0), 2.16-1.99 (m, 10H), 1.65 (p, 2H, J=8.0), 1.40-1.22 (m, 30H), 0.90 (t, 6H, J=6.0). RT=3.95 min. 98.1% purity. ESI-MS: m/z=923 [M+Na]_+ for C$_{60}$H$_{84}$O$_6$Na.

Compound 12:

TFA (0.427 ml, 5.55 mmol) was added to a solution of (±)-11 (2.0 g, 2.219 mmol) and triethylsilane (1.772 ml, 11.09 mmol) in dry DCM (50 ml) at 0° C. under nitrogen atmosphere. The reaction mixture was stirred at 0° C. for 1 h and TLC analysis showed the complete consumption of 11. The mixture was quenched with satd. aq. NaHCO$_3$ solution (50 mL) and extracted with DCM (2×50 mL). The organic layer was dried over anhyd. Na$_2$SO$_4$, filtered and concentrated. The crude product was purified by silica gel (100-200 mesh) column chromatography (Isolera™) using 10% EtOAc in Pet. Ether to afford (±)-12 (1.15 g, 1.745 mmol, 79% yield) as colorless oil. $_1$H (400 MHz, CDCl$_3$) δ 5.43-5.29 (m, 9H), 5.11-5.09 (m, 1H), 4.51 (dd, 1H, J=12.0, 8.0), 4.30 (dd, 1H, J=8.0, 4.0), 4.20-4.16 (m, 2H), 4.11-4.07 (m, 1H), 3.76 (dd, 1H, J=12.0, 4.0), 2.78 (t, 4H, J=6.0), 2.37-2.30 (m, 4H), 2.06 (q, 8H, J=8.0), 1.69-1.62 (m, 4H), 1.40-1.25 (m, 28H), 0.90 (t, 6H, J=6.0). RT=2.29 min. 92.5% purity. ESI-MS: m/z=659 [M+H]_+ for C$_{41}$H$_{71}$O$_6$.

PNI 127 (Alternative Method)

Into a 100 mL two necked round bottomed flask containing a well-stirred solution of 1,4-dimethylpiperidine-4-carboxylic acid hydrochloride (0.970 g, 5.01 mmol) in dry DCM (30 ml), DMAP (0.556 g, 4.55 mmol) and EDCl hydrochloride (1.745 g, 9.10 mmol) were added under nitrogen atmosphere. The reaction mixture was stirred at 25° C. for 10 minutes and a solution of (±)-12 (3 g, 4.55 mmol) in dry DCM (15 mL) was added and the reaction mixture was stirred at 25° C. for 16 hours. After completion of the reaction as indicated by TLC, the solvent was evaporated under reduced pressure. The residue was dissolved in EtOAc (150 mL) and washed with water (2×100 mL), brine (2×100 mL), dried over anhyd. Na$_2$SO$_4$, filtered, concentrated. The crude product was purified by silica gel (100-200 mesh) column chromatography (Isolera™), using 3% MeOH in DCM to provide PNI 127 (2.96 g, 3.71 mmol, 81% yield) as pale-yellow oil.

PNI 574:

Into a 100 mL two necked round bottomed flask containing a stirred solution of 2-(4-methylpiperazin-1-yl)acetic acid (0.125 g, 0.789 mmol) in dry DCM (25 mL), DMAP (0.102 g, 0.789 mmol) and EDCl hydrochloride (0.348 g, 1.821 mmol) were added under nitrogen atmosphere. The reaction mixture was stirred at 25° C. for 10 minutes and a solution of (±)-12 (0.4 g, 0.607 mmol) in dry DCM (5 mL) was added. The mixture was stirred at 25° C. for 16 hours and completion of the reaction was confirmed by TLC analysis. The reaction mixture was quenched with water (120 mL) and extracted with DCM (3×50 mL). The combined organic layers were washed with brine (3×75 mL), dried over anhyd. $Na_2SO_4$, filtered and concentrated under reduced pressure. The crude product was purified by silica gel (100-200 mesh) column chromatography (Isolera™) using 5% MeOH in DCM to give PNI 574 (0.090 g, 0.101 mmol, 16.70% yield) as thick red oil. $_1H$ (400 MHz, $CDCl_3$) δ 5.42-5.30 (m, 9H), 5.13 (s, 1H), 4.33-4.14 (m, 4H), 3.74 (d, 1H, J=4.0), 3.27 (s, 2H), 2.78 (t, 4H, J=6.0), 2.73-2.46 (m 8H), 2.39-2.26 (m, 7H), 2.06 (q, 8H, J=8.0), 1.66-1.58 (m, 4H), 1.49-1.26 (m, 28H), 0.90 (app t, 6H, J=6.0). RT=2.34 min. 93.3% purity. ESI-MS: m/z=800 [M+H]$_+$ for $C_{48}H_{83}N_2O_7$.

PNI 573:

PNI 573 was synthesized using the method similar to the one used for synthesis of PNI 574. Synthesis of PNI 573 was performed using quinuclidine-4-carboxylic acid hydrochloride (0.092 g, 0.592 mmol) in dry DCM (25 mL), DMAP (0.076 g, 0.592 mmol), EDCl hydrochloride (0.304 g, 1.593 mmol), and 12 (0.3 g, 0.455 mmol) in dry DCM (5 mL). The crude product was purified by silica gel (100-200 mesh) column chromatography (Isolera™) using 5% MeOH in DCM to give PNI 573 (0.18 g, 0.226 mmol, 49.7% yield) as pale-yellow oil. $_1H$ (400 MHz, $CDCl_3$) δ 5.42-5.30 (m, 9H), 5.14-5.07 (m, 1H), 4.32-4.23 (m, 3H), 4.11 (dd, 1H, J=12.0, 8.0), 3.76 (dd, 1H, J=12.0, 4.0), 3.24-3.05 (m, 6H), 2.77 (t, 4H, J=6.0), 2.33 (q, 4H, J=8.0), 2.08-1.98 (m, 10H), 1.92 (app t, 4H, J=8.0), 1.66-1.58 (m, 4H), 1.42-1.26 (m, 28H), 0.89 (t, 6H, J=6.0). RT=2.34 min. 92.4% purity. ESI-MS: m/z=796 [M+H]$_+$ for $C_{49}H_{82}NO_7$.

PNI 575:

PNI 575 was synthesized using the method similar to the one used for synthesis of PNI 574. Synthesis of PNI 143 was performed using 1-methylpiperidine-3-carboxylic acid (0.085 g, 0.592 mmol) in dry DCM (25 mL), DMAP (0.076 g, 0.592 mmol), EDCl hydrochloride (0.304 g, 1.593 mmol), and 12 (0.3 g, 0.455 mmol) in dry DCM (5 mL). The crude product was purified by silica gel (100-200 mesh) column chromatography (Isolera™) using 5% MeOH in DCM to give PNI 575 (0.265 g, 0.338 mmol, 74.2% yield) as pale-yellow oil. $_1$H (400 MHz, CDCl$_3$) δ 5.42-5.10 (m, 9H), 5.11 (s, 1H), 4.34-4.12 (m, 4H), 3.77 (d, 1H, J=12.0), 2.99-2.59 (m, 6H), 2.40-2.13 (m, 7H), 2.11-1.84 (m, 11H), 1.80-1.52 (m, 8H), 1.42-1.26 (m, 28H), 0.90 (app t, 6H, J=6.0). RT=2.48 min. 93.2% purity. ESI-MS: m/z=785 [M+H]$_+$ for C$_{48}$H$_{82}$NO$_7$.

Example 9

Synthesis of PNI 576, 577 and 578

Scheme 11. General route for synthesis of PNI 576, 577 and 578

Compound 13:

Compound 13 was synthesized using the method similar to the one used for synthesis of 11. Synthesis of 13 was performed using 4 (9.06 g, 30.5 mmol) in dry DCM (70 mL), DMAP (4.05 g, 33.2 mmol), EDCl hydrochloride (10.15 g, 53.1 mmol), DIPEA (14.28 mL, 80 mmol), and (±)-10 (5.0 g, 13.28 mmol) in dry DCM (30 mL). The crude product was purified by silica gel (100-200 mesh) column chromatography (Isolera™) using 5% EtOAc in Pet. ether to give 13 (11.1 g, 11.89 mmol, 90% yield) as colorless oil. $_1$H (400 MHz, CDCl$_3$) δ 7.46-7.44 (m, 6H), 7.34-7.24 (m, 9H), 5.44 (d, 1H, J=4.0), 5.14-5.12 (m, 1H), 4.37-4.33 (m, 1H), 4.28 (dd, 1H, J=12.0, 4.0), 3.76 (dd, 1H, J=12.0, 4.0), 3.38 (dd, 1H, J=12.0, 8.0), 3.19 (dd, 1H, J=12.0, 8.0), 2.39 (app t, 2H, J=6.0), 2.18-2.02 (m, 2H), 1.67 (p, 2H, J=8.0), 1.50-1.24 (m, 46H), 1.19-1.13 (m, 4H), 0.92 (t, 6H, J=6.0), 0.71-0.65 (m, 4H), 0.62-0.57 (m, 2H), −0.30 (q, 2H, J=6.0).

Compound 14:

Compound 14 was synthesized using the method similar to the one used for synthesis of 12. Synthesis of 14 was performed using (±)-13 (11.0 g, 11.78 mmol) and Et$_3$SiH (9.41 ml, 58.9 mmol) in dry DCM (100 ml), and TFA (1.489 mL, 11.78 mmol). The crude product was purified by silica gel (100-200 mesh) column chromatography (Isolera™) using 10% EtOAc in Pet. ether to give 14 (5.5 g, 7.96 mmol, 67.5% yield) as colorless oil. $_1$H (400 MHz, CDCl$_3$) δ 5.28-5.10 (m, 2H), 4.53-4.07 (m, 3H), 3.78-3.56 (m, 2H), 2.40-2.31 (m, 4H), 1.68-1.59 (m, 4H), 1.38-1.10 (m, 44H), 1.17-1.10 (m, 4H), 0.89 (t, 6H, J=6.0), 0.68-0.62 (m, 4H), 0.59-0.54 (m, 2H), −0.33 (q, 2H, J=6.0). ESI-MS: m/z=691 [M+H]$_+$ for C$_{43}$H$_{79}$O$_6$.

PNI 576:

PNI 576 was synthesized using the method similar to the one used for synthesis of PNI 574. Synthesis of PNI 576 was performed using 1-cyclopropylpiperidine-4-carboxylic acid (0.108 g, 0.637 mmol) in dry DCM (15 mL), DMAP (0.085 g, 0.695 mmol), EDCl hydrochloride (0.222 g, 1.158 mmol), and 14 (0.4 g, 0.579 mmol) in dry DCM (5 mL). The crude product was purified by silica gel (100-200 mesh) column chromatography (Isolera™) using 3% MeOH in DCM to give PNI 576 (0.45 g, 0.534 mmol, 92% yield) as yellow oil. $_1$H (400 MHz, CDCl$_3$) δ 5.35 (s, 1H), 5.10 (s, 1H), 4.31-4.18 (m, 4H), 3.76 (d, 1H, J=12.0), 3.05-2.95 (m, 1H), 2.40-2.12 (m, 7H), 1.93-1.81 (m, 2H), 1.76-1.50 (m, 8H), 1.42-1.26 (m, 44H), 1.19-1.05 (m, 4H), 0.89 (t, 6H, J=6.0), 0.69-0.61 (m, 4H), 0.59-0.54 (m, 2H), 0.48-0.33 (m, 4H), −0.33 (q, 2H, J=6.0). RT=3.35 min. 99.1% purity. ESI-MS: m/z=843 [M+H]$_+$ for C$_{52}$H$_{92}$NO$_7$.

PNI 577:

167

168

PNI 577 was synthesized using the method similar to the one used for synthesis of PNI 574. Synthesis of PNI 577 was performed using 1-ethylpiperidine-4-carboxylic acid (0.104 g, 0.658 mmol) in dry DCM (20 mL), DMAP (0.085 g, 0.658 mmol), EDCl hydrochloride (0.290 g, 1.519 mmol), and 14 (0.35 g, 0.506 mmol) in dry DCM (5 mL). The crude product was purified by silica gel (100-200 mesh) column chromatography (Isolera™) using 5% MeOH in DCM to give PNI 577 (0.29 g, 0.349 mmol, 69.0% yield) as thick colorless oil. $_1$H (400 MHz, CDCl$_3$) δ 5.37-5.35 (m, 1H), 5.13 5.09 (m, 1H), 4.33-4.16 (m, 4H), 3.76 (d, 1H, J=12.0), 2.95-2.90 (m, 2H), 2.51-2.25 (m, 7H), 2.14-1.75 (m 6H), 1.70-1.55 (m, 4H), 1.42-1.28 (m, 44H), 1.17-1.09 (m, 7H), 0.89 (t, 6H, J=6.0), 0.68-0.62 (m, 4H), 0.59-0.54 (m, 2H), –0.33 (q, 2H, J=6.0). RT=3.59 min. 95.1% purity. ESI-MS: m/z=830 [M+H]$_+$ for C$_{51}$H$_{92}$NO$_7$.

PNI 578:

Example 10

Synthesis of PNI 579 and 580

Scheme 12. General route for synthesis of PNI 579 and 580

PNI 578 was synthesized using the method similar to the one used for synthesis of PNI 574. Synthesis of PNI 578 was performed using 2-(1-methylpiperidin-2-yl)acetic acid (0.096 g, 0.608 mmol) in dry DCM (20 mL), DMAP (0.078 g, 0.608 mmol), EDCl hydrochloride (0.290 g, 1.519 mmol), and 14 (0.35 g, 0.506 mmol) in dry DCM (5 mL). The crude product was purified by silica gel (100-200 mesh) column chromatography (Isolera™) using 5% MeOH in DCM to afford PNI 578 (0.32 g, 0.385 mmol, 76% yield) as pale-yellow oil. $_1$H (400 MHz, CDCl$_3$) δ 5.35 (s, 1H), 5.13 (s, 1H), 4.32-4.16 (m, 4H), 3.76 (dt, 1H, J=8.0, 4.0), 2.81-2.18 (m, 12H), 1.77-1.51 (m, 10H), 1.45-1.21 (m, 44H), 1.19-1.10 (m, 4H), 0.89 (t, 6H, J=6.0), 0.68-0.61 (m, 4H), 0.59-0.54 (m, 2H), –0.33 (q, 2H, J=4.0). RT=3.61 min. 99.7% purity. ESI-MS: m/z=853 [M+Na]$_+$ for C$_{51}$H$_{91}$NO$_7$Na.

-continued

-continued

16

Compound 15:

Compound 15 was synthesized using the method similar to the one used for synthesis of 11. Synthesis of 15 was performed using 2-hexyldecanoic acid (3.92 g, 15.27 mmol) in dry DCM (40 mL), DMAP (1.866 g, 15.27 mmol), followed by EDCl hydrochloride (6.37 g, 33.2 mmol), DIPEA (5.80 ml, 33.2 mmol), and (±)-10 (2.5 g, 6.64 mmol) in dry DCM (10 mL). The crude product was purified by silica gel (100-200 mesh) column chromatography (Isolera™) using 2% EtOAc in Pet. ether to give 15 (5.12 g, 6.00 mmol, 90% yield) as pale-yellow oil. $_1$H (400 MHz, CDCl$_3$) δ 7.47-7.45 (m, 6H), 7.33-7.22 (m, 9H), 5.29 (d, 1H, J=4.0), 5.09-5.07 (m, 1H), 4.29-4.24 (m, 2H), 3.75 (dd, 1H, J=8.0, 4.0), 3.42 (dd, 1H, J=12.0, 8.0), 3.22 (dd, 1H, J=12.0, 4.0), 2.43-2.34 (m, 1H), 2.22-2.15 (m, 1H), 1.66-1.38 (m, 8H), 1.36-1.12 (m, 40H), 0.92-0.86 (m, 12H).

Compound 16:

Compound 16 was synthesized using the method similar to the one used for synthesis of 12. Synthesis of 16 was performed using (±)-15 (5.1 g, 5.98 mmol) in dry DCM (70 mL), triethylsilane (4.77 mL, 29.9 mmol), and TFA (1.151 mL, 14.94 mmol). The crude product was purified by silica gel (100-200 mesh) column chromatography (Isolera™) using 2% EtOAc in Pet. ether to give (±)-16 (3.23 g, 5.29 mmol, 88% yield) as colorless oil. $_1$H (400 MHz, CDCl$_3$) δ 5.26 (d, 1H, J=4.0), 5.16 (s, 1H), 4.29 (dd, 1H, J=12.0, 4.0), 4.21-4.17 (m, 1H), 3.80-3.74 (m, 2H), 3.58 (dd, 1H, J=12.0. 4.0), 2.43-2.32 (m, 2H), 2.15 (br s, 1H), 1.67-1.41 (m, 8H), 1.34-1.19 (m, 40H), 0.89 (t, 12H, J=6.0). RT=2.18 min. 99.9% purity. ESI-MS: m/z=611 [M+H]$_+$ for C$_{37}$H$_{71}$O$_6$.

PNI 579:

PNI 579 was synthesized using the method similar to the one used for synthesis of PNI 574. Synthesis of PNI 579 was performed using 1,4-dimethylpiperidine-4-carboxylic acid hydrochloride (0.152 g, 0.786 mmol) in dry DCM (20 mL), DMAP (0.096 g, 0.786 mmol), EDCl hydrochloride (0.301 g, 1.571 mmol), and 16 (0.4 g, 0.655 mmol) in dry DCM (5 mL). The crude product was purified by silica gel (100-200 mesh) column chromatography (Isolera™), using 4% MeOH in DCM to afford PNI 579 (0.444 g, 0.592 mmol, 90% yield) as pale-yellow oil. $_1$H (400 MHz, CDCl$_3$) δ 5.34 (d, 1H, J=4.0), 5.11-5.10 (m, 1H), 4.32-4.27 (m, 3H), 4.21-4.16 (m, 1H), 3.74 (dd, 1H, J=12.0, 4.0), 2.69 (br s, 2H), 2.41-2.31 (m, 5H), 2.22-2.14 (m, 4H), 1.63-1.41 (m, 10H), 1.30-1.22 (m, 43H), 0.88 (t, 12H, J=8.0). RT=2.66 min. 97.4% purity. ESI-MS: m/z=751 [M+H]$_+$ for C$_{45}$H$_{84}$NO$_7$.

PNI 580:

PNI 580 was synthesized using the method similar to the one used for synthesis of PNI 574. Synthesis of PNI 580 was performed using 4-(dimethylamino)butanoic acid hydrochloride (0.165 g, 0.982 mmol) in dry DCM (20 mL), DMAP (0.120 g, 0.982 mmol), EDCl hydrochloride (0.377 g, 1.964 mmol), and 16 (0.4 g, 0.655 mmol) in dry DCM (5 mL). The crude product was purified by silica gel (100-200 mesh) column chromatography (Isolera™), using 4% MeOH in DCM PNI 580 (0.39 g, 0.539 mmol, 82% yield) as colorless oil. $_1$H (400 MHz, CDCl$_3$) δ 5.33 (d, 1H, J=4.0), 5.10 (d, 1H, J=4.0), 4.33-4.21 (m, 4H), 3.75 (dd, 1H, J=8.0, 4.0), 2.42-2.29 (m, 12H), 1.91-1.79 (m, 2H), 1.64-1.41 (m, 8H), 1.34-1.20 (m, 40H), 0.88 (t, 12H, J=6.0). RT=2.49 min. 98.7% purity. ESI-MS: m/z=724 [M+H]$_+$ for C$_{43}$H$_{82}$NO$_7$.

Example 11

Synthesis of PNI 581, 582 and 583

J=6.0), 2.06 (q, 8H, J=8.0), 1.59 (p, 4H, J=4.0), 1.43-1.23 (m, 32H), 0.91-0.88 (m, 6H). RT=3.86 min. 98.1% purity. ESI-MS: m/z=896 [M+Na]$_+$ for C$_{60}$H$_{88}$O$_4$Na.

Compound 18:

To a stirred solution of 17 (2.35 g, 2.69 mmol) and Et$_3$SiH (2.149 ml, 13.45 mmol) in DCM (40 mL) in 250 mL two Scheme 13. General route for synthesis of PNI 581, 582 and 583

Compound 17:

To a stirred solution of 10 (2.0 g, 5.31 mmol) in dry DMF (100 mL) and dry THF (100 mL) in 500 mL three necked RBF under nitrogen atmosphere at 0° C., NaH (1.062 g, 26.6 mmol) was added slowly to it and the reaction mixture was stirred at same temperature for 15 minutes. Then, linoleyl bromide (5.25 g, 15.94 mmol) was added to it and reaction mixture was slowly warmed to 25° C., and stirred for 7 hrs. After completion of the reaction as indicated by TLC, reaction mixture was quenched with ice cold water (250 mL) and extracted with EtOAc (3×120 mL). The combined organic layer was washed with brine (3×150 mL), dried over Na$_2$SO$_4$, filtered and concentrated to obtain the crude. The crude product was purified by silica gel (100-200 mesh) column chromatography (Isolera™), using 3% EtOAc in Pet. ether to give 17 (2.4 g, 2.75 mmol, 51.7% yield) as pale-yellow oil. $_1$H (400 MHz, CDCl$_3$) δ 7.49-7.45 (m, 6H), 7.30-7.20 (m, 9H), 5.42-5.31 (m, 8H), 4.22-4.18 (m, 1H), 4.04 (dd, 1H, J=8.0, 4.0), 3.91-3.86 (m, 1H), 3.84 (d, 1H, J=4.0), 3.73 (dd, 1H, J=12.0, 4.0), 3.50-3.43 (m, 2H), 3.39-3.28 (m, 3H), 3.22 (dd, 1H, J=12.0, 8.0), 2.78 (t, 4H, necked RBF under nitrogen atmosphere was added TFA (0.427 mL, 5.55 mmol) at 0° C. and the reaction mixture was stirred at 0° C. for 1 h. After completion of the reaction as indicated by TLC, reaction mixture was quenched with satd. NaHCO$_3$ solution (60 mL) and extracted with DCM (2×50 mL). The organic layer was dried over Na$_2$SO$_4$, filtered, and concentrated to obtain the crude. The crude product was purified by silica gel (100-200 mesh) column chromatography (Isolera™), using 8% EtOAc in Pet. ether) to give 18 (1.46 g, 2.314 mmol, 86% yield) as colorless oil. $_1$H (400 MHz, CDCl$_3$) δ 5.42-5.30 (m, 8H), 4.13 (dd, 1H, J=8.0, 4.0), 4.09-4.05 (m, 1H), 3.96-3.92 (m 2H), 3.90-3.81 (m, 2H), 3.75 (dd, 1H, J=12.0, 4.0), 3.64-3.59 (m, 1H), 3.47-3.42 (m, 3H), 2.78 (t, 4H, J=6.0), 2.06 (q, 8H, J=8.0), 1.62-1.48 (m, 4H), 1.40-1.26 (m, 32H), 0.90 (t, 6H, J=6.0). RT=2.63 min. 99.9% purity. ESI-MS: m/z=631 [M+H]$_+$ for Cal H$_{75}$O$_4$.

PNI 581:

To a stirred solution of 1,4-dimethylpiperidine-4-carboxylic acid (0.120 g, 0.762 mmol) in dry DCM (20 mL) in 100 mL two necked RBF under nitrogen atmosphere, DMAP (0.072 g, 0.586 mmol) and EDCl hydrochloride (0.281 g, 1.466 mmol) were added and reaction mixture stirred at 25° C. for 10 minutes. Then, 18 (0.37 g, 0.586 mmol) in dry DCM (5 mL) was added to the reaction mixture and stirred at 25° C. for 16 h. TLC showed majority of unreacted starting materials. Once again to a stirred solution of 1,4-Dimethylpiperidine-4-carboxylic acid hydrochloride (0.148 g, 0.762 mmol) in dry DCM (10 mL) in 100 mL two necked RBF under nitrogen atmosphere, DMAP (0.072 g, 0.586 mmol) and EDCl hydrochloride (0.281 g, 1.466 mmol) were added and reaction mixture was stirred at 25° C. for 10 minutes. Then to this mixture, the first reaction mixture was added, and reaction mixture was stirred at room temperature for 16 h. After completion of the reaction as indicated by TLC, the solvent was evaporated to obtain the residue. This residue was dissolved in EtOAc (130 mL) and washed with water (2×100 mL), brine (2×100 mL). The organic layer was dried over $Na_2SO_4$, filtered and concentrated to obtain the crude. The crude product was purified by silica gel (100-200 mesh) column chromatography (Isolera™), using 4% MeOH in DCM to give PNI 581 (0.395 g, 0.501 mmol, 86% yield) as brown oil. $_1$H (400 MHz, $CDCl_3$) δ 5.42-5.31 (m, 8H), 4.44-4.38 (m, 1H), 4.30-4.26 (m, 1H), 4.22-4.18 (m, 1H), 4.07 (dd, 1H, J=8.0, 4.0), 3.93 (s, 1H), 3.85 (d, 1H, J=4.0), 3.75 (d, 1H, J=8.0), 3.60-3.54 (m, 1H), 3.45 (t, 2H, J=6.0), 3.41-3.36 (m, 1H), 3.26 (br s, 2H), 2.84-2.71 (m, 6H), 2.65 (s, 3H), 2.32-2.22 (m, 2H), 2.06 (q, 8H, J=8.0), 1.68-1.48 (m, 6H), 1.38-1.26 (m, 35H), 0.90 (t, 6H, J=6.0). RT=4.06 min. 97.8% purity. ESI-MS: m/z=771.2 [M+H]$_+$ for $C_{49}H_{88}NO_5$.

PNI 582:

PNI 582 was synthesized using the method similar to the one used for synthesis of PNI 574. Synthesis of PNI 582 was performed using 1-methylpiperidine-3-carboxylic acid (0.113 g, 0.792 mmol) in dry DCM (20 mL), DMAP (0.097 g, 0.792 mmol), EDCl hydrochloride (0.304 g, 1.585 mmol), and 18 (0.4 g, 0.634 mmol) in dry DCM (5 mL). The crude product was purified by silica gel (100-200 mesh) column chromatography (Isolera™), using 5% MeOH in DCM to give PNI 582 (0.43 g, 0.569 mmol, 90% yield) as pale-yellow oil. $_1$H (400 MHz, $CDCl_3$) δ 5.42-5.30 (m, 8H), 4.38-4.34 (m, 1H), 4.23-4.14 (m, 2H), 4.08 (dd, 1H, J=12.0, 4.0), 3.92 (s, 1H), 3.83 (s, 1H), 3.77 (d, 1H, J=12.0), 3.58-3.53 (m, 1H), 3.45 (t, 2H, J=8.0), 3.42-3.36 (m, 1H), 3.17 (br s, 1H), 2.93 (br s, 1H), 2.78 (t, 4H, J=8.0), 2.60-2.26 (m, 4H), 2.17-1.96 (m, 10H), 1.87-1.74 (m, 2H), 1.67-1.49 (m, 6H), 1.38-1.26 (m, 32H), 0.90 (t, 6H, J=6.0). RT=2.99 min. 99.2% purity. ESI-MS: m/z=756.6 [M+H]$_+$ for $C_{48}H_{86}NO_5$.

PNI 583:

PNI 583 was synthesized using the method similar to the one used for synthesis of PNI 574. Synthesis of PNI 583 was performed using 2-(4-methylpiperazin-1-yl)acetic acid (0.125 g, 0.792 mmol) in dry DCM (20 mL), DMAP (0.097 g, 0.792 mmol), EDCl hydrochloride (0.304 g, 1.585 mmol), and 18 (0.4 g, 0.634 mmol) in dry DCM (5 mL). The crude product was purified by silica gel (100-200 mesh) column chromatography (Isolera™), using 4% MeOH in DCM to give PNI 583 (0.415 g, 0.527 mmol, 83% yield) as pale-yellow oil. $_1$H (400 MHz, CDCl$_3$) δ 5.41-5.30 (m, 8H), 4.41 (dd, 1H, J=12.0, 4.0), 4.25-4.16 (m, 2H), 4.09 (dd, 1H, J=8.0, 4.0), 3.92 (s, 1H), 3.83 (d, 1H, J=4.0), 3.76 (dd, 1H, J=12.0, 4.0), 3.58-3.52 (m, 1H), 3.44 (t, 2H, J=8.0), 3.41-3.36 (m, 1H), 3.28 (s, 2H), 2.84-2.58 (m, 12H), 2.43 (s, 3H), 2.06 (q, 8H, J=8.0), 1.57-1.51 (m, 4H), 1.40-1.26 (m, 32H), 0.92-0.86 (m, 6H). RT=2.68 min. 97.9% purity. ESI-MS: m/z=771.6 [M+H]$_+$ for C$_{48}$H$_{87}$N$_2$O$_5$.

Example 12

Synthesis of PNI 76

Scheme 14. Synthesis of PNI 76

PNI 76

-continued

HCl salt of PNI 76

PNI 76:

To a solution of (±)-19 (600 mg, 3.65 mmol) in dry DMF (10 mL), DMAP (cat.) was added followed by addition of a solution of 4-(dimethylamino)butanoic acid hydrochloride (1.56 g, 9.3 mmol) in dry DMF (10 mL) under $N_2$ atmosphere. $CH_2Cl_2$ (10 mL) was added to the reaction mixture. Solid EDCl hydrochloride (1.39 g, 7.30 mmol) was then added to the reaction mixture and was stirred at room temperature for 4 h. TLC analysis of the reaction mixture shows complete consumption of (±)-19. Further, DMAP (cat.) was added to the reaction mixture followed by addition of Myristic acid (2.73 g, 11.98 mmol) dissolved in dry DMF (10 mL) and EDCl hydrochloride (3.50 g, 18.25 mmol) as solid. Next, dry DCM (10 mL) was added and the reaction mixture was stirred overnight at room temperature. The reaction mixture was concentrated over rotary evaporator, diluted with EtOAc (20 mL) and washed with water (3×10 mL). Organic layer was washed with brine, dried over anhydrous $Na_2SO_4$ and evaporated to dryness over rotary evaporator to provide crude mixture which was purified by silica gel column chromatography using 5% MeOH/DCM as the eluent. PNI 76 was obtained as colorless oil (294 mg, 0.32 mmol) in 9% overall yield.

HCl Salt of PNI 76:

PNI 76 was dissolved in a minimum amount of anhyd. diethyl ether. HCl in ether was added to it until pH becomes 3-5 (checked by pH paper). The solvent was evaporated, and $CH_2Cl_2$ was added and evaporated 2-3 times in order to remove traces of HCl. Next, the compound was dissolved in a small amount of deionized water and it was lyophilized to get HCl salt of PNI 76. $_1$H (500 MHz, CDCl$_3$) δ 5.38 (d, 1H, J=3.0 Hz), 5.22-5.19 (m, 1H), 5.07 (d, 1H, J=5.0 Hz), 4.61 (d, 1H, J=10.0 Hz), 4.26 (dd, 1H, J=10.0 Hz, 5.0 Hz), 4.21 (dd, 1H, J=10.0 Hz, 5.0 Hz), 4.13 (dd, 1H, J=15.0 Hz, 5.0 Hz), 3.79 (d, 1H, J=10.0 Hz), 2.42-2.29 (m, 14H), 2.23 (apparent t, 2H, J=7.5 Hz), 1.84 (p, 2H, J=6.3 Hz), 1.65-1.54 (m, 6H), 1.30-1.27 (m, 60H), 0.89 (apparent t, 9H, J=7.5 Hz). Molecular weight for $C_{54}H_{102}NO_9$ [M+H]$_+$ Calculated 908.7555. Found 908.7511.

Example 13

Synthesis of PNI 369

Scheme 15. Synthesis of PNI 369

-continued

22

23

PNI 369

Compound 21:

To a stirred solution of 2-(dodecyloxy)ethanol (20, 3.7 g, 16.06 mmol) and triphenylphosphine (10.53 g, 40.1 mmol) in dry toluene (70 mL), carbon tetrabromide (13.31 g, 40.1 mmol) was added slowly and the reaction mixture was stirred at 60° C. for 16 h. After completion of the reaction as indicated by TLC analysis, the reaction mixture was concentrated under reduced pressure and the crude product was purified by silica gel (100-200 mesh) column chromatography (Isolera™) using 5% EtOAc in Pet. ether to afford 1-(2-bromoethoxy)dodecane (21, 4.55 g, 15.20 mmol, 95% yield) as colorless oil. $_1$H (400 MHz, CDCl$_3$) δ 3.74 (d, 2H, J=6.0), 3.50-3.45 (m, 4H), 1.59 (p, 2H, J=8.0), 1.38-1.21 (m, 18H), 0.89 (t, 3H, J=6.0). RT=3.40 min. 96.6% purity.

Compound 22:

Compound 22 was synthesized using the method similar to the one used for synthesis of 17. Synthesis of 22 was performed using 10 (1.0 g, 2.66 mmol) in dry DMF (10 mL) and dry THF (10 mL), sodium hydride (0.531 g, 13.28 mmol, 60% dispersion in mineral oil), and 1-(2-bromoethoxy)dodecane (21, 2.337 g, 7.97 mmol). The crude product was purified by silica gel (100-200 mesh) column chromatography (Isolera™) using 5% EtOAc in Pet. ether to give 22

(1.1 g, 1.373 mmol, 51.7% yield) as colorless oil. $_1$H (400 MHz, CDCl$_3$) δ 7.46 (d, 6H, J=8.0), 7.30-7.20 (m, 9H), 4.25-4.21 (m, 1H), 4.06-4.02 (m, 2H), 4.00 (d, 1H, J=4.0), 3.79-3.75 (m, 1H), 3.72-3.58 (m, 5H), 3.52-3.46 (m, 3H), 3.41-3.28 (m, 5H), 3.22 (d, 1H, J=8.0, 4.0), 1.60 (t, 2H, J=6.0), 1.48 (p, 2H, J=8.0), 1.35-1.21 (m, 36H), 0.89 (t, 6H, J=6.0). RT=2.63 min. 97.8% purity. ESI-MS: m/z=823.5 [M+Na], for C$_{52}$H$_{80}$O$_6$Na.

Compound 23:

Compound 23 was synthesized using the method similar to the one used for synthesis of 18. Synthesis of 23 was performed using 22 (1.1 g, 1.373 mmol) and Et$_3$SiH (1.096 mL, 6.86 mmol) in dry DCM (30 mL), and TFA (0.264 mL, 3.43 mmol). The crude product was purified by silica gel (100-200 mesh) column chromatography (Isolera™) using 20% EtOAc in Pet. ether to give 23 (0.58 g, 1.038 mmol, 76% yield) as colorless oil. $_1$H (400 MHz, CDCl$_3$) δ 4.15-4.03 (m, 4H), 3.87-3.76 (m, 4H), 3.66-3.54 (m, 7H), 3.47-3.43 (m, 4H), 1.61-1.54 (m, 4H), 1.36-1.20 (m, 36H), 0.90-0.87 (m, 6H). RT=1.97 min. 99.1% purity. ESI-MS: m/z=559.5 [M+H]$_+$ for C$_{33}$H$_{67}$O$_6$.

PNI 369

PNI 369 was synthesized using the method like the one used for synthesis of PNI 574. Synthesis of PNI 369 was performed using 1,4-dimethylpiperidine-4-carboxylic acid (0.110 g, 0.698 mmol) in dry DCM (25 mL), DMAP (0.086 g, 0.698 mmol), EDCl hydrochloride (0.359 g, 1.879 mmol), and 23 (0.3 g, 0.537 mmol) in dry DCM (5 mL). The crude product was purified by silica gel (100-200 mesh) column chromatography (Isolera™) using 5% MeOH in DCM to afford PNI 369 (0.21 g, 0.301 mmol, 56.0% yield) as pale-yellow oil. $_1$H (400 MHz, CDCl$_3$) δ 4.37-4.28 (m, 2H), 4.21-4.17 (m, 1H), 4.11-4.07 (m, 2H), 3.99 (d, 1H, J=4.0), 3.81-3.76 (m, 1H), 3.73-3.69 (m, 1H), 3.66-3.59 (m, 3H), 3.57-3.52 (m, 4H), 3.46-3.41 (m, 4H), 2.89 (br s, 2H), 2.48-2.35 (m, 5H), 2.21 (d, 2H, J=12.0), 1.86-1.71 (m, 2H), 1.60-1.52 (m, 4H), 1.37-1.20 (m, 39H), 0.88 (t, 6H, J=8.0). RT=2.13 min. 98.5% purity. ESI-MS: m/z=698.6 [M+H]$_+$ for C$_{41}$H$_{80}$NO$_7$.

Example 14

Schemes for Synthesis of Representative Compounds

Scheme 16. Scheme for synthesis of PNI 326, 327, 335, 624, and 625

Scheme 17. Alternative route for synthesis of PNI 326, 327, 335, 624, and 625
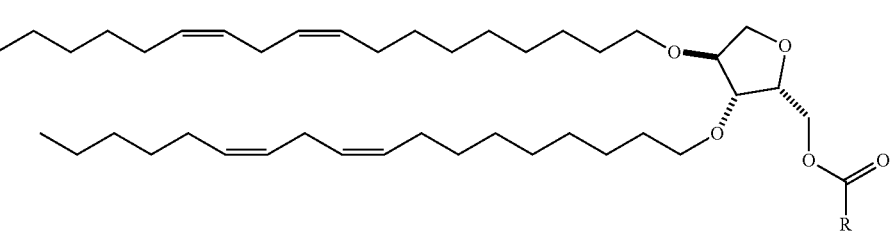

-continued

R =

PNI 626

PNI 627

PNI 628

PNI 629

PNI 630

PNI 631

PNI 632

Scheme 19. Scheme for syntheis of PNI 633, 634, 635, 636, and 637

$(\pm)$-1

EDCl, DMAP
———————
CH$_2$Cl$_2$, DMF

Oleic acid
EDCl, DMAP
———————
CH$_2$Cl$_2$, DMF

R =

PNI 633

PNI 634

PNI 635

PNI 636

PNI 637

Scheme 20. Alternative route for synthesis of PNI 633, 634, 635, 636, and 637

Scheme 21. Scheme for synthesis of PNI 638, 639, 640, 641, and 642

Scheme 22. Scheme for synthesis of PNI 343, 643, 644, and 645

-continued
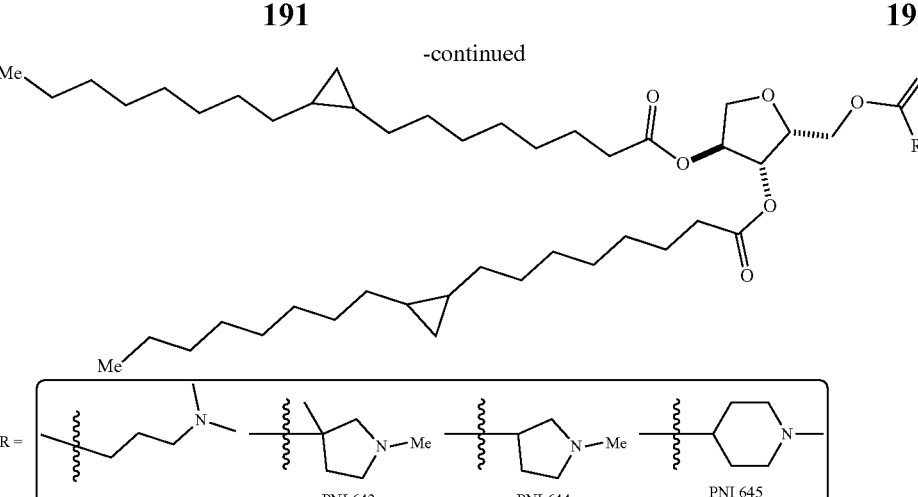
Scheme 23. Scheme for synthesis of PNI 646, 647, 648, 649, and 650

-continued
R =
PNI 646
PNI 647
PNI 648
PNI 649
PNI 650
-continued
R =
PNI 656
PNI 657
PNI 658
Scheme 24. Scheme for synthesis of PNI 656, 657, and 658
(±)-1
HO
R
EDCl, DMAP
CH₂Cl₂, DMF
5
EDCl, DMAP
CH₂Cl₂, DMF
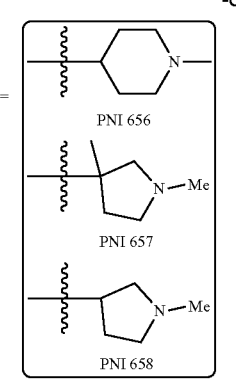
Scheme 25. Scheme for synthesis of PNI 659, 660, 661, 662, and 663
8
1. LiAlH₄
2. CBr₄, PPh₃
10
NaH
31

195

-continued

196

-continued

32

Et₃SiH
TFA

R =

PNI 659

PNI 660

PNI 661

PNI 662

PNI 663

33

$$\underset{\text{R}}{\overset{\text{O}}{\|}}\text{C}-\text{OH}$$
EDCl
DMAP

Scheme 26. Scheme for synthesis of PNI 364, 365, 368, 372, and 373

23

$$\underset{\text{R}}{\overset{\text{O}}{\|}}\text{C}-\text{OH}$$
EDCl
DMAP

-continued

R =

PNI 364

PNI 365

PNI 368

PNI 372

PNI 373

Scheme 27. Scheme for synthesis of PNI 670, 671, 672, 673, and 674

(±)-1

EDCl, DMAP
CH$_2$Cl$_2$, DMF

Stearic acid
EDCl, DMAP
CH$_2$Cl$_2$, DMF

R =

PNI 670

PNI 671

PNI 672

PNI 673

PNI 674

Scheme 21. Scheme for synthesis of PNI 675, 676, 677, 678, and 679

Scheme 29. Scheme for synthesis of 38

Linoleic acid

36

-continued

37

$\xrightarrow{\text{LiOH}}$

38

Scheme 30. Scheme for synthesis of PNI 340, 341, 680, 681, 682, and 683

(±)-1

$\xrightarrow[\text{CH}_2\text{Cl}_2, \text{DMF}]{\text{EDCl, DMAP}}$ $\xrightarrow[\text{CH}_2\text{Cl}_2, \text{DMF}]{\begin{array}{c}38\\ \text{EDCl, DMAP}\end{array}}$

R =

PNI 340          PNI 341

PNI 680          PNI 681

PNI 682          PNI 683

Scheme 31. Scheme for synthesis of PNI 684, 685, 686, 687, and 688

38

$\xrightarrow[\text{2. CBr}_4, \text{PPh}_3]{\text{1. LiAlH}_4}$

-continued

R =

PNI 684

PNI 685

PNI 686

PNI 687

PNI 688

Example 15

Isolation of Primary T Cells From Human Whole Blood And Expansion

Unless otherwise noted, all reagents were purchased from STEMCELL Technologies, Vancouver, Canada.

Lyophilized human IL-2 was reconstituted to a concentration of 0.1 mg/mi in sterile 1×PBS without calcium or magnesium in a biological safety cabinet. Adding 50 µl of this human IL-2 to 50 mL of ImmunoCult-XF™ T Cell Expansion Medium generated the medium for T cells. 7-30 mL of Human Whole Peripheral Blood with ACDA anticoagulant was placed in a sterile 50 mL polypropylene conical tube in a biological safety cabinet.

Negative Selection Protocol. Blood was drawn from healthy human donors and combined with ACD-A, an anticoagulant. A pan T cell negative selection kit, EasySep™ direct human T cell isolation kit was used to isolate both CD4+ and CD8+ T cells. The cells were maintained in ImmunoCult-XF™ T Cell Exp Medium supplemented with human recombinant IL2 (Peprotech). On the day of isolation, the cells were activated with a triple activator, ImmunoCult™ Human CD3/CD28/CD2 T Cell Activator.

Positive selection Protocol. Blood was drawn from healthy human donors and combined with ACDA, an anticoagulant. A PBMC suspension was prepared using density gradient centrifugation through the use of Lymphoprep™. T cells were then positively selected from the PBMC suspension using EasySep™ Human CD3 Pos Selection Kit II. The cells were maintained in ImmunoCult-XF™ T Cell Exp Medium supplemented with human recombinant IL2 (Peprotech). On the day of isolation, the cells were activated with a triple activator, ImmunoCult™ Human CD3/CD28/ CD2 T Cell Activator.

T cells were isolated from the blood using an EasySep™ Direct Human T Cell Isolation Kit. First 500/mL of Isolation Cocktail™ and then 500/mL of the EasySep™ RapidSpheres™ were added to the tube of blood. Blood was mixed gently and incubated at room temperature (RT) for 5 minutes. The tube was placed into an EasySep™ 50 Magnet™ apparatus and incubated at RT for 10 minutes. The enriched cell suspension was pipetted into a new sterile 50 mL polypropylene tube, and the RapidSpheres™ process repeated.

This doubly enriched cell suspension was pipetted into a new sterile 50 mL polypropylene conical tube and centrifuged for 10 min at 300 g at RT.

Supernatant was removed and the cell pellet was resuspended in 10 mL of PBS and respun at 300 g for 10 min to wash any remaining supernatant from the cells. The supernatant was again removed and the cells resuspended in pre-warmed complete T cell media. A sample was drawn, and a Trypan blue exclusion test of cell viability was performed (Thermo Fisher).

Example 16

Activation/Expansion of T Cells

The scientific background for activating T cells may be found in the 2003 paper by Trickett A. et al. 6 The cell suspension of Example 8 was diluted in Complete T Cell media (ThermoFisher) to 1E6 cells/ml, and the T cells activated by adding 250 of either ImmunoCult™ Human CD3/CD28/CD2 triple T Cell Activator™ or ImmunoCult™ Human CD3/CD28 dual T Cell Activator™ per mL of T cell media. Cell growth was monitored by a daily cell count under magnification. Cells were diluted with Complete T Cell media to maintain concentrations of about 1E6 cells/ mL. On about day 5, 6 or 7, the T cells entered log phase of growth, and a rapid expansion occurred.

To confirm that the T cells were in log phase, CD25 expression was assessed and needed to be greater than 80% by flow cytometry (BD Biosciences) and the expansion of the cells were monitored by graphing the total number of T cells over time (not shown).

Example 17

Downstream Processing and Analysis of Treated T Cells: Flow Cytometry and ELISA

Reagents were from Stemcell Technologies unless otherwise stated. Tcells were isolated from a single donor. At 48 h following lipid particle mRNA exposure, the treated T cells were harvested by transferring the cell suspensions to pre-labeled 1.5 mL tubes and centrifuged 300×g at 4 degrees C. for 10 minutes. Supernatant was removed and the pellet resuspended in PBS. An amount of 0.5 ul of BD Horizon™ Fixable Viability Stain 575V™ (BD Biosciences), was added, and the mixture incubated in the dark for 10 minutes at RT. This stain binds to amines.

The cells were centrifuged again as before, then washed twice with 1 mL of stain buffer (BSA, BD Pharminigen), and the washed pellet was diluted in 100 µl BSA. The following antibodies were added to each tube of treated cells in 2 µl volumes: CD25, CD8, CD4, (PerCP-Cy™ 5.5 Mouse Anti Human CD25, BV786 Mouse Anti-Human CD8 Clone RPA-T8, APC-Cy™7 Mouse Anti-Human CD4 Clone SK3 (all from BD Pharmingen) with the exception of the controls: in the eGFP only sample and viability control, no antibody was added. In the single stain compensation tubes, only one antibody per tube was added.

The tubes were incubated at 4 degrees C. for 30 min, whereupon 4000 of stain buffer was added, and the cells were centrifuged again. Cells were washed once with 1 mL of stain buffer and spun down again as in step one. Cell pellets were resuspended in 1 mL of stain buffer and added to pre-labeled flow tubes with cell strainer caps (Corning Falcon).

Negative Selection Protocol. Blood was drawn from healthy human donors and combined with ACDA, an anticoagulant. A pan T cell negative selection kit, EasySep™ direct human T cell isolation kit was used to isolate both CD4+ and CD8+ T cells. The cells were maintained in ImmunoCult-XF™ T Cell Experimental Medium supplemented with human recombinant IL2 (Peprotech). On the day of isolation, the cells were activated with a triple activator, ImmunoCult™ Human CD3/CD28/CD2 T Cell Activator.

Freezing and Thawing of Human T cells. Blood was drawn from healthy human donors and combined with ACDA, an anticoagulant. A pan T cell negative selection kit, EasySep Direct human T cell isolation kit was used to isolate both CD4+ and CD8+ T cells. Cells were cryopreserved using CryoStor® CS10 and stored in liquid nitrogen. At the time of thaw, cells were maintained in ImmunoCult-XF™ T Cell Exp Medium supplemented with human recombinant IL2 (Peprotech). On the day of thaw, the cells were activated with a triple activator, After transfection, flow cytometry was used to general eGFP expression levels as well as Median Fluorescence Intensity values for the studies.

Example 18

Microfluidic Mixing of Nucleic Acid Therapeutics (NAT) into Lipid Particles (LNP)

N/P=10 was used for all these experiments except when otherwise noted. Lipid mix composition solutions were prepared in ethanol by combining prescribed amounts of lipids (see Table 3) from individual lipid stocks in ethanol. For the NanoAssembl® SPARK™, a lipid mix solution concentration of 37.5 mM was used, and for the NanoAssembl® Benchtop or Ignite™, a lipid mix solution of 12.5 mM was typically used.

TABLE 3

| Identifier | Lipid Mix Compositions for Use with the IL of the Invention |
| --- | --- |
| Lipid mix A | 50 mol % IL/10 mol % DSPC/37.5 mol % Cholesterol/2.5 mol % Polyoxyethylene (40) stearate) |
| Lipid mix D | 40 mol % IL/40 mol % DOPE/17.5 mol % Cholesterol/2.5 mol % polyoxyethylene (40) stearate |

TABLE 3-continued

| Identifier | Lipid Mix Compositions for Use with the IL of the Invention |
|---|---|
| Lipid mix G | 40 mol % IL/30 mol % DOPE/17 mol % Cholesterol/10 mol % Triglyceride/2.5 mol % polyoxyethylene (40) stearate |
| Lipid mix H | 40 mol % IL/20 mol % DOPE/17.5 mol % Cholesterol/20 mol % Triglyceride/2.5 mol % polyoxyethylene (40) stearate |
| Lipid mix J | 40 mol % IL/40 mol % DOPE/O mol % Cholesterol/17.4 mol % Triglyceride/2.5 mol % polyoxyethylene (40) stearate |
| LM TBD | 40 mol % IL/20 mol % DOPE/37.5 mol % Cholesterol/2.5 mol % Tridecyl-D-maltoside |
| LM T20 | 40 mol % IL/20 mol % DOPE/37.5 mol % Cholesterol/2.5 mol % Tween 20 |
| LM T80 | 40 mol % IL/20 mol % DOPE/37.5 mol % Cholesterol/2.5 mol % Polysorbate 80 |
| Lipid MixK | 40 mol % IL/20 mol % DOPE/37.5 mol % Cholesterol/2.5 mol % Lipid H |
| Lipid Mix L | 40 mol % IL/20 mol % DOPE/35.9 mol % Cholesterol/4 mol % Lipid H |
| LM02 | 50 mol % IL/10 mol % DSPC/38.5 mol % Cholesterol/1.5 mol % PEG-DMG |
| LM02b | 50 mol % IL/10 mol % DOPE/38.5 mol % Cholesterol/1.5 mol % PEG-DMG 2000 |
| LM02c | 50 mol % IL/10 mol % DSPC/38.5 mol % Cholesterol/1.5 mol % PEG-DMG 2000 |
| LMV1 | 47.5 mol % IL/12.5 mol % DOPE/38.5 mol % Cholesterol/1.5 mol % PEG-DMG 2000 |
| LMV2 | 47.5 mol % IL/12.5 mol % DSPC/38.5 mol % Cholesterol/1.5 mol % PEG-DMG 2000 |
| S9 | 50 mol % IL/10 mol % DSPC/37.5 mol % Cholesterol/2.5 mol % BRIJ ™ S20 |
| S10 | 50 mol % IL/10 mol % DSPC/40 mol % Cholesterol/2.5 mol % TPGS1000 |
| S11 | 50 mol % IL/10 mol % DSPC/37.5 mol % Cholesterol/2.5 mol % BRIJ ™ S10 |
| S11C | 50 mol % IL/10 mol % DSPC/38.5 mol % Cholesterol/1.5 mol % BRIJ ™ S10 |
| S12 | 50 mol % IL/10 mol % DSPC/37.5 mol % Cholesterol/2.5 mol % BRIJ ™ L4 |
| CT7 | 50 mol % IL/10 mol % DSPC/38.5 mol % Cholesterol/1.5 mol % Polysorbate 80 |
| CT7C | 50 mol % IL/10 mol % DSPC /37.5 mol % Cholesterol/2.5 mol % Polysorbate 80 |
| CT7B | 50 mol % IL/10 mol % DSPC/39.5 mol % Cholesterol/0.5 mol % Polysorbate 80 |
| CT10 | 40 mol % IL/20 mol % DSPC/37.5 mol % Cholesterol/2.5 mol % BRIJ ™ S10 |
| CT14 | 40 mol % IL/20 mol % DSPC/39.5 mol % Cholesterol/0.5 mol % TPGS1000 |
| CT15 | 40 mol % IL/20 mol % DSPC/39.5 mol % Cholesterol/0.5 mol % BRIJ ™ S10 |
| CT22 | 40 mol % IL/20 mol % DSPC/38.5 mol % Cholesterol/1.5 mol % Polysorbate 80 |
| CT34 | 40 mol % IL/20 mol % DSPC/39.5 mol % Cholesterol/0.5 mol % BRIJ ™ S20 |
| C12-200 | 50 mol % C12-200/10 mol % DSPC/38.5 mol % Cholesterol/1.5 mol % PEG-DMG |

IL = ionizable lipid;
Tween80 = Polysorbate 80;
BRIJ ™ L4 = Polyoxyethylene (4) lauryl ether;
BRIJ ™ S10 = Polyoxyethylene (10) stearyl ether;
BRIJ ™ S20 = Polyoxyethylene (20) stearyl ether;
BRIJ ™ S35 = Polyoxyethylene (23) lauryl ether;
TPGS 1000 = D-α-Tocopherol polyethylene glycol 1000 succinate;
Lipid H = Tween 20/Polysorbate 80/Tridecyl-D-maltoside in equal ratios;
Stabilizing Agent = any stabilizing agent including PEG-DMG or as defined in the Description supra under that category.

Components of the Lipid Mixes include the ionizable lipid, structural lipid, cholesterol and stabilizing agent. Low pH buffers (3-6) may be used. For ionizable aminolipids, the pH of the buffer is typically below the pKa of the lipid.

SiRNA, Messenger RNA or plasmid NAT preparation is described below. Observed particle attributes were generally sized from 50-200 nm for mRNA, depending on lipid composition.

Messenger RNA or plasmid NAT was diluted using sodium acetate buffer to the required concentration. Lipid nucleic acid particle samples were then prepared by running both fluids using the NanoAssemblr® Spark instrument. Briefly, 10-20 µg of nucleic acids in 100 mM sodium acetate buffer in a total volume of 3 µL was mixed with 16 µL of 37.5 mM lipid mix solution as required by the N/P ratios (4, 6 or 10 in illustrated examples). The lipid nucleic acid particles made in the instrument were immediately diluted down with 48 µL Ca and Mg free 1×PBS at pH 7.4 in the aqueous output well. These nucleic acid lipid particles were immediately collected into microcentrifuge tubes containing 96 µL of Ca and Mg free 1×PBS at pH 7.4. Encapsulation efficiency was measured by a modified Ribogreen™ assay (Quanti-iT RiboGreen™ RNA assay kit, Fisher). Observed particle attributes were generally sized from 60-200 nm for mRNA, depending on lipid composition and method of production.

Lipid based formulations were also manufactured by a larger instrument, the NanoAssemblr® Ignite™ for testing. Briefly, 350 µL of mRNA was diluted using 100 mM sodium acetate buffer to the required concentration of 0.2 to 0.3 mg/mL. Lipid particle samples were then prepared by running both fluids, namely, nucleic acids in aqueous solvent and Lipid Mix in ethanol at a flow ratio of 3:1 and at a total flow rate of 12 ml/minute. Following mixing in the microfluidic device, the lipid nucleic acid particle (LNAP) sample was diluted into RNAse-free tubes containing three to 40 volumes of phosphate buffered saline (PBS) buffer, pH 7.4. Ethanol was finally removed through dialysis in PBS, pH 7 or using Amicon™ centrifugal filters (Millipore, USA) at 3000 RPM, or using TFF systems. Once the required concentration was achieved, the lipid nucleic acid particles were filter sterilized using 0.2 µm filters in aseptic conditions. Final encapsulation efficiency was measured by Ribogreen™ assay.

Nucleic Acid Reagents. Messenger RNA or plasmid nucleic acid therapeutic (NAT) as described below, was diluted using sodium acetate buffer to the required concentration. LNAP samples were then prepared by running both fluids using the NanoAssemblr® Spark instrument. Briefly, 10-20 µg of nucleic acids in 100 mM sodium acetate buffer in a total volume of 32 µL was mixed with 16 µL of 37.5 mM lipid mix solution as required by the N/P ratios (4, 6, 8, 10 in illustrated examples). The microfluidically mixed LNAP made in the instrument were immediately diluted down with 48 µL Ca++ and Mg++ free 1×PBS at pH 7.4 in the aqueous output well. These LNAP were immediately collected into microcentrifuge tubes containing 96 µL of the same buffer at pH 7.4. Encapsulation efficiency was measured by a modified Ribogreen™ assay (Quanti-iT RiboGreen™ RNA assay kit, Fisher). This information was used to establish the desired dosage.

The nucleic acid therapeutic model reagents used in the following experiments were:

Trilink Cleancap® eGFP mRNA: Cat. L-7601 (Trilink Biotechnologies, San Diego, CA); Trilink Cleancap® EPO mRNA: Cat. L-7209 (Trilink Biotechnologies); Millipore Sigma TagRFP Simplicon RNA Kit: Cat. SCR712 (contains both TagRFP RNA & B18R RNA) (Millipore Sigma Canada, Oakville Ontario); CD19 CAR plasmid with EGFP reporter was purchased from Creative Biolabs (Shirley, NY) and contains a T7 promoter (Mut)-signal peptide-scFv-CD8 hinge transmembrane-4-1BB-CD3zeta-T2A-eGFP reporter gene CAR cassette (2353 bp) within the pcDNA. The total size of this custom CD19 CAR plasmid DNA template is around 7649-7661 bp.

An unmodified CAR messenger RNA (mRNA) transcript encoding the CD19 scFv-h (BB±-eGFP reporter gene cassette was synthesized by in vitro transcription with wild-type bases and capped (Cap 1) using CleanCap® AG methodology by Trilink Biotechnologies Inc. This unmodified CAR mRNA transcript was enzymatically polyadenylated followed by a DNase and Phosphatase treatment. The final mRNA transcript product was silica membrane purified and packaged in a solution of 1 mM Sodium Citrate buffer (pH 6.4) at concentration of 1 mg/mL. This custom CD19 CAR plasmid vector and CD19 CAR encoding mRNA were purchased from Creative Biolab and Trilink Biotechnologies Inc respectively.

OVA antigen has utility in vaccine research as it has been used as a model antigen to stimulate immune response[10]. Usually OVA antigen is used with a sensitizing agent such as Alum, but when OVA antigen is delivered in the mRNA form, the hypothesis is that sensitizing agents such as Alum are not needed, and mRNA itself is able to produce the response to the antigen by the immune cells. CleanCap® OVA mRNA L-7610 and CleanCap® OVA mRNA (5moU) L-7210 were used.

Plasmid preparation: pCX-EGFP Plasmid size 5514 nt, custom made by GenScript USA Inc, Piscataway, NJ, including ampicillin resistance, restriction enzyme HINDIII, in ddH2O, was used for this assessment. The plasmid included a GFP expressing component which produces target protein only when the plasmid is expressed within a cell.

Example 19

Comparative Data of Lipids Showing Activity with eGFP mRNA LNPs in Primary Human T Cells Reagents were acquired from Abcam, Cambridge, UK unless otherwise stated. The eGFP SimpleStep™ ELISA®

Kit was used to demonstrate mRNA delivery and activity in vitro. The assay was performed as directed by the eGFP SimpleStep ELISA® Kit protocol. Briefly; frozen human T cells, previously isolated from fresh human whole blood using a negative selection protocol, were thawed and activated using a triple activator. Ten days post-activation, T cells were dosed with N/P 10 mRNA LNPs encoding eGFP at 2 pg mRNA per 500,000 cells. After 48 hours of treatment with mRNA LNPs the T cells were harvested and lysed for total eGFP content.

In order to expose the isolated and activated T cells (Day 0) to the formulated mRNA, 2 ug of CleanCap™ eGFP (Trilink Biotechnologies, San Diego, CA) mRNA-containing LNP was added to 500,000 T cells in 1 mL of complete T cell media, with 1 ug/mL of Recombinant Human ApoE4 ("ApoE") (Peprotech Inc., Montreal, Canada).

Positive control was standard Lipid (DLin-MC3-DMA or "MC3" lipid data) using the Trio activation Protocol.

LNP was calculated based upon earlier Ribogreen™ assay results. T cells were counted through Trypan blue (Sigma) exclusion and diluted to 500,000 cells/mL. Briefly, in a 12 well plate, 1 mL was aliquoted into each well. ApoE was added to a final concentration of 1 ug/mL in each well. Based upon the calculation in step 1, the required amount of mRNA LNP was added (day 7), and the plate incubated for 48 h.

Lipid mix compositions were tested for their ability to induce transfection as measured by median fluorescence intensity of labeled mRNA in T cells (as measured by flow cytometry). Primary human T cells, fresh isolation from human blood, were selected by a negative selection method and treated with a dose of 2 µg of mRNA per 500,000 cells.

Ionizable lipids, PNI 76, 119, 121 and MC3 were compared in a composition of 40 Mol % ionizable lipid, 20 Mole % structural lipid DSPC, 37.5 Mol % cholesterol, and 2.5 Mol % BRIJ™ S10, and at an N/P ratio of 10.

The transfection efficiency and quantity of expressed eGFP for each of the lipids is shown in the fifth and sixth column respectively, in Table 4. FIG. 1 shows the performance of LNPs containing either PNI 76 or PNI 121 against ionizable lipid Dlin-MC3-DMA (MC3) in a CT10 composition at an N/P ratio of 10, and analyzed for gene expression by flow cytometry 48 hours after treatment for eGFP mRNA expression. It was found that PNI 76 had equal transfection efficiency as MC3 while that of PNI 121 was greater than MC3.

Figure 2:
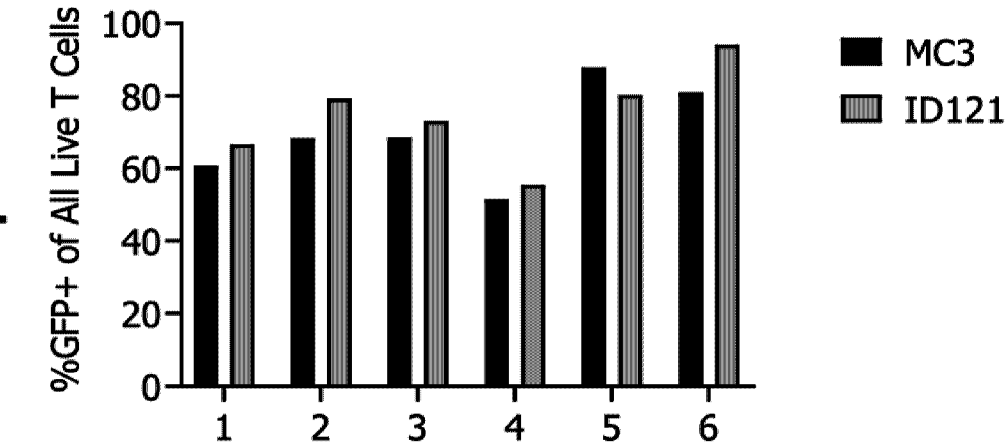
FIG. 2 is a graph illustrating percent GFP expression 48 h post treatment, in isolated primary human T cells mediated by mRNA-LNPs containing lipid MC3 or PNI lipid 121 in a CT10 composition at an N/P ratio of 10. The X axis represents six different donors.

In a related experiment, primary human T cells from six different donors were isolated from fresh whole blood using a negative selection protocol and activated using a triple activator, then treated with mRNA LNPs 7 days post activation. Gene expression was analyzed by flow cytometry 48 hours after treatment and the results are shown in FIG. 2. It was found that the transfection efficiency of LNPs containing PNI 121 was greater than those containing clinically validated MC3 in various donors. The viability of T cells was unaffected by their treatment with PNI 121 as compared to untreated cells (not shown).

Figure 3:
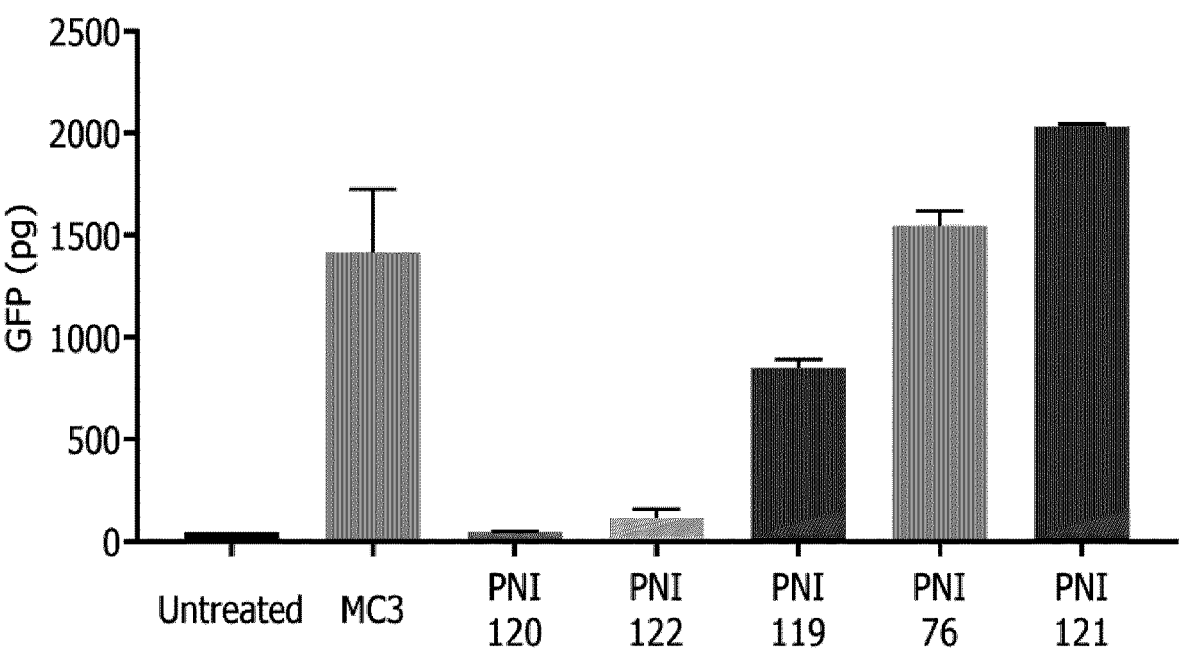
FIG. 3 is a bar graph illustrating quantification of eGFP expression determined by ELISA following treatment of CD4+/CD8+ T cells with eGFP mRNA LNP comprising DLin-MC3-DMA, PNI 76, PNI 119, PNI 120, PNI 121, and PNI 122 in a CT10 composition at an N/P ratio of 10.

Furthermore, the level of eGFP expression was quantified by eGFP ELISA as shown in FIG. 3. Frozen human T cells, previously isolated from fresh human whole blood using a negative selection protocol, were thawed and activated using a triple activator. At 10 days post-activation, T cells were dosed with CT10 mRNA LNPs LNP comprising DLin-MC3-DMA, PNI 76, PNI 119, PNI 120, PNI 121, and PNI 122 encoding eGFP at 2 pg mRNA per 500,000 cells and N/P 10. Protein expression was measured after 48 hours by eGFP ELISA. It was found that all PNI novel lipids mediated eGFP expression. Most notably, the eGFP expression mediated by PNI 121 was greater than that of MC3.

Figure 4:
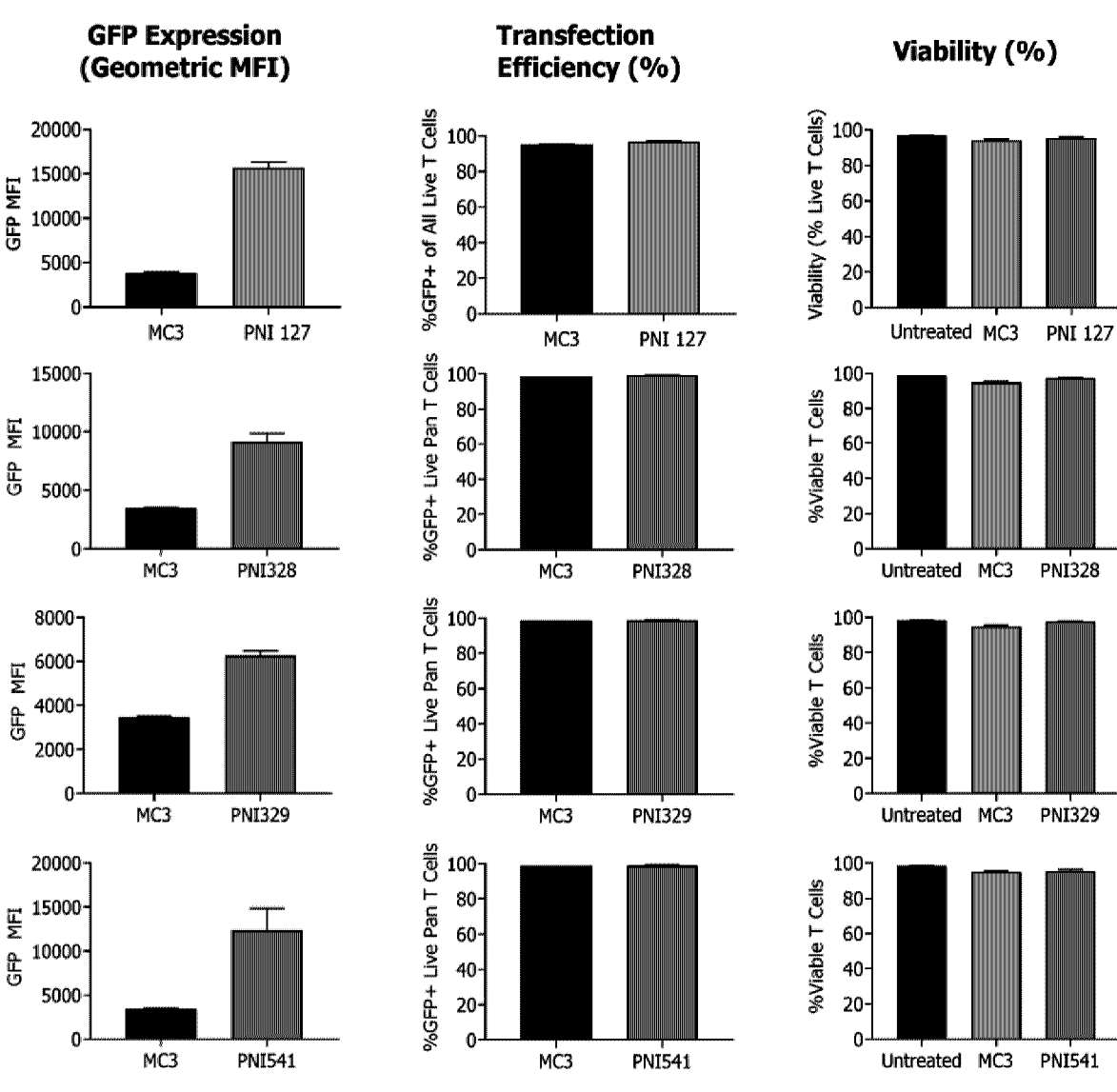
FIG. 4 is a bar graph showing GFP expression in isolated primary human previously cryopreserved T cells treated 4 days after activation with 500 ng of encapsulated mRNA per 125,000 cells by mRNA-LNPs containing either DLin-MC3-DMA, PNI 127, PNI 328, PNI 329, or PNI 541, in a CT10 composition, with an N/P ratio of 8. GFP MFI (first column), transfection efficiency (middle column), and viability (third column) were measured by flow cytometry 48 h after LNP addition.

In a related experiment, GFP expression in isolated primary human previously cryopreserved T cells treated 4 days after activation with 500 ng of encapsulated mRNA per 125,000 cells by mRNA-LNPs containing either DLin-MC3-DMA, PNI 127, PNI 328, PNI 329, or PNI 541, in a CT10 composition, with an N/P ratio of 8. GFP MFI (first column), transfection efficiency (middle column), and viability (third column) were measured by flow cytometry 48 h after LNP addition in FIG. 4.

Figure 5:
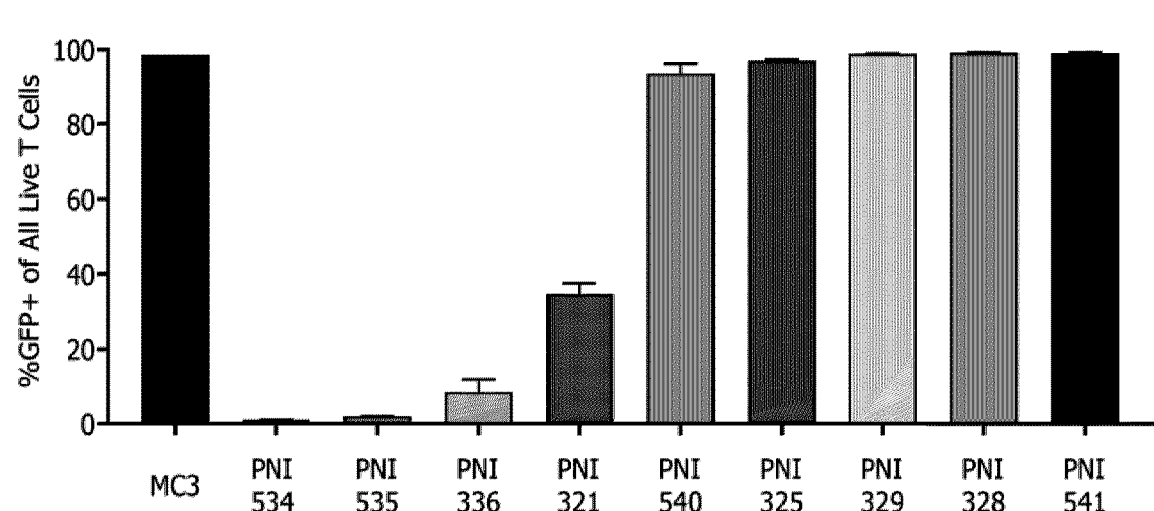
FIG. 5 shows two bar graphs illustrating GFP expression in isolated primary human T cells mediated by mRNA-LNPs containing ionizable lipid Dlin-MC3-DMA, or each of several novel ionizable lipid PNI Lipids (PNI 321, 325, 328, 329, 336, 534, 535, 540, 541), in a CT10 composition and an N/P ratio of 8, treatment 3 days post T cell activation with 500 ng encapsulated mRNA per 125,000 T cells. Transfection efficiency (upper) and MFI (lower) were measured by flow cytometry 48 h after LNP addition.
Figure 5:
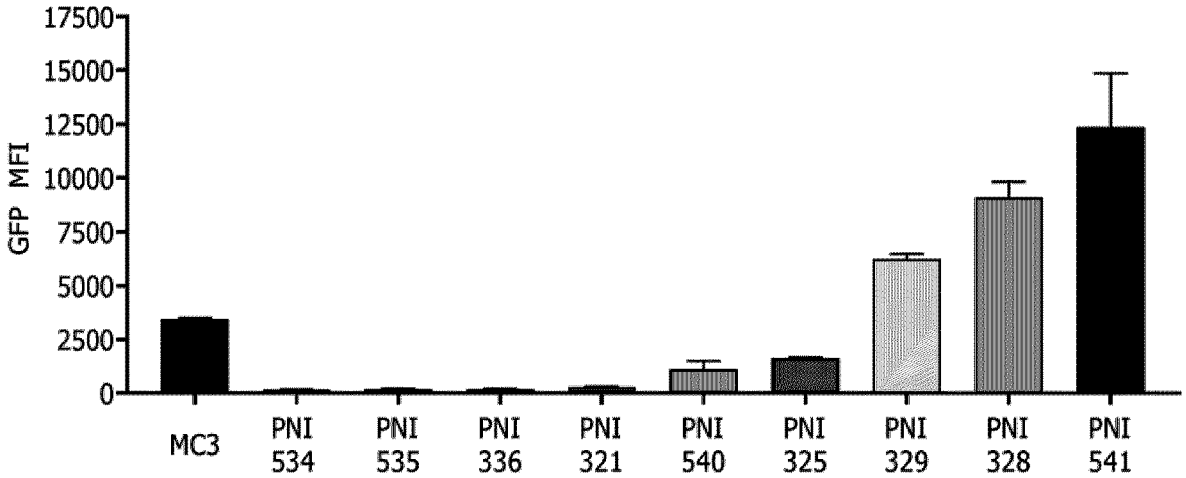

GFP MFI was measured by flow cytometry 48 hours after LNP addition. T cells were isolated from whole blood using a negative isolation procedure (EasySep™ Human T Cell Isolation Kit, Stemcell Technologies). T cells were dosed with mRNA-LNPs 3 days after activation with 500 ng of encapsulated mRNA per 125,000 cells. The LNP were CT10 compositions with an N/P of 8. The results are shown in FIG. 5. Transfection efficiency (upper graph) and MFI (lower graph) were measured by flow cytometry 48 h after LNP addition. PNI 328, 329 and 541 show higher levels of protein expression than MC3 (MFI).

Table 4 shows the quantitative results for an additional experiment with MC3, PNI 76, PNI 119 and PNI 121 eGFP mRNA LNPS in CT10 at N/P 8.

TABLE 4

| | | | | | | |
|---|---|---|---|---|---|---|
| over all: Activity of Nucleic Acid LNPs Manufactured on the NanoAssemblr® Spark | | | | | | |

| No. | ID | pKa Ex.[2] | % eGFP + | eGFP (pg) | Fold Change Relative to MC3 | Structure |
|---|---|---|---|---|---|---|
| 1 | MC 3 | 5.99 | 58.95 | 1370.0 | 1 | |
| 2 | PNI 76 | 6.42 | 62.35 | 1502.0 | 1.095 | |
| 3 | PNI | 7.48 | — | 807.0 | 0.589 | |
| 4 | PNI 119 | 6.83 | 74.4 | 1986.0 | 1.449 | |

[2]Determined by TNS assay.

Example 20

Erythropoietin mRNA Delivery and Expression

Figure 6:
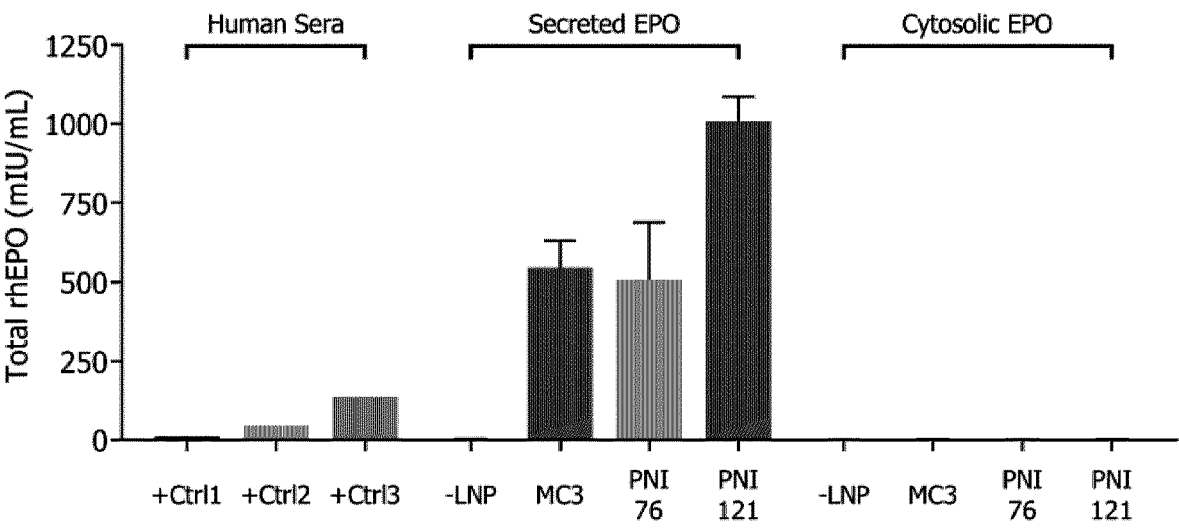
FIG. 6 is a bar graph illustrating expression levels of secreted and cytosolic recombinant human erythropoietin (EPO) determined by ELISA following mRNA LNP mediated transfection of pan T cells comparing untreated control ("-LNP"), DLin-MC3-DMA, PNI 76 or PNI 121 in LM02 composition at N/P 10. Controls were normal human sera standards provided by the manufacturer.

The Quantikine® IVD Human Epo ELISA double-antibody sandwich assay was used to demonstrate mRNA delivery and activity in vitro. Reagents were acquired from Quantikine, Minneapolis, MN. The assay was performed as directed on the Quantikine® IVD® ELISA Human Erythropoietin Immunoassay protocol. REF DEP00 Package Insert. Briefly; primary human T cells were isolated from fresh whole blood using a negative selection protocol and activated using a triple activator. Seven days post-activation, T cells were dosed with mRNA LNPs encoding EPO at 2 pg mRNA per 500,000 cells and N/P 10. Quantikine® Human Serum Controls were used. After 48 hours of treatment with mRNA LNPs the T cells were harvested and lysed for cytosolic EPO and media supernatant was sampled for secreted EPO. The results are shown in FIG. 6 in mIU/mL. Table 5 includes the data of FIG. 6 as well as the fold increase of EPO for PNI 76 and 121 versus MC3. It was found that EPO expression mediated by LNPs containing PNI 121 was higher than those containing MC3.

TABLE 5

Comparative data of lipids showing activity with EPO mRNA

| No. | ID | pKa Exp. | EPO concentration (mIU/mL) | EPO Fold Change Relative to MC3 |
|---|---|---|---|---|
| 1 | MC3 | 5.99 | 545.2 | 1.0 |
| 2 | PNI 76 | 6.42 | 507.3 | 0.93 |
| 3 | PNI 121 | 6.83 | 1009.0 | 1.86 |

Figure 7:
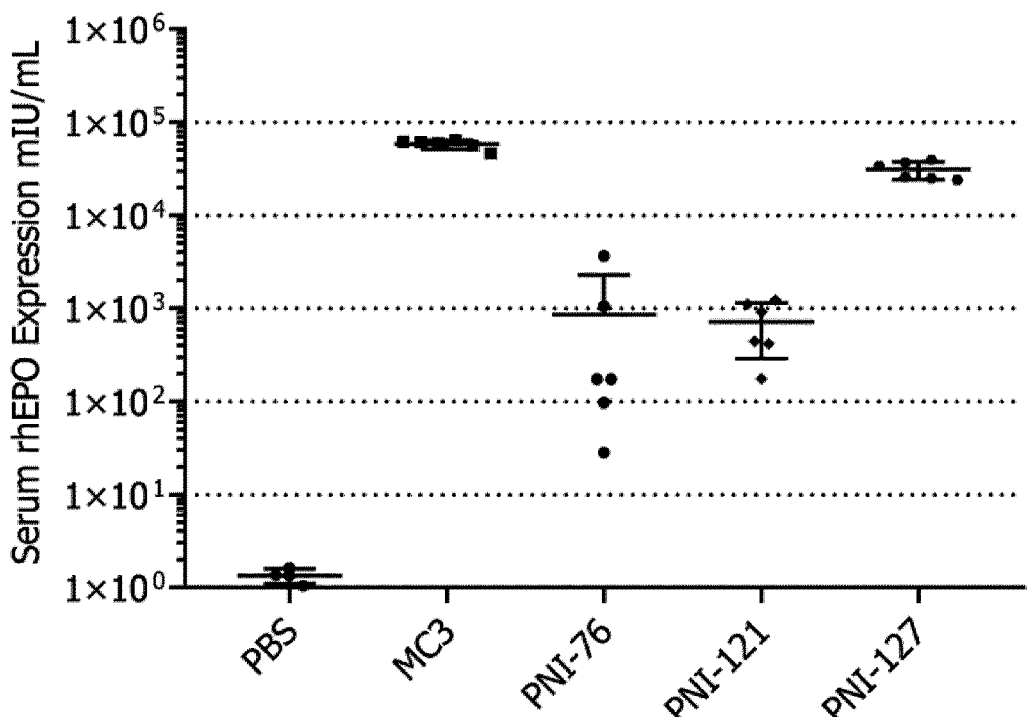
FIG. 7 shows EPO expression level in $C_{56}BL/6$ mice following i.v administration of 0.5 mg/Kg dose of recombinant human EPO-encoded mRNA LNPs containing ionizable lipids DLin-MC3-DMA, PNI-76, PNI 121, or PNI 127 in a LM02 composition at N/P 6.
Figure 8:
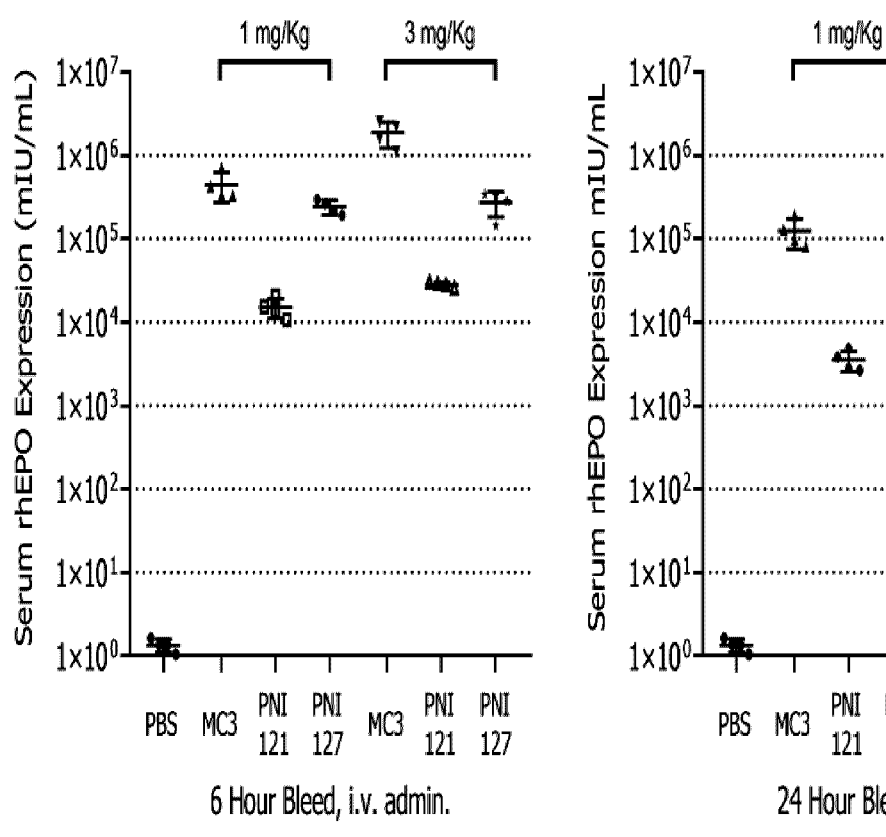
FIG. 8 shows EPO expression levels 6 h (left) and 24 h (right) in $C_{56}BL/6$ mice following i.v administration of 1 or 3 mg/Kg dose of recombinant human EPO-encoded mRNA LNPs containing ionizable lipids DLin-MC3-DMA, PNI 121, or PNI 127 using LM02 composition at N/P 6. PBS was used as negative control.

C56BL/6 mice were administered i.v doses of 0.5, 1 or 3 mg/Kg of recombinant human EPO-encoded mRNA LNPs containing ionizable lipids MC3, PNI 76, PNI 121 and PNI 127 using the LM02 composition at N/P 6; hEPO protein was measured using Quantikine® IVD® ELISA Human Erythropoietin Immunoassay protocol. Results for the 0.5 mg/Kg dosage are shown in the scatter plot of FIG. 7. Results for the 1 and 3 mg/Kg doses are shown in FIG. 8 as scatter plots of hEPO expression levels at 6 h (left) and 24 h (right).

Figure 9:
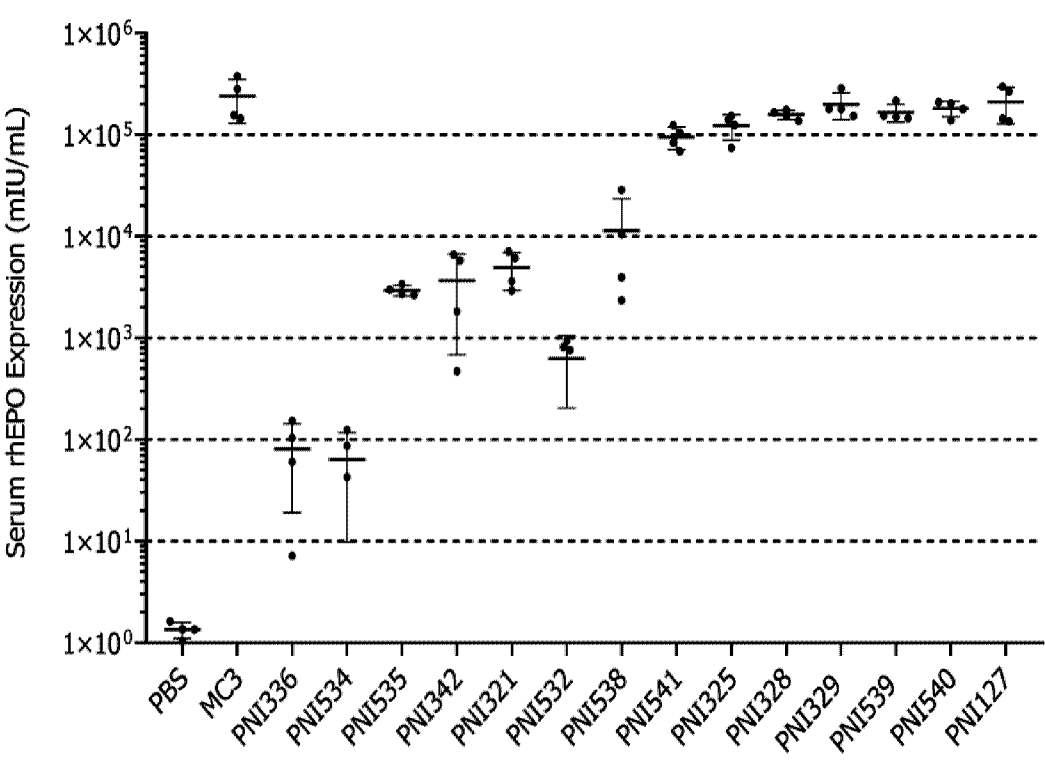
FIG. 9 is a scatter plot showing the EPO expression levels in mIU/mL 6 h after administration of 5-moU EPO mRNA encapsulated in LM02 LNAP (LNP) comprising a variety of 15 ionizable lipid compounds (PNI 336, PNI 534, PNI 535, PNI 342, PNI 321, PNI 532, PNI 538, PNI 541, PNI 325, PNI 328, PNI 329, PNI 539, PNI 540, PNI 127) at an N/P ratio of 6 and a dose of 0.5 mg/Kg.

In another study, 5-moU EPO mRNA encapsulated in LM02 LNP at an N/P ratio of 6 and a dose of 0.5 mg/Kg comprising a variety of 15 ionizable lipids (PNI 336, PNI 534, PNI 535, PNI 342, PNI 321, PNI 532, PNI 538, PNI 541, PNI 325, PNI 328, PNI 329, PNI 539, PNI 540, PNI 127); along with MC3 as a control, were administered. hEPO protein was measured using ProteinSimple® Ella platform, and the rhEPO microfluidic cartridges provided by the manufacturer. The results are shown in FIG. 9, in which several of the PNI compounds (PNI 328, 329, 539, 540 and 127) compare well to MC3. PNI-127, PNI-329, PNI 541 and PNI-565 are better than MC3 in terms of the amount of protein produced (Higher MFIs than MC3)

Example 21

Lipid Nucleic Acid Particle or "LNP" Characterization and Encapsulation

After the lipid particles were made as described supra, particle size (hydrodynamic diameter of the particles) was determined by Dynamic Light Scattering (DLS) using a ZetaSizer™ Nano ZS™ (Malvern Instruments, UK). He/Ne laser tuned to 633 nm wavelength was used as the light source. Data were measured from the scattered intensity data conducted in backscattering detection mode (measurement angle=173). Measurements were an average of 10 runs of two cycles each per sample. Z-Average size was reported as the particle size, and is defined as the harmonic intensity averaged particle diameter.

Physical characteristics of lipid nanoparticle (LNP) compositions comprising compounds according to Formula (I) and that were manufactured on the NanoAssemblr® Spark and Benchtop, are shown in Tables 6 and 7 below. Size, size variation of the LNP (PDI), encapsulation efficiency, and pKa are shown. The physical characteristics of these LNP are important from a standpoint of stability, biodistribution, and cell membrane crossing. There was good encapsulation in all the formulations, with polydispersity (PDI) under 0.3. Size and PDI were measured using dynamic light scattering techniques, and nucleic acid encapsulation efficiency was calculated from a modified Quant-iT RiboGreen RNA assay.

TABLE 6

GFP-encoded LNPs comprising various synthesized ionizable lipids were manufactured using NanoAssemblr ® microfluidic mixer. A CT10 composition with N/P 8 was used. Size, PDI and encapsulation efficiency of GFP-encoded LNPs

| PNI Lipid ID | Diameter (Z. ave, nm) | Polydispersity Index (PDI) | Encapsulation Efficiency (%) |
|---|---|---|---|
| MC3 | 77.2 | 0.11 | 88.6 |
| PNI 121 | 100.7 | 0.16 | 87.3 |
| PNI 127 | 115.8 | 0.24 | 88.9 |
| PNI 321 | 68.6 | 0.07 | 92.4 |
| PNI 325 | 121.5 | 0.39 | 51.1 |
| PNI 328 | 92.6 | 0.16 | 92.5 |
| PNI 329 | 74.1 | 0.11 | 93.2 |
| PNI 336 | 79.6 | 0.07 | 86.6 |
| PNI 534 | 107.1 | 0.29 | 49.3 |
| PNI 535 | 133.1 | 0.07 | 91.7 |
| PNI 540 | 60.6 | 0.08 | 93.5 |
| PNI 541 | 109.4 | 0.28 | 73.5 |

Table 7

EPO mRNA encapsulating LNPs comprising various synthesized ionizable lipids were manufactured using NanoAssemblr ® microfluidic mixer. A composition according to LM02 with N/P 6 was used in each case. Size, PDI and Encapsulation Efficiency of EPO encoded LNPS

| PNI Lipid ID | Diameter (Z. ave, nm) | Polydispersity Index (PDI) | Encapsulation Efficiency (%) |
|---|---|---|---|
| MC3 | 65.1 | 0.04 | 98.8 |
| PNI 76 | 83.1 | 0.16 | 88.9 |
| PNI 121 | 93.5 | 0.10 | 98.8 |
| PNI 122 | 102.4 | 0.15 | 99.3 |
| PNI 127 | 77.7 | 0.09 | 97.2 |
| PNI 325 | 65.3 | 0.09 | 95.9 |
| PNI 541 | 73.8 | 0.06 | 97.1 |
| PNI 321 | 60.0 | 0.09 | 94.9 |
| PNI 534 | 75.0 | 0.15 | 89.4 |
| PNI 539 | 86.9 | 0.13 | 88.2 |
| PNI 540 | 65.7 | 0.05 | 88.1 |
| PNI 329 | 70.9 | 0.04 | 94.4 |
| PNI 342 | 58.2 | 0.04 | 97.2 |
| PNI 532 | 144.3 | 0.15 | 37.3 |
| PNI 535 | 54.2 | 0.11 | 82.2 |
| PNI 336 | 64.3 | 0.06 | 89.8 |
| PNI 328 | 66.9 | 0.02 | 96.2 |
| PNI 538 | 67.0 | 0.11 | 98.7 |

Example 22 hEPO/Cytokines Measurement by Simplex™ Automated ELISA

Figure 10:
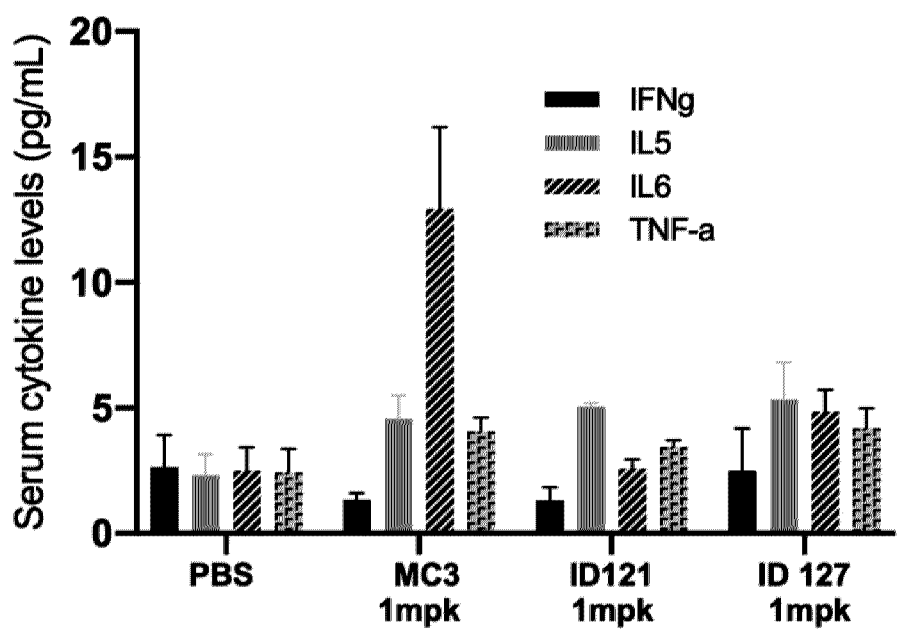
FIG. 10 Shows various cytokine levels: IFNg, IL-5, IL-6, and TNF-α, measured by ELLA™ Simple Plex™ automated ELISA (Protein Simple) in mice 48 h after i.v. administration of 1 mg/kg (mpk) of 5 moU rhEPO-encoded mRNA mediated by LNPs of LM02 composition at N/P 6 containing ionizable lipid MC3, PNI 121, or PNI 127. PBS was the negative control.

Blood from mice treated with hEPO mRNA LNP was analyzed using an automated ELISA platform "ELLA", using Simplex™ antibody panel cartridges. Human-specific EPO and mouse-specific IL-5, IL-6, TNF-α, and IFN-γ were measured (reagents from Bio-techne). Briefly, 50 µL of sample reagent (diluted biological sample, quality control, or calibration point sample) were aliquoted into each sample inlet, and 1 mL of wash buffer was added into corresponding inlets on the cartridge. All immunoassay operations (including prime system, flow samples and split them into channels, sample incubation, wash, rehydrate and flow secondary antibody, wash, rehydrate and flow streptavidin dye conjugate, incubate, wash, scan) were processed automatically. Raw signal levels (relative fluorescence units, RFUs), mean signal values, standard deviation, and coefficient of variance (CV) for each glass nanoReactor (GNR) value are provided. RFU values are automatically backfit by the ELLA to produce an analyte concentration per analyte/sample using the manufacturer given calibration methodology. Results are shown in FIG. 10.

The Quantikine® IVD Human Epo ELISA double-antibody sandwich assay was used to demonstrate mRNA delivery and activity in vivo. Reagents were acquired from Quantikine, Minneapolis, MN. The assay was performed as directed on the Quantikine® IVD® ELISA Human Erythropoietin Immunoassay protocol REF DEP00 Package Insert. Briefly; Sera samples of 6 h, and/or 24 h post intravenous administration of 0.5, 1 or 3 mg/kg dose of EPO-encoded mRNA were analyzed for EPO expression analysis, and expressed as mIU/mL. To an EPO antibody pre-coated 96-well microplate, provided by the manufacturer, standards, appropriately diluted sera, and the Horseradish peroxidase (HRP)-conjugated rabbit anti-EPO polyclonal antibody and TMB (Tetramethylbenzidine) as the substrate were added and incubated for 20 minutes. Stop solution (Sulfuric Acid) was added to the wells and the plate was read at 450 nm and the concentration of EPO was calculated. The amount of colour generated is directly proportional to the amount of the conjugate bound to EPO antibody, which in turn is directly proportional to the amount of EPO in the specimen or standard. A standard curve was generated by plotting absorbance versus concentration of provided standards. Quantikine® Human Serum Controls (CEP 01, CEP 03) were used for internal controls.

Example 23

CD19 CAR Expression in Isolated Primary Human T Cells Mediated by mRNA-LNPs

MRNA containing IL with CT10 composition at N/P 8 was assayed after in vitro exposure. The CAR vector pcDNA3.1 anti-CD19-h(BB Lambda)-EGFP-2nd-CAR (T7 Mut) 7661 bp was purchased from Creative BioLabs, NY, USA.

Figure 11:
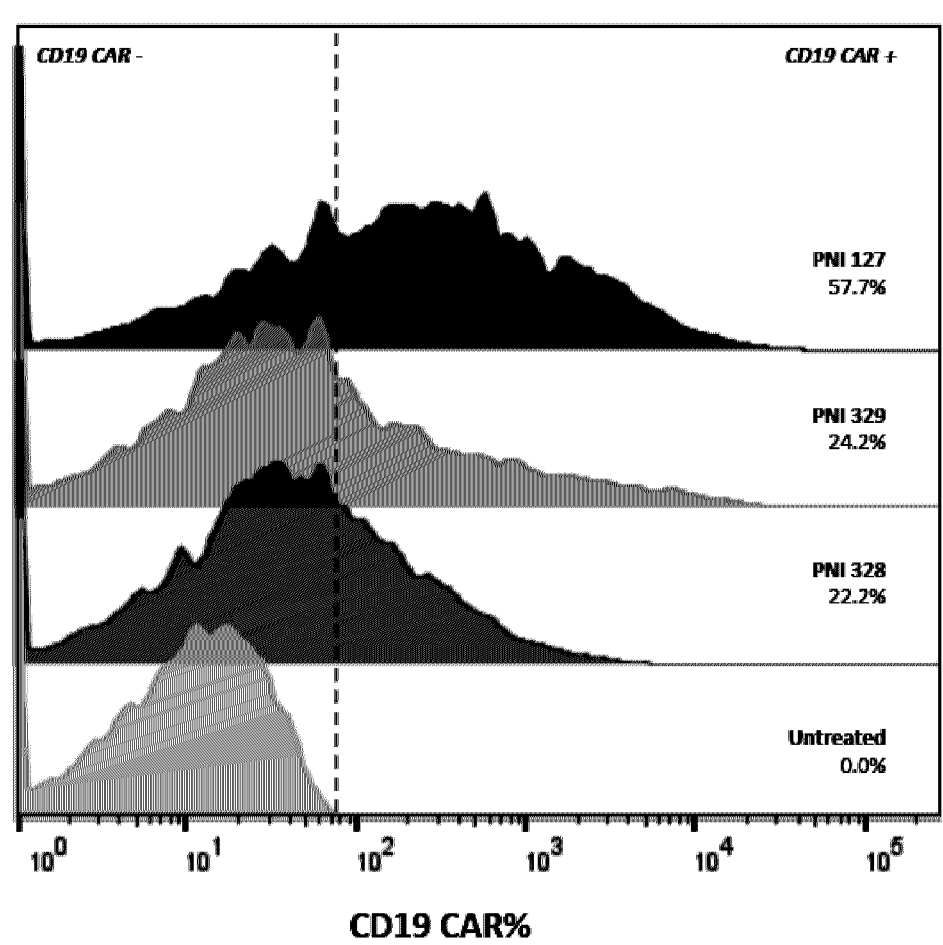
FIG. 11 is a flow cytometry histogram of CD19 CAR positive T cells (CAR+ right of dotted line) 48 h after treatment with PNI 127, PNI 329, or PNI 328 containing CAR mRNA LNPs (CT10, N/8, 500 ng of encapsulated mRNA per 125,000 treated T cells). Control was untreated human primary T cells. T cells had been activated 3 days prior to treatment.

T cells were isolated from whole blood using a negative isolation procedure and T cell activation, and expansion was carried out by triple activation in ImmunoCult™ Human T Cell Expansion Media as described supra. As seen in FIG. 11, CD19 CAR expression was greater than PBS for PNI PNI 328, PNI 329, and PNI127 LNP in transfected T cells in vitro.

Example 24

In Vivo Delivery of OVA-Encoded mRNA LNP Via Intramuscular Administration

LNP with the composition LM02b were used to encapsulate OVA antigen encoded CleanCap® OVA WT mRNA [TriLink L7610] or CleanCap® OVA 5-moU mRNA [TriLink L7210]. A lipid mixture of Ionizable lipid, DOPE, Cholesterol, and PEG-DMG2000, all in ethanol, was mixed with a low PH buffered solution of OVA mRNA at an N/P ratio of 8 using a NanoAssemblr® Ignite™ microfluidic mixer. The LNP were filtered using the Amicon™ ultra filtration technique and characterized for Size, PDI and Encapsulation Efficiency. Size and PDI were measured using dynamic light scattering techniques, and nucleic acid encapsulation efficiency was calculated from the Quant-iT RiboGreen RNA assay. The hydrodynamic diameter of these OVA mRNA-LNPs was ~83 nm with a polydispersity index of ~0.1 and an encapsulation efficiency of ~97%

All animals were handled according to the Institutional Animal Care and Use Committee ethics protocols. For experiments, 6-8 week old C57BL/6 mice (n=4) were purchased from Envigo. On days 1 and 10, mice were intramuscularly immunized with 50 µL of OVA LNPs. Each mouse was vaccinated with a dose of 5 µg OVA mRNA encapsulated in LNPs. A dose of 50 pg OVA antigen was used as a positive control. At definite time intervals, 110-130 µL of blood was collected via saphenous bleeding technique, and processed into serum. At 2 weeks post second immunization, animals were euthanized, and blood was collected via cardiac puncture. Blood samples were processed immediately into serum and stored at −80 degrees C. Aliquots of serum samples were thawed and analyzed at appropriate dilutions for OVA expression and for IgG measurements using standard ELISA techniques.

For serum preparation, after collection of the whole blood, the blood was allowed to clot at room temperature for 15-30 minutes. The clot was removed by centrifuging the tubes at 1000-2000×g for 10 min at 4 degrees Celsius. Supernatant was carefully removed and transferred to sterile screw-capped clear polypropylene tubes on ice.

OVA ELISA of serum samples: Mouse sera at 6 h post vaccination/s was collected via saphenous bleed. OVA antigen was measured using standard sandwich ELISA using Ovalbumin (OVA)—ELISA Kit abx150365 (Abbexa Biologics, Inc., Arlington, TX, USA) components and according to the manufacturer's recommendations. Briefly, to an antibody pre-coated 96-well Abrexxa™ microplate, standards, appropriately diluted sera, and biotin-conjugated reagent were added to the wells and incubated for 1 h. The Horseradish peroxidase (HRP)-conjugated reagent was added and incubated for 20 minutes. Stop solution was added to each well, and absorbance at 450 nm was measured using a plate reader, from which the concentration of OVA protein was calculated.

Figure 12:
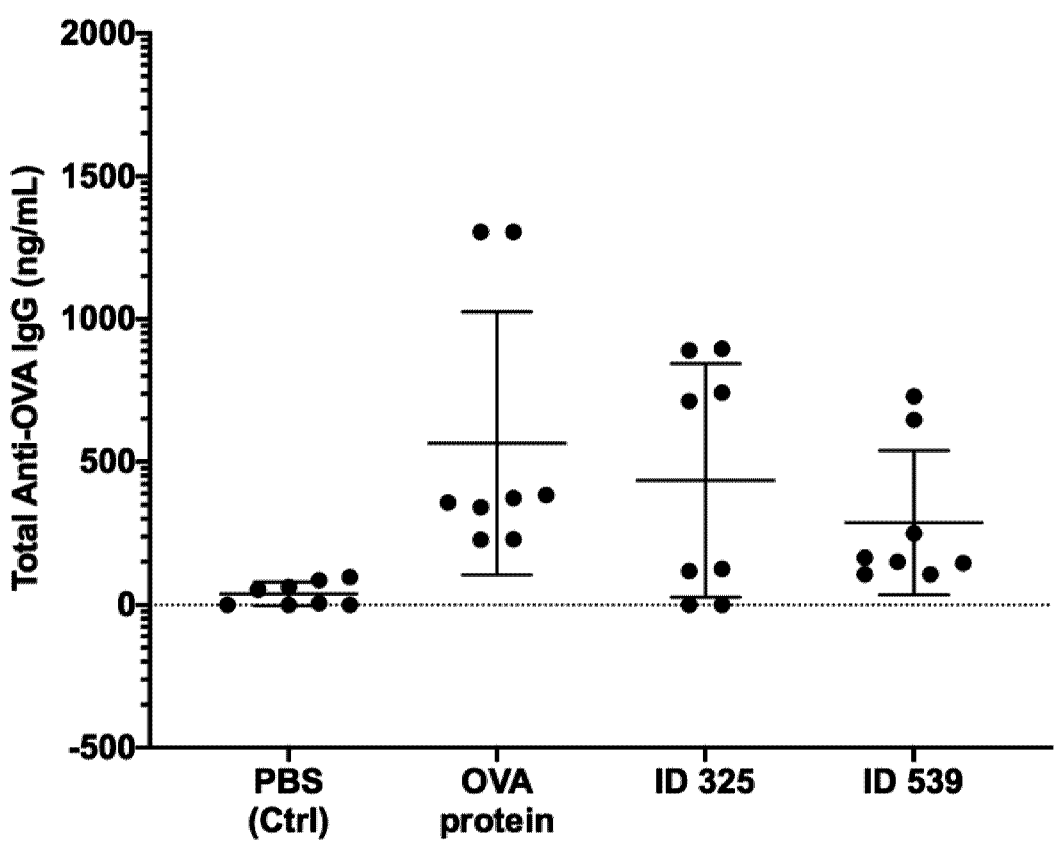
FIG. 12 is a scatter plot illustrating OVA-specific IgG antibody titres in the serum of groups of 4 mice immunized with 5 µg of OVA mRNA LNP vaccines. Two immunizations were done 10 days apart (day 1, day 10), followed by blood draw two weeks post second dose, and OVA specific IgG titre measurements by ELISA. A 50 µg dose of OVA protein was used as a positive control. 5 µg of OVA encoded mRNA resulted in a similar IgG response as that of a 10-fold higher dose of OVA protein.
Figure 13:
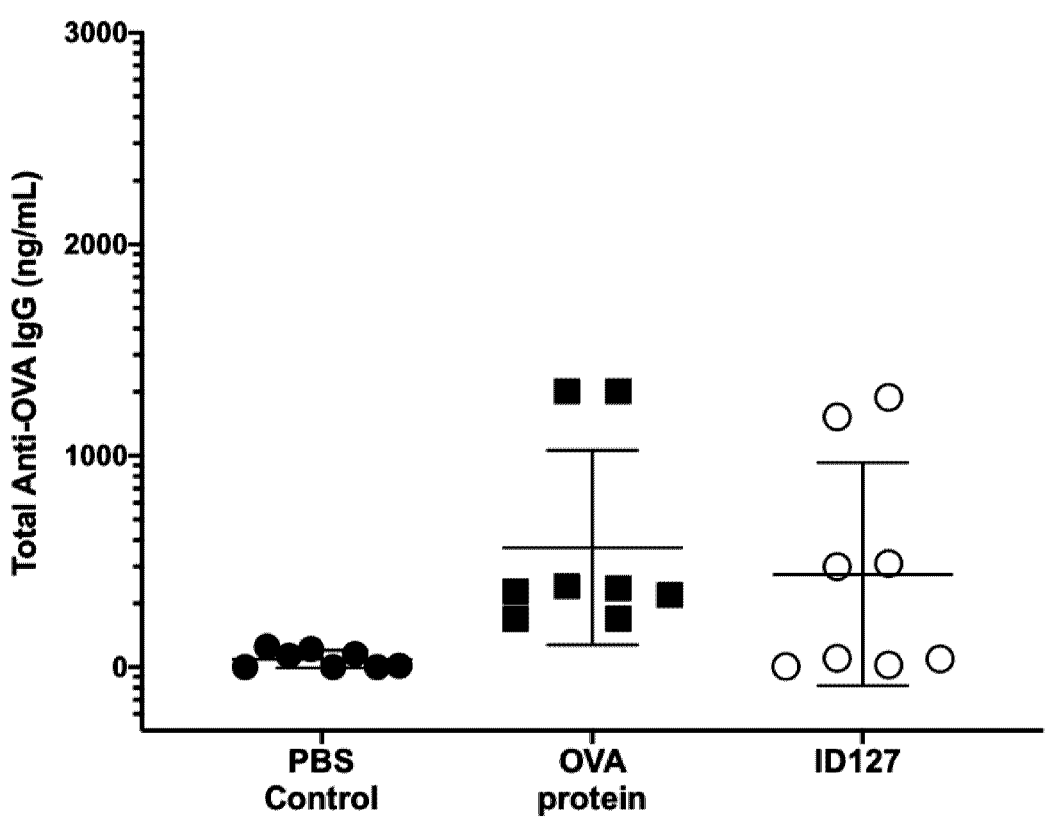
FIG. 13 is a scatter plot illustrating OVA-specific IgG antibody titres in the serum of four individual mice immunized with 10 µg of PBS control, 50 µg OVA protein, or 10 µg OVA mRNA LNP vaccine on day 1 and day 10. OVA-specific IgG titre measurements were generated by ELISA using blood samples drawn two weeks post second dose. Ten µg of OVA-encoded mRNA resulted in the same or higher IgG response as that of a 5 fold higher dose of OVA protein.

Anti OVA-IgG ELISA of serum samples: Sera from the immunized mice were collected at 2 weeks post second immunization. OVA-specific production of IgG in response to OVA-encoded mRNA in various LNPs were measured by ELISA as described supra. Briefly, 96-well ELISA plates were precoated with OVA protein at a concentration of 2 pg protein per well in 100 mM in sodium bicarbonate buffer (pH 9.6) at 4 degrees C. overnight. Precoated plates were then blocked with 10% FBS (BSA) in 7.4 buffered PBS-Tween-20™ (0.05%) v/v and incubated at 37 degrees C. for 2 h. Serum samples and immunoglobulin standards were appropriately diluted (from 1:8 to 1:1000) in 1% BSA-PBS and added to the 96-well plate and incubated for 2 h at RT. (HRP)-conjugated goat anti-mouse IgG (cat #7076, Cell Signaling) was used at a dilution of 1:5,000 in PBS-Tween-10% FBS for labeling and incubated for 1 h. After the incubation period horseradish peroxidase substrate (3,3',5, 5'-tetramethyl benzide—TMB) was added. After 30 minutes of incubation, a stop solution of 2 N sulphuric acid was added and a plate reader was used to determine absorbance at 450 nm. Results are shown in FIG. 12 for PNI ID 325 and 539. Results are shown in FIG. 13 for PNI 127.

Referring to Table 7 as well as the Figures, PNI 121, PNI 127, PNI 328, PNI 329, and PNI 540 are equivalent to MC3 in protein expression in viva PNI 121, PNI 127, PNI 328, PNI 329, and PNI 541 are better than MC3 in terms of the amount of protein produced (Higher MFI's than MC3) in protein expression in human T cells.

OVA antigen loaded LNPs comprising PNI 127, PNI 325, PNI 539 were shown to effectively elicit an immune response similar to OVA antigen showing the utility of PNI lipids for vaccine application.

TABLE 8 pKa values and activity score of various synthesized lipids

| Compound | Exp.pKa | EPO Protein expression score: IV administration in mice | GFP Protein expression score: Human T cell |
|---|---|---|---|
| PNI 76 | 6.4 | ** | **** |
| PNI 119 | 7.5 | * | ** |
| PNI 120 | 7.7 | — | Toxic |
| PNI 121 | 6.8 | * | **** |
| PNI 122 | 7.45 | * | Toxic |
| PNI 127 | 6.46 | **** | ***** |
| PNI 321 | 5.62 | ** | ** |
| PNI 325 | 6.45 | ** | **** |
| PNI 328 | 6.09 | *** | ***** |
| PNI 329 | 5.88 | *** | ***** |
| PNI 336 | 4.57 | ** | * |
| PNI 342 | 6.11 | ** | — |
| PNI 344 | 6.93 | — | — |
| PNI 532 | 5.97 | ** | — |
| PNI 534 | 5.97 | * | * |
| PNI 535 | 4.99 | ** | Not Active |
| PNI 539 | 6.60 | **** | *** |
| PNI 538 | 6.79 | *** | ** |
| PNI 540 | 5.60 | *** | **** |
| PNI 541 | 6.46 | ** | ***** |

Example 25 pKa Studies

The effect on transgene expression after LNP transfection exerted by surface pKa in the LNP resulting from different ionizable lipids was investigated.

The pKa of each cationic lipid was determined in lipid nanoparticles using an assay based on fluorescence of 6-(p-Toluidino)-2-naphthalenesulfonic acid sodium salt (TNS, Sigma Aldrich), which is a fluorescent probe for the conformational state of proteins[5]. Empty lipid nanoparticles comprising ionizable lipid in LM02 composition in distilled water at a concentration of 3.125 mM total lipid are formulated using NanoAssemblr® Spark™, and were then was characterized for LNP quality on the Zetasizer™ using a 30× dilution with 1×PBS in the low volume cuvette. Lipid nanoparticles were further diluted 4× using distilled water to 0.781 mM total lipid. TNS was prepared as a 25 µM stock solution in distilled water. Then 6.4 µL of diluted LNP samples of 0.781 mM total lipid were mixed with 10 µL of diluted TNS to a final volume of 250 µL with buffer containing 10 mM HEPES, 10 mM MES, 10 mM $NH_4OAc$ and 130 mM NaCl where the pH ranged from 3 to 9 in 0.5 pH increments. Each well had a final concentration of 20 µM total lipid, 1 µM TNS, and 233.4 µL of buffer solution (to make up a total volume of 250 µL).

Samples were mixed thoroughly, and the fluorescence intensity was measured at room temperature in a BioTek™ Synergy™ H1 Hybrid Multi-Mode Monochromator™ Fluorescence Microplate Reader using excitation and emission wavelengths of 321 nm and 445 nm respectively. A sigmoidal best fit analysis was applied to the fluorescence data using GraphPad Prism™ software, and the pKa was measured as the pH at half-maximal fluorescence intensity.

Figure 14:
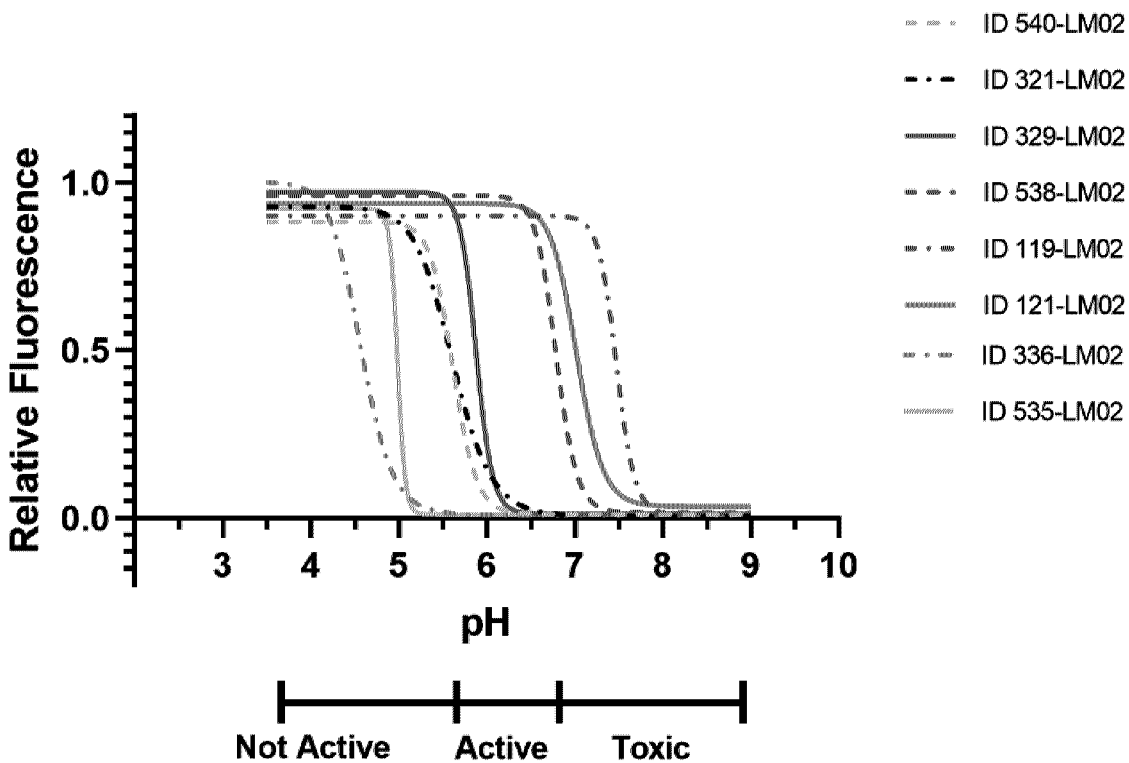
FIG. 14 is a graph illustrating TNS curves indicating surface pKa measurements of LNPs incorporating various ionizable lipids compounds PNI 119, PNI 121, PNI 321, PNI 329, PNI 336, PNI 535, PNI 538 and PNI 540 (LM02 composition).

Results are shown in FIG. 14, which illustrates surface pKa measurements of LNPs incorporating ionizable lipids compounds PNI 119, PNI 121, PNI 321, PNI 329, PNI 336, PNI 535, PNI 538 and PNI 540 (LM02 composition). Lipids with lower pKa values were found to be inactive in transgene expression in T cells. Lipids with high PKa values were found to be toxic to T cells. Lipids in the pKa range of 5.5-6.9 were found to be active in promoting the transgene expression in T cells.

Example 26

Plasmid Encapsulation pCX-EGFP Plasmid size 5514 nt, custom made by GenScript USA Inc, Piscataway, NJ, was used. Lipid particle preparation is as described above. PNI ionizable lipids PNI 121, PNI 127, PNI 328, PNI 329, and PNI 541 were tested for their ability to encapsulate a plasmid suitable for mammalian expression (as above) using an LM02 composition at N/P 6 using the NanoAssemblr® Ignite™ system. All lipids tested generated acceptable LNPs with an average hydrodynamic diameter of 110 nm, and PDI of 0.2 with encapsulation efficiency greater than 80%.

While preferred embodiments have been described above and illustrated in the accompanying drawings, it will be evident to those skilled in the art that modifications may be made without departing from this disclosure. Such modifications are considered as possible variants comprised in the scope of the disclosure.

BIBLIOGRAPHY

1. Garg, S.; Heuck, G.; Ip, S.; Ramsay, E., Microfluidics: a transformational tool for nanomedicine development and production. *J Drug Target* 2016, 24 (9), 821-835.
2. Zhang, S.-h.; Shen, S.-c.; Chen, Z.; Yun, J.-x.; Yao, K.-j.; Chen, B.-b.; Chen, J.-z., Preparation of solid lipid nanoparticles in co-flowing microchannels. *Chemical Engineering Journal* 2008, 144 (2), 324-328.
3. JEFFS, L. B., et al., A Scalable, Extrusion-Free Method for Efficient Liposomal Encapsulation of Plasmid DNA. *Pharmaceutical Research* 2005, 22 (3), 362-372.
4. Gaj, T.; Gersbach, C. A.; Barbas, C. F., 3rd, ZFN, TALEN, and CRISPR/Cas-based methods for genome engineering. *Trends in biotechnology* 2013, 31 (7), 397-405.
5. McClure, W. O.; Edelman, G. M., Fluorescent Probes for Conformational States of Proteins. I. Mechanism of Fluorescence of 2-p-Toluidinylnaphthalene-6-sulfonate, a Hydrophobic Probe*. *Biochemistry* 1966, 5 (6), 1908-1919.
6. Trickett, A.; Kwan, Y. L., T cell stimulation and expansion using anti-CD3/CD28 beads. *J Immunol Methods* 2003, 275 (1-2), 251-5.

US 12,636,368 B2

219

BIBLIOGRAPHY

7. Lundstrom, K. Nanoparticle-based delivery of self-amplifying RNA. Gene Ther 27, 183-185 (2020).
8. Peng, M., Mo, Y., Wang, Y. et al. Neoantigen vaccine: an emerging tumor immunotherapy. *Mol Cancer* 18, 128 (2019).
9. Roujian Lu 1, Xiang Zhao 1, Juan Li 2, et al. "Genomic Characterisation and Epidemiology of 2019 Novel Coronavirus: Implications for Virus Origins and Receptor Binding" Lancet 2020 Feb. 22; 395(10224):565-574.
10. Morokata T, et. al, Immunology (1999) 345-351.
Giuliani et al. (2006) Proc Natl Head Sci USA 103(29): 10834-9

The invention claimed is:

1. A compound, or a pharmaceutically acceptable salt thereof, of formula (II):

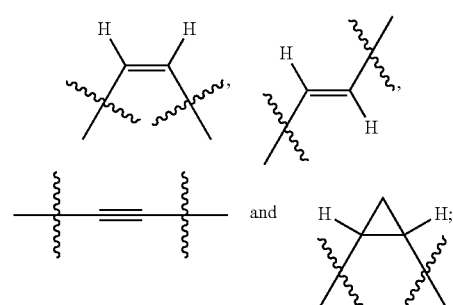

(II)

wherein $E_1$ is selected from the group consisting of —O-$\delta^1$, —OC(O)O-$\delta^1$, —OC(O)-$\delta^1$, —OC(O)N(Q)-$\delta^1$, —OC(O)S-$\delta^1$, —C(O)N(Q)-$\delta^1$, —C(O)O-$\delta^1$, —N(Q)C(O)-$\delta^1$, —N(Q)C(O)O-$\delta^1$, —N(Q)C(O)S-$\delta^1$, and —N(Q)C(O)N(Q)-$\delta^1$;
Q is H or a $C_1$-$C_5$ alkyl; $\delta^1$ designates the bond linked to $R^1$;
$R^1$ is selected from the group consisting of:

wherein:
$R^3$ and $R^4$ are each independently selected from the group consisting of $C_1$-$C_6$ alkyl, $C_2$-$C_6$ alkenyl, and $C_2$-$C_6$ alkynyl; alternatively $R^3$ and $R^4$ may join to form a 4-6 membered ring containing oxygen (O) or up to 2 nitrogen (N), optionally substituted with 1-2 substituents, each independently selected from the group consisting of $C_1$-$C_6$ alkyl, cyclopropyl, OH, and $C_1$-$C_3$ alkoxy;
$R^5$ is selected from the group consisting of $C_1$-$C_6$ alkyl, $C_2$-$C_6$ alkenyl, $C_2$-$C_6$ alkynyl, $C_3$-$C_6$ cycloalkyl, and 2-hydroxyethyl;
$R^6$ is H or a $C_1$-$C_6$ alkyl;
a is 1, 2, 3, 4 or 5;
b and c are independently 0, 1, or 2;
c' is 1, 2, 3, 4, or 5;

220 d is 1 or 2;
e is 0, 1, or 2;
each of $E_2$ is selected from the group consisting of —OC(O)-$\delta^2$, —OC(O)O-$\delta^2$, —OC(O)N(Q)-$\delta^2$, —O-$\delta^2$, —OCH$_2$CH$_2$O-$\delta^2$, and —OC(O)(CH$_2$)$_6$C(O) O-$\delta^2$; Q is H or a $C_1$-$C_5$ alkyl; $\delta^2$ designates the bond linked to $R^2$;
$R^2$ is or has the formula —(CH$_2$)$_g$-[L$_3$-(CH$_2$)]$_h$—R$^9$, wherein:
$L_1$ and $L_2$ are each, independently, a direct bond, —O-$\delta^3$, —CH$_2$OC(O)-$\delta^3$, or —CH$_2$O-$\delta^3$; $\delta^3$ designates the bond linked to the respective one of $R^7$ and $R^8$;
$R^7$ and $R^8$ are each independently a $C_4$-$C_{10}$ alkyl, a $C_4$-$C_{10}$ alkenyl or a $C_4$-$C_{10}$ alkynyl;
f is 0, 1, 2, 3, 4, or 5;
$L_3$ is selected from the group consisting of $R^9$ is H or a $C_4$-$C_8$ alkyl;
g is an integer in the range of 1-18; and
h is 0, 1, 2, or 3.
2. A compound, or a pharmaceutically acceptable salt thereof, of formula (II)

(II)

wherein $E_1$ is selected from the group consisting of —OC(O)O-$\delta^1$, —OC(O)-$\delta^1$, —OC(O)N(Q)-$\delta^1$, and —OC(O)S-$\delta^1$; Q is H or a $C_1$-$C_5$ alkyl; and $\delta^1$ designates the bond linked to $R^1$;
$R^1$ is selected from the group consisting of:

-continued

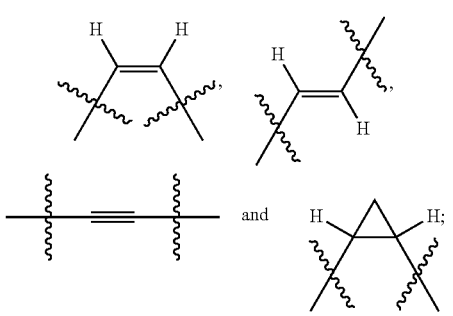

wherein:

$R^3$ and $R^4$ are each independently selected from $C_1$-$C_6$ alkyl; alternatively $R^3$ and $R^4$ may join to form a 5-6 membered ring containing up to 2 nitrogen (N), optionally substituted with 1-2 substituents, each independently selected from $C_1$-$C_6$ alkyl;

$R^5$ is a $C_1$-$C_6$ alkyl or a $C_3$-$C_6$ cycloalkyl;

$R^6$ is an H or a $C_1$-$C_6$ alkyl;

a is 1, 2, 3, or 4;

b and c are independently 0, 1, or 2;

c' is 2, 3, or 4;

d is 2;

e is 0 or 1;

each of $E_2$ is selected from the group consisting of —O-$\delta^2$, —OC(O)-$\delta^2$, —OCH$_2$CH$_2$O-$\delta^2$, and —OC(O) (CH$_2$)$_6$C(O)O-$\delta^2$; where $\delta^2$ designates the bond linked to $R^2$;

$R^2$ is or has the formula —(CH$_2$)$_g$-[L$_3$-(CH$_2$)]$_h$—R$^9$, wherein:

$L_1$ and $L_2$ are each, independently, a direct bond, —O-$\delta^3$, —CH$_2$OC(O)-$\delta^3$, or —CH$_2$O-$\delta^3$; $\delta^3$ designates the bond linked to the respective one of $R^7$ and $R^8$;

$R^7$ and $R^8$ are each independently a $C_4$-$C_{10}$ alkyl, a $C_4$-$C_{10}$ alkenyl or a $C_4$-$C_{10}$ alkynyl;

f is 0, 1, 2, 3, 4, or 5;

$L_3$ is selected from the group consisting of and $R^9$ is H or a $C_4$-$C_8$ alkyl;

g is an integer in the range of 1-18; and h is 0, 1, or 2.

3. A compound, or a pharmaceutically acceptable salt thereof, of formula (II)

(II)

wherein $E_1$ is selected from the group consisting of —OC(O)O-$\delta^1$, —OC(O)-$\delta^1$, —OC(O)N(Q)-$\delta^1$, and —OC(O)S-$\delta^1$; Q is H or a $C_1$-$C_5$ alkyl; and $\delta^1$ designates the bond linked to R$^1$;

$R^1$ is selected from the group consisting of:

wherein:

$R^3$ and $R^4$ are each independently selected from $C_1$-$C_6$ alkyl; alternatively $R^3$ and $R^4$ may join to form a 5-6 membered ring containing up to 2 nitrogen (N), optionally substituted with 1-2 substituents, each independently selected from $C_1$-$C_6$ alkyl;

$R^5$ is a $C_1$-$C_6$ alkyl or cyclopropyl;

$R^6$ is H or a $C_1$-$C_6$ alkyl;

a is 1, 2, 3, or 4;

b is 0 or 1;

c is 0, 1, or 2;

c' is 2, 3, or 4;

d is 2;

e is 1;

each of $E_2$ is selected from the group consisting of —O-$\delta^2$, —OC(O)-$\delta^2$, —OCH$_2$CH$_2$O-$\delta^2$, and —OC(O) (CH$_2$)$_6$C(O)O-$\delta^2$; where $\delta^2$ designates the bond linked to $R^2$;

$R^2$ is or has the formula —(CH$_2$)$_g$-[L$_3$-(CH$_2$)]$_h$—R$^9$, wherein:

$L_1$ and $L_2$ are each a direct bond;

$R^7$ and $R^8$ are each independently selected from $C_4$-$C_{10}$ alkyl;

f is 0 or 1;

$L_3$ is selected from the group consisting of

, and $R^9$ is H or a $C_4$-$C_8$ alkyl;
g is an integer in the range of 1-18; and
h is 0, 1, or 2.

4. A compound, or a pharmaceutically acceptable salt thereof, of formula (III)

(III)

wherein $R^1$ is selected from the group consisting of:

wherein:
$R^3$ and $R^4$ are each independently selected from $C_1$-$C_6$ alkyl; alternatively $R^3$ and $R^4$ may join to form a 5-6 membered ring containing up to 2 nitrogen (N), optionally substituted with 1-2 substituents, each independently selected from $C_1$-$C_6$ alkyl;
$R^5$ is a $C_1$-$C_6$ alkyl or cyclopropyl;
$R^6$ is H or a $C_1$-$C_6$ alkyl;
a is 1, 2, 3, or 4;
b is 0 or 1;
c is 0, 1, or 2;
c' is 2, 3, or 4;
dis 2;
e is 1;
each of $E_2$ is selected from the group consisting of
—O-$\delta^2$, —OC(O)-$\delta^2$, —OCH$_2$CH$_2$O-$\delta^2$, and —OC(O)(CH$_2$)$_6$C(O)O-$\delta^2$; where $\delta^2$ designates the bond linked to $R^2$;
$R^2$ is or has the formula —(CH$_2$)$_g$-[L$_3$-(CH$_2$)]$_h$—R$^9$, wherein:
$L_1$ and $L_2$ are each a direct bond;
$R^7$ and $R^8$ are each independently selected from $C_4$-$C_{10}$ alkyl;
f is 0 or 1;
$L_3$ is selected from the group consisting of , and $R^9$ is H or a $C_4$-$C_8$ alkyl;
g is an integer in the range of 1-18; and
h is 0, 1, or 2.

5. A compound according to any one of the following structures:

PNI 119

PNI 120

225                                                                                                          226

-continued

PNI 121

PNI 122

PNI 127

PNI 321

-continued

PNI 325

PNI 328

PNI 329

PNI 336

US 12,636,368 B2

229          230

-continued

PNI 342

PNI 344

PNI 532

PNI 534       PNI 535

-continued

PNI 539

PNI 538

PNI 540

PNI 541

PNI 573

-continued

PNI 574

PNI 575

PNI 576

PNI 577

PNI 578

235                                                              236

-continued

PNI 579

PNI 580

PNI 581

PNI 582

PNI 583

PNI 369 or a pharmaceutically acceptable salt thereof.

6. A compound according to any one of the following structures:

PNI 326

PNI 624

PNI 625

PNI 626

PNI 627

-continued

PNI 628

PNI 629

PNI 630

PNI 631

PNI 632

PNI 633

-continued

PNI 634

PNI 635

PNI 636

PNI 637

PNI 638

243

244

-continued

PNI 639

PNI 640

PNI 641

PNI 642

PNI 343

-continued

PNI 643

PNI 644

PNI 645

PNI 646

PNI 647

-continued

PNI 648

PNI 649

PNI 650

PNI 348

-continued

PNI 349

PNI 350

PNI 351

-continued

PNI 352

PNI 353

PNI 651

PNI 652

253

254

PNI 653

PNI 654

PNI 655

255
256

-continued

PNI 656

PNI 657

PNI 658

PNI 659

PNI 660

PNI 661

257 258

-continued

PNI 662

PNI 663

PNI 634

PNI 635

PNI 638

-continued

PNI 372

PNI 373

PNI 665

PNI 666

PNI 667

-continued

PNI 668

PNI 669

PNI 670

PNI 671

-continued
PNI 672
PNI 673
PNI 674
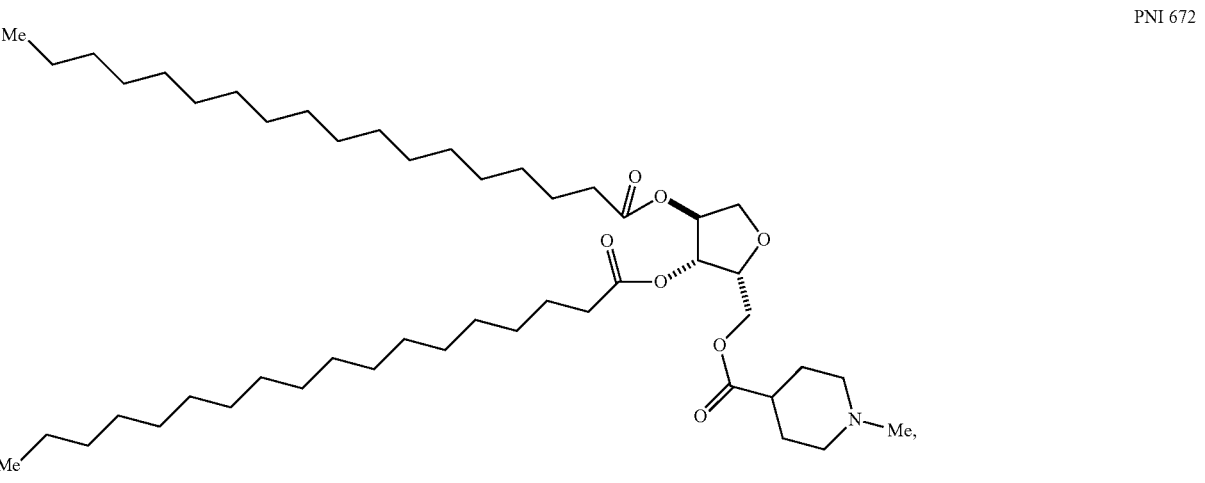

PNI 675
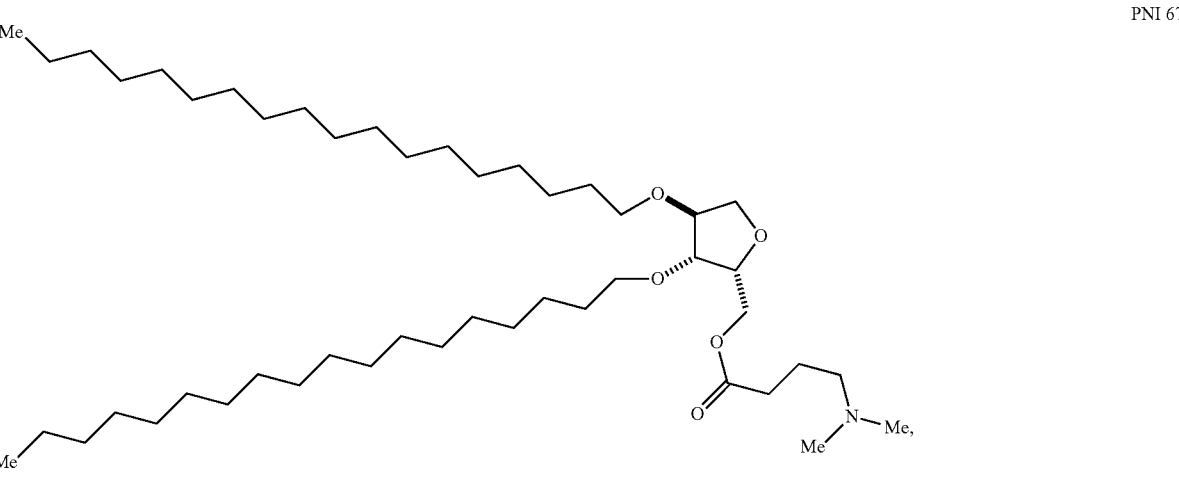
PNI 676
PNI 677

-continued
PNI 678
PNI 679
PNI 340
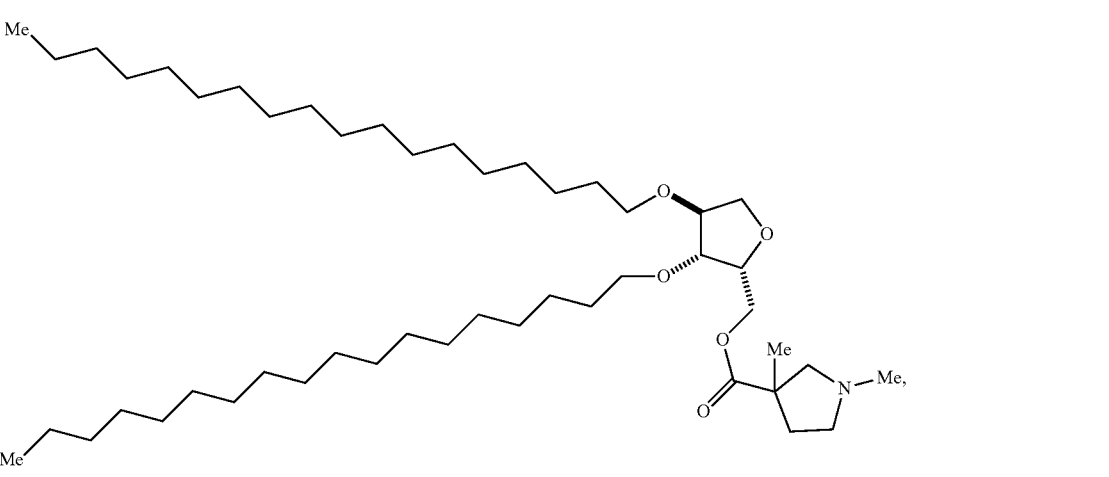

-continued

PNI 341

PNI 680

PNI 681

PNI 682

271                                                                                                   272

-continued

PNI 683

PNI 684

PNI 685

PNI 686

PNI 687

273 274

-continued

PNI 688

PNI 383

PNI 385

PNI 386

PNI 389

275
276
-continued
PNI 390
PNI 689
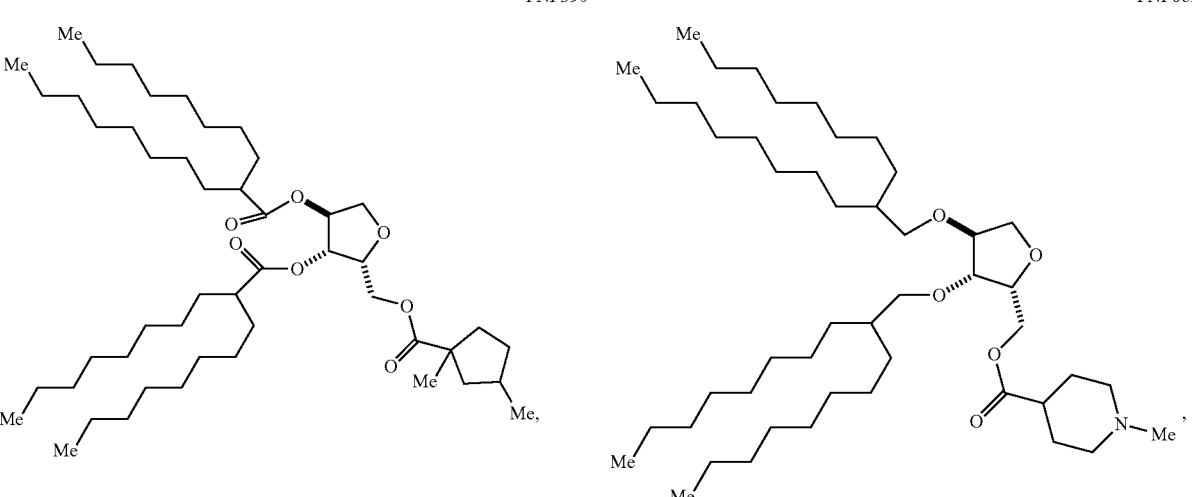
PNI 690
PNI 399

277 278

PNI 401

PNI 402

PNI 405

PNI 406

279

280

PNI 691

PNI 692

PNI 693

PNI 694

-continued

PNI 695

PNI 696 m = 0-5

PNI 697 m = 0-5

-continued

PNI 698 m = 0-5

PNI 699 m = 0-5

PNI 700 m = 0-5

-continued

PNI 701 m = 0-4

PNI 702 m = 0-4

PNI 703 m = 0-4

-continued

PNI 704 m = 0-4

PNI 705 m = 0-4

PNI 337

-continued

PNI 322

PNI 323

PNI 324

PNI 331

-continued

PNI 327

PNI 335

PNI 706

PNI 707

-continued

PNI 708

PNI 346

PNI 347

PNI 355

-continued

PNI 361

PNI 366

PNI 367

-continued

PNI 379

PNI 398                                                        PNI 400

PNI 408

-continued

PNI 709 m' = 0-4

PNI 710 m' = 0-4 or a pharmaceutically acceptable salt thereof.

7. A lipid mix composition comprising any of the compounds of claim 1, combined with one or more of a structural lipid, a sterol, or a stabilizing agent.

8. The lipid mix composition of claim 7, wherein the structural lipid comprises one or more structural lipids selected from the group consisting of distearoylphosphatidylcholine (DSPC), dioleoylphosphatidylcholine (DOPC), dipalmitoylphosphatidylcholine (DPPC), dioleoyl-phosphatidylethanolamine (DOPE), 1,2-dimyristoyl-sn-glycero-3-phosphocholine (DMPC), palmitoyloleoylphosphatidylcholine (POPC), palmitoyloleoyl-phosphatidylethanolamine (POPE), dipalmitoyl phosphatidyl ethanolamine (DPPE), dimyristoylphosphoethanolamine (DMPE), distearoyl-phosphatidylethanolamine (DSPE), and sphingomyelins (SM) DSPC, DSPE, DPPC, DMPC, DOPC, POPC, DOPE and SM.

9. The lipid mix composition of claim 7, wherein the compound is present at about 10 Mol %-90 Mol %, the structural lipid is present at about 0-50 Mol %, the sterol is present at about 0-45 Mol %, and the stabilizing agent is present at 0-10 Mol %; and the total mol % of components of the lipid mix composition is 100 mol %.

10. The lipid mix composition of claim 7, wherein the compound is present at about 40 Mol %-60 Mol %, and the structural lipid is present at about 11-40 Mol %; and the total mol % of components of the lipid mix composition is 100 mol %.

11. The lipid mix composition of claim 7, wherein the compound is present at about 30 Mol % to 70 Mol %, wherein the total mol % of components of the lipid mix composition is 100 mol %.

12. A lipid particle comprising the lipid mix composition of claim 7 and at least one therapeutic agent encapsulated therein.

13. The compound of claim 1, wherein one of the hydrogens is substituted with a halogen.

14. The compound or a pharmaceutically acceptable salt thereof, of claim 1, wherein the experimental pKa of nanoparticles is in the range 5.6-7.1.

15. A pharmaceutical composition comprising the compound of claim 1, and at least one pharmaceutically acceptable carrier or excipient.

16. The lipid mix composition of claim 7, wherein the structural lipid includes DSPC, the sterol includes cholesterol, and the stabilizing agent includes polyoxyethylene (10) stearyl ether, and wherein the compound is present at 40 Mol %, DSPC is present at 20 Mol %, cholesterol is present at 37.5 Mol %, and polyoxyethylene (10) stearyl ether is present at 2.5 Mol %.

17. The lipid mix composition of claim 7, wherein the structural lipid includes DSPC, the sterol includes cholesterol, and the stabilizing agent includes PEG-DMG 2000, and wherein the compound is present at 40 to 47.5 Mol %, DSPC is present at 12.5 Mol %, cholesterol is present at 38.5 to 46 Mol %, and PEG-DMG 2000 is present at 1.5 Mol %.

18. The lipid mix composition of claim 7, wherein the structural lipid includes DOPE, the sterol includes cholesterol, and the stabilizing agent includes PEG-DMG 2000, and wherein the compound is present at 40 to 47.5 Mol %, DOPE is present at 12.5 Mol %, cholesterol is present at 38.5 to 46 Mol %, and PEG-DMG 2000 is present at 1.5 Mol %.

19. The lipid mix composition of claim 7, wherein the structural lipid is present at about 10 to 40 Mol % of the lipid mix composition.

20. The lipid mix composition of claim 7, wherein the sterol includes cholesterol, and the cholesterol is present at about 30 to 50 Mol % of the lipid mix composition.

21. The lipid mix composition of claim 7, wherein the stabilizing agent is present at about 0.1 to 3 Mol % of the lipid mix composition.

22. The lipid mix composition of claim 7, wherein the stabilizing agent is present at greater than 2.5 Mol % of the lipid mix composition.

23. The lipid mix composition of claim 7, wherein the stabilizing agent comprises polysorbate 80, Polyoxyethylene (40) stearate, polyoxyethylene (10) stearyl ether, a polyethylene glycol conjugated lipid, or combinations thereof.

\*  \*  \*  \*  \*